US011186832B2

(12) United States Patent
Marozsan

(10) Patent No.: US 11,186,832 B2
(45) Date of Patent: Nov. 30, 2021

(54) TREATING MUSCLE WEAKNESS WITH ALKALINE PHOSPHATASES

(71) Applicant: Alexion Pharmaceuticals, Inc., Boston, MA (US)

(72) Inventor: Andre Marozsan, Milford, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 79 days.

(21) Appl. No.: 16/089,744

(22) PCT Filed: Mar. 31, 2017

(86) PCT No.: PCT/US2017/025618
§ 371 (c)(1),
(2) Date: Sep. 28, 2018

(87) PCT Pub. No.: WO2017/173413
PCT Pub. Date: Oct. 5, 2017

(65) Prior Publication Data
US 2019/0119659 A1    Apr. 25, 2019

Related U.S. Application Data

(60) Provisional application No. 62/317,125, filed on Apr. 1, 2016.

(51) Int. Cl.
*C12N 9/16*    (2006.01)
*A61K 38/46*    (2006.01)
*A61P 21/00*    (2006.01)
*A61K 9/00*    (2006.01)
*C07K 16/46*    (2006.01)

(52) U.S. Cl.
CPC ............. *C12N 9/16* (2013.01); *A61K 9/0019* (2013.01); *A61K 38/465* (2013.01); *A61P 21/00* (2018.01); *C07K 16/462* (2013.01); *C12Y 301/03001* (2013.01)

(58) Field of Classification Search
None
See application file for complete search history.

(56) References Cited

U.S. PATENT DOCUMENTS

| | | | |
|---|---|---|---|
| 5,336,759 A | 8/1994 | Matsuo et al. |
| 5,338,830 A | 8/1994 | Matsuo et al. |
| 5,340,920 A | 8/1994 | Matsuo et al. |
| 5,352,770 A | 10/1994 | Matsuo |
| 5,428,130 A | 6/1995 | Capon et al. |
| 5,434,133 A | 7/1995 | Tanaka et al. |
| 5,583,108 A | 12/1996 | Wei et al. |
| 5,665,704 A | 9/1997 | Lowe et al. |
| 5,714,147 A | 2/1998 | Capon et al. |
| 5,767,239 A | 6/1998 | Immer et al. |
| 5,846,932 A | 12/1998 | Lowe et al. |
| 5,948,761 A | 9/1999 | Seilhamer et al. |
| 5,973,134 A | 10/1999 | Matsuo et al. |
| 6,020,168 A | 2/2000 | Matsuo et al. |
| 6,028,055 A | 2/2000 | Lowe et al. |
| 6,034,231 A | 3/2000 | Tanaka et al. |
| 6,290,952 B1 | 9/2001 | Poelstra et al. |
| 6,406,697 B1 | 6/2002 | Capon et al. |
| 6,407,211 B1 | 6/2002 | Burnett, Jr. et al. |
| 6,420,384 B2 | 7/2002 | Weigele et al. |
| 6,436,386 B1 | 8/2002 | Roberts et al. |
| 6,455,495 B1 | 9/2002 | Orgel et al. |
| 6,458,579 B2 | 10/2002 | Hopwood et al. |
| 6,525,022 B1 | 2/2003 | Lowe et al. |
| 6,541,610 B1 | 4/2003 | Smith |
| 6,743,425 B2 | 6/2004 | Nakao |
| 6,790,649 B1 | 9/2004 | Crine et al. |
| 6,818,619 B2 | 11/2004 | Burnett, Jr. et al. |
| 6,830,885 B1 | 12/2004 | Lanctot et al. |
| 6,849,714 B1 | 2/2005 | Bridon et al. |
| 6,887,470 B1 | 5/2005 | Bridon et al. |
| 6,905,689 B2 | 6/2005 | Schneidinger et al. |
| 6,946,484 B2 | 9/2005 | Adams et al. |
| 7,026,293 B2 | 4/2006 | Kitakaze |
| 7,033,997 B2 | 4/2006 | Forssmann et al. |
| 7,070,974 B1 | 7/2006 | Desgroseillers et al. |
| 7,105,539 B2 | 9/2006 | Gravel et al. |
| 7,179,903 B2 | 2/2007 | McArthur et al. |
| 7,256,253 B2 | 8/2007 | Bridon et al. |

(Continued)

FOREIGN PATENT DOCUMENTS

| | | |
|---|---|---|
| EP | 0478797 B1 | 4/1995 |
| EP | 0769554 A2 | 4/1997 |

(Continued)

OTHER PUBLICATIONS

"Highly Specialised Technology Evaluation: Asfotase alfa for treating paediatric-onset hypophosphatasia [ID 758]," Oct. 21, 2015, <https://www.nice.org.uk/guidance/hst6/documents/committee-papers-8>, (99 pages).
"View of NCT02235493 on Nov. 19, 2015," ClinicalTrials.gov archive, Nov. 19, 2015 (4 pages).
Achord et al., "Human beta-glucuronidase: in vivo clearance and in vitro uptake by a glycoprotein recognition system on reticuloendothelial cells," Cell 15(1):269-278 (1978).
Addison et al., "Pyrophosphate inhibits mineralization of osteoblast cultures by binding to mineral, up-regulating osteopontin, and inhibiting alkaline phosphatase activity," J Biol Chem. 282(21):15872-15883 (2007).
Advisory Action for U.S. Appl. No. 11/484,870, dated Dec. 20, 2007 (4 pages).
Ahn et al., "Idiopathic calcium pyrophosphate dihydrate (CPPD) crystal deposition disease in a young male patient: a case report," J Korean Med Sci. 18(6):917-20 (2003).

(Continued)

Primary Examiner — Hope A Robinson
(74) Attorney, Agent, or Firm — Clark & Elbing LLP

(57) ABSTRACT

The disclosure features methods for treating or ameliorating at least one symptom of a subject having or being prone to a muscle weakness disease, comprising administering to said subject a therapeutically effective amount of at least one recombinant polypeptide having alkaline phosphatase activity.

23 Claims, 6 Drawing Sheets
Specification includes a Sequence Listing.

(56) References Cited

U.S. PATENT DOCUMENTS

| | | |
|---|---|---|
| 7,271,149 B2 | 9/2007 | Glaesner et al. |
| 7,276,481 B2 | 10/2007 | Golembo et al. |
| 7,341,838 B2 | 3/2008 | Buechler et al. |
| 7,365,091 B2 | 4/2008 | Gravel et al. |
| 7,384,917 B2 | 6/2008 | Burnett, Jr. et al. |
| 7,399,466 B2 | 7/2008 | Boileau |
| 7,414,107 B2 | 8/2008 | Larsen |
| 7,425,531 B2 | 9/2008 | Lanctot et al. |
| 7,427,498 B2 | 9/2008 | Crine et al. |
| 7,470,668 B2 | 12/2008 | Lanctot et al. |
| 7,488,713 B2 | 2/2009 | Vesely |
| 7,527,939 B2 | 5/2009 | Davey et al. |
| 7,563,769 B2 | 7/2009 | Bogin et al. |
| 7,625,564 B2 | 12/2009 | Wang et al. |
| 7,642,243 B2 | 1/2010 | Nakao et al. |
| 7,648,962 B2 | 1/2010 | James et al. |
| 7,662,773 B2 | 2/2010 | James et al. |
| 7,678,391 B2 | 3/2010 | Graham et al. |
| 7,732,406 B2 | 6/2010 | Mitrovic et al. |
| 7,736,653 B2 | 6/2010 | Kim et al. |
| 7,754,852 B2 | 7/2010 | Burnett, Jr. et al. |
| 7,763,712 B2 | 7/2010 | Crine et al. |
| 7,803,769 B2 | 9/2010 | Sullivan et al. |
| 7,803,901 B2 | 9/2010 | Burnett, Jr. et al. |
| 7,825,092 B2 | 11/2010 | Vesely |
| 7,846,900 B2 | 12/2010 | Vesely |
| 7,858,560 B2 | 12/2010 | Koster et al. |
| 7,919,591 B2 | 4/2011 | Sheffer et al. |
| 7,943,126 B2 | 5/2011 | Tomatsu et al. |
| 7,960,529 B2 | 6/2011 | Crine et al. |
| 8,058,242 B2 | 11/2011 | Alewood et al. |
| 8,691,208 B2 | 4/2014 | Tomatsu et al. |
| 9,266,939 B2 | 2/2016 | Crine et al. |
| 9,988,620 B2 | 6/2018 | Crine et al. |
| 10,000,532 B2 | 6/2018 | Crine et al. |
| 10,017,580 B2 * | 7/2018 | Van Berkel ......... A61K 47/6851 |
| 10,052,366 B2 * | 8/2018 | Crine ...................... C07K 7/08 |
| 10,603,361 B2 | 3/2020 | Odrljin |
| 2002/0183276 A1 | 12/2002 | Millan et al. |
| 2003/0158132 A1 | 8/2003 | Kovesdi |
| 2004/0023916 A1 | 2/2004 | Millan et al. |
| 2004/0077537 A1 | 4/2004 | Schreiner |
| 2004/0234518 A1 | 11/2004 | Crine et al. |
| 2005/0113286 A1 | 5/2005 | Schreiner et al. |
| 2005/0142217 A1 | 6/2005 | Adams et al. |
| 2005/0202442 A1 | 9/2005 | Morris et al. |
| 2005/0244904 A1 | 11/2005 | Ng |
| 2005/0276796 A1 | 12/2005 | Tomatsu et al. |
| 2006/0014687 A1 | 1/2006 | Crine et al. |
| 2006/0019890 A1 | 1/2006 | Kapoun et al. |
| 2006/0074009 A1 | 4/2006 | James et al. |
| 2006/0110359 A1 | 5/2006 | Sanchez-Ramos et al. |
| 2006/0172929 A1 | 8/2006 | Rappold-Hoerbrand et al. |
| 2006/0228710 A1 | 10/2006 | Morris et al. |
| 2007/0041972 A1 | 2/2007 | Rother et al. |
| 2007/0042957 A1 | 2/2007 | Burnett et al. |
| 2007/0081984 A1 | 4/2007 | Tomatsu et al. |
| 2007/0081986 A1 | 4/2007 | Tomatsu et al. |
| 2007/0197434 A1 | 8/2007 | Nakao et al. |
| 2007/0281887 A1 | 12/2007 | Pan |
| 2007/0292966 A1 | 12/2007 | Prickett et al. |
| 2007/0293418 A1 | 12/2007 | Larsen |
| 2008/0032933 A1 | 2/2008 | Burnett et al. |
| 2008/0081768 A1 | 4/2008 | Watt et al. |
| 2008/0085862 A1 | 4/2008 | Kim et al. |
| 2008/0113411 A1 | 5/2008 | Sheffer et al. |
| 2008/0113412 A1 | 5/2008 | Sheffer et al. |
| 2008/0125574 A1 | 5/2008 | Sheffer et al. |
| 2008/0153747 A1 | 6/2008 | Alewood et al. |
| 2008/0161243 A1 | 7/2008 | Rosen et al. |
| 2008/0181903 A1 | 7/2008 | Bhaskar et al. |
| 2008/0182299 A1 | 7/2008 | Colocaru et al. |
| 2008/0194481 A1 | 8/2008 | Rosen et al. |
| 2008/0194682 A1 | 8/2008 | Golembo et al. |
| 2008/0227713 A1 | 9/2008 | Protter |
| 2008/0293632 A1 | 11/2008 | Rappold-Hoerbrand et al. |
| 2008/0312142 A1 | 12/2008 | Nakao et al. |
| 2009/0011997 A1 | 1/2009 | Peri et al. |
| 2009/0023652 A1 | 1/2009 | Bell et al. |
| 2009/0053192 A1 | 2/2009 | Millan et al. |
| 2009/0069243 A1 | 3/2009 | Burnett, Jr. et al. |
| 2009/0092582 A1 | 4/2009 | Bogin et al. |
| 2009/0142347 A1 | 6/2009 | Millan |
| 2009/0170756 A1 | 7/2009 | Burnett, Jr. et al. |
| 2009/0221803 A1 | 9/2009 | Dall'Acqua et al. |
| 2009/0238814 A1 | 9/2009 | Tomatsu et al. |
| 2009/0240031 A1 | 9/2009 | Immer et al. |
| 2009/0247462 A1 | 10/2009 | Bogin et al. |
| 2009/0252729 A1 | 10/2009 | Farrington et al. |
| 2009/0258018 A1 | 10/2009 | Medich et al. |
| 2009/0275506 A1 | 11/2009 | Bakis et al. |
| 2009/0325195 A1 | 12/2009 | Davey et al. |
| 2010/0008979 A1 | 1/2010 | Tomatsu et al. |
| 2010/0055150 A1 | 3/2010 | Golembo et al. |
| 2010/0093678 A1 | 4/2010 | Della-Fera et al. |
| 2010/0160212 A1 | 6/2010 | Sheffer et al. |
| 2010/0168443 A1 | 7/2010 | Geysen |
| 2010/0184680 A1 | 7/2010 | Bevec |
| 2010/0197574 A1 | 8/2010 | Chen et al. |
| 2010/0204094 A1 | 8/2010 | Simari et al. |
| 2010/0204109 A1 | 8/2010 | Bevec |
| 2010/0204446 A1 | 8/2010 | Forssmann |
| 2010/0209958 A1 | 8/2010 | Nakao et al. |
| 2010/0216714 A1 | 8/2010 | James et al. |
| 2010/0221234 A1 | 9/2010 | Crine et al. |
| 2010/0240125 A1 | 9/2010 | Crine et al. |
| 2010/0249017 A1 | 9/2010 | Bevec et al. |
| 2010/0260706 A1 | 10/2010 | Bogin et al. |
| 2010/0261248 A1 | 10/2010 | Kim et al. |
| 2010/0297021 A1 | 11/2010 | Wendt et al. |
| 2010/0297119 A1 | 11/2010 | Crine et al. |
| 2010/0305031 A1 | 12/2010 | Wakabayashi et al. |
| 2010/0305051 A1 | 12/2010 | Burnett, Jr. et al. |
| 2010/0310561 A1 | 12/2010 | Canada et al. |
| 2010/0311660 A1 | 12/2010 | Simari et al. |
| 2010/0317600 A1 | 12/2010 | Immer et al. |
| 2010/0331256 A1 | 12/2010 | Wendt et al. |
| 2011/0152194 A1 | 6/2011 | Burnett, Jr. et al. |
| 2011/0250187 A1 | 10/2011 | Tomatsu et al. |
| 2011/0269684 A1 | 11/2011 | Burnett, Jr. et al. |
| 2011/0300143 A1 | 12/2011 | Sly et al. |
| 2012/0088771 A1 | 4/2012 | Millan |
| 2012/0164142 A1 | 6/2012 | Crine et al. |
| 2013/0108635 A1 | 5/2013 | Crine et al. |
| 2013/0323244 A1 | 12/2013 | Crine et al. |
| 2014/0193388 A1 | 7/2014 | Velders et al. |
| 2014/0194484 A1 | 7/2014 | Coats et al. |
| 2015/0353633 A1 | 12/2015 | Kakkis et al. |
| 2016/0052968 A1 | 2/2016 | Crine et al. |
| 2016/0097100 A1 | 4/2016 | Trent et al. |
| 2017/0175094 A1 | 6/2017 | Hatch |
| 2017/0360899 A1 | 12/2017 | Marozsan et al. |
| 2018/0230445 A1 | 8/2018 | Jaluria et al. |

FOREIGN PATENT DOCUMENTS

| | | |
|---|---|---|
| EP | 0771875 B1 | 5/1997 |
| EP | 0466174 B1 | 6/1997 |
| EP | 0475394 B1 | 6/1997 |
| EP | 0466175 B1 | 1/1998 |
| EP | 0477971 B1 | 1/1998 |
| EP | 0475290 B1 | 12/1998 |
| EP | 0475291 B1 | 12/1998 |
| EP | 0497368 B1 | 6/2002 |
| EP | 1492567 | 9/2003 |
| EP | 1502604 A1 | 2/2005 |
| EP | 1623994 A2 | 2/2006 |
| EP | 1759001 B1 | 3/2007 |
| EP | 1759710 A1 | 3/2007 |
| EP | 1985697 A1 | 10/2008 |
| EP | 2158319 | 3/2010 |
| EP | 2158319 B1 | 12/2011 |
| EP | 3250227 A2 | 12/2017 |
| JP | H0870875 A | 3/1996 |

(56) References Cited

FOREIGN PATENT DOCUMENTS

| | | |
|---|---|---|
| JP | 2000-327583 A | 11/2000 |
| JP | 2002-541776 A | 12/2002 |
| JP | 2007-511209 A | 5/2007 |
| JP | 2007-537725 A | 12/2007 |
| JP | 2010-501026 A | 1/2010 |
| JP | 2010-526543 A | 8/2010 |
| JP | 2010-530222 A | 9/2010 |
| JP | 2011-504506 A | 2/2011 |
| WO | WO-92/20371 A1 | 11/1992 |
| WO | WO-94/20534 A1 | 9/1994 |
| WO | WO-95/05456 A1 | 2/1995 |
| WO | WO-95/13296 A1 | 5/1995 |
| WO | WO-95/33769 A1 | 12/1995 |
| WO | WO-98/17690 A1 | 4/1998 |
| WO | WO-98/35703 A2 | 8/1998 |
| WO | WO-99/46283 A1 | 9/1999 |
| WO | WO-00/18954 A2 | 4/2000 |
| WO | WO-00/50580 A2 | 8/2000 |
| WO | WO-00/53755 A2 | 9/2000 |
| WO | WO-00/64486 A2 | 11/2000 |
| WO | WO-00/69900 A2 | 11/2000 |
| WO | WO-01/36620 A2 | 5/2001 |
| WO | WO-01/44284 A2 | 6/2001 |
| WO | WO-01/80890 A2 | 11/2001 |
| WO | WO-02/15918 A2 | 2/2002 |
| WO | WO-02/47871 A1 | 6/2002 |
| WO | WO-02/067639 A1 | 8/2002 |
| WO | WO-02/068579 A2 | 9/2002 |
| WO | WO-02/074234 A2 | 9/2002 |
| WO | WO-03/074082 A1 | 9/2003 |
| WO | WO-03/079979 A2 | 10/2003 |
| WO | WO-03/092581 A2 | 11/2003 |
| WO | WO-03/094835 A2 | 11/2003 |
| WO | WO-2004/011498 A2 | 2/2004 |
| WO | WO-2004/022579 A2 | 3/2004 |
| WO | WO-2004/046194 A2 | 6/2004 |
| WO | WO-2004/047871 A2 | 6/2004 |
| WO | WO-2004/062555 A2 | 7/2004 |
| WO | WO-2004/074320 A2 | 9/2004 |
| WO | WO-2004/094460 A2 | 11/2004 |
| WO | WO-2005/000095 A2 | 1/2005 |
| WO | WO-2005/007809 A2 | 1/2005 |
| WO | WO-2005/042034 A1 | 5/2005 |
| WO | WO-2005/047337 A1 | 5/2005 |
| WO | WO-2005/070446 A1 | 8/2005 |
| WO | WO-2005/072055 A2 | 8/2005 |
| WO | WO-2005/094890 A1 | 10/2005 |
| WO | WO-2005/098490 A1 | 10/2005 |
| WO | WO-2005/103263 A1 | 11/2005 |
| WO | WO-2005/105156 A1 | 11/2005 |
| WO | WO-2005/110435 A1 | 11/2005 |
| WO | WO-2006/005140 A2 | 1/2006 |
| WO | WO-2006/026663 A1 | 3/2006 |
| WO | WO-2006/039480 A2 | 4/2006 |
| WO | WO-2006/060641 A2 | 6/2006 |
| WO | WO-2006/110743 A1 | 10/2006 |
| WO | WO-2006/116260 A2 | 11/2006 |
| WO | WO-2007/041645 A2 | 4/2007 |
| WO | WO-2007/071295 A1 | 6/2007 |
| WO | WO-2007/097923 A2 | 8/2007 |
| WO | WO-2007/130113 A2 | 11/2007 |
| WO | WO-2008/021872 A1 | 2/2008 |
| WO | WO-2008/030558 A2 | 3/2008 |
| WO | WO-2008/031045 A2 | 3/2008 |
| WO | WO-2008/053362 A2 | 5/2008 |
| WO | WO-2008/058016 A2 | 5/2008 |
| WO | WO-2008/079995 A2 | 7/2008 |
| WO | WO-2008/088422 A2 | 7/2008 |
| WO | WO-2008/109903 A1 | 9/2008 |
| WO | WO-2008/136611 A1 | 11/2008 |
| WO | WO-2008/138131 A1 | 11/2008 |
| WO | WO-2008/154226 A1 | 12/2008 |
| WO | WO-2009/006520 A1 | 1/2009 |
| WO | WO-2009/006732 A9 | 1/2009 |
| WO | WO-2009/015011 A1 | 1/2009 |
| WO | WO-2009/023270 A2 | 2/2009 |
| WO | WO-2009/033680 A2 | 3/2009 |
| WO | WO-2009/033724 A1 | 3/2009 |
| WO | WO-2009/033796 A1 | 3/2009 |
| WO | WO-2009/033807 A2 | 3/2009 |
| WO | WO-2009/034134 A2 | 3/2009 |
| WO | WO-2009/036448 A2 | 3/2009 |
| WO | WO-2009/040030 A1 | 4/2009 |
| WO | WO-2009/040031 A2 | 4/2009 |
| WO | WO-2009/040083 A2 | 4/2009 |
| WO | WO-2009/046861 A1 | 4/2009 |
| WO | WO-2009/058322 A1 | 5/2009 |
| WO | WO-2009/067639 A2 | 5/2009 |
| WO | WO-2009/086126 A2 | 7/2009 |
| WO | WO-2009/090553 A2 | 7/2009 |
| WO | WO-2009/142307 A1 | 11/2009 |
| WO | WO-2009/149161 A9 | 12/2009 |
| WO | WO-2009/156481 A1 | 12/2009 |
| WO | WO-2009/158035 A2 | 12/2009 |
| WO | WO-2010/002583 A2 | 1/2010 |
| WO | WO-2010/011096 A2 | 1/2010 |
| WO | WO-2010/048308 A2 | 4/2010 |
| WO | WO-2010/078325 A2 | 7/2010 |
| WO | WO-2010/082804 A2 | 7/2010 |
| WO | WO-2010/117760 A2 | 10/2010 |
| WO | WO-2010/129655 A2 | 11/2010 |
| WO | WO-2010/135541 A2 | 11/2010 |
| WO | WO-2011/130229 A1 | 10/2011 |
| WO | WO-2011/134084 A1 | 11/2011 |
| WO | WO-2012/088608 A1 | 7/2012 |
| WO | WO-2012/099851 A2 | 7/2012 |
| WO | WO-2013/058833 A1 | 4/2013 |
| WO | WO-2013/059491 A1 | 4/2013 |
| WO | WO-2013/071262 A5 | 5/2013 |
| WO | WO-2015/112015 A1 | 7/2015 |
| WO | WO-2015/112017 A1 | 7/2015 |
| WO | WO-2016/007873 A1 | 1/2016 |
| WO | WO-2016/090251 A1 | 6/2016 |
| WO | WO-2016/123342 A2 | 8/2016 |
| WO | WO-2016/153191 A1 | 9/2016 |
| WO | WO-2017/031114 A1 | 2/2017 |
| WO | WO-2017/058822 A1 | 4/2017 |
| WO | WO-2017/074466 A1 | 5/2017 |
| WO | WO-2017/155569 A1 | 9/2017 |
| WO | WO-2017/171871 A1 | 10/2017 |
| WO | WO-2017/173395 A1 | 10/2017 |
| WO | WO-2017/173413 A1 | 10/2017 |
| WO | WO-2017/214130 A1 | 12/2017 |
| WO | WO-2018/004517 A1 | 1/2018 |
| WO | WO-2018/035420 A1 | 2/2018 |
| WO | WO-2018/164995 A1 | 9/2018 |

OTHER PUBLICATIONS

Alexion Pharma International, "Strensiq Product Monograph," <http://alexionpharma.ca/documents/Strensiq-PM-asfotase-alfa-14Aug2015.aspx>, Prepared Aug. 14, 2015 (32 pages).

Alexion Third Quarter 2017 Earnings Call, "http://files.shareholder.com/downloads/ALXN/5636824573x0x961197/3B361D6E-80E2-463E-B0E5-3EAD7FC5B9D0/Alexion_Q3_2017_Earnings_Slides.pdf" (43 pages).

Alexion, "Highlights of Prescribing Information" for Strensiq®, 2018 (8 pages).

Ali et al., "Isolation and characterization of calcifying matrix vesicles from epiphyseal cartilage," Proc Natl Acad Sci USA. 67(3):1513-1520 (1970).

Altarescu et al., "The efficacy of enzyme replacement therapy in patients with chronic neuronopathic Gaucher's disease," J Pediatr. 138(4):539-547 (2001).

Anderson et al., "Impaired calcification around matrix vesicles of growth plate and bone in alkaline phosphatase-deficient mice," Am J Pathol. 164:841-847 (2004).

Anderson et al., "Matrix vesicles in osteomalacic hypophosphatasia bone contain apatite-like mineral crystals," Am J Pathol. 151(6):1555-61 (1997).

Anderson et al., "Pyrophosphate stimulation of calcium uptake into cultured embryonic bones. Fine structure of matrix vesicles and their role in calcification," Dev Biol. 34:211-227 (1973).

(56) References Cited

OTHER PUBLICATIONS

Anderson et al., "Sustained osteomalacia of long bones despite major improvement in other hypophosphatasia-related mineral deficits in tissue nonspecific alkaline phosphatase/nucleotide pyrophosphatase phosphodiesterase 1 double-deficient mice," Am J Pathol. 166(6):1711-1720 (2005).
Anderson et al., "The role of matrix vesicles in growth plate development and biomineralization," Front Biosci. 10:822-837 (2005).
Appeal Brief as Filed in U.S. Appl. No. 12/638,527, mailed Oct. 9, 2015 (101 pages).
Attwood, "The Babel of Bioinformatics," Genomics. 290(5491): 471-3 (2000).
Barranger et al., "Lessons learned from the development of enzyme therapy for Gaucher disease," J Inherit Metab Dis. 24(Supp 2):89-96 (2001).
Barton et al., "Replacement therapy for inherited enzyme deficiency—macrophage-targeted glucocerebrosidase for Gaucher's disease," N Engl J Med. 324(21):1464-70 (1991) (abstract only).
Beertsen et al., "Root development in mice lacking functional tissue non-specific alkaline phosphatase gene: Inhibition of acellular cementum formation," J Dent Res. 78(6):1221-1229 (1999) (10 pages).
Belachew et al., "Infantile hypophosphatasia secondary to a novel compound heterozygous mutation presenting with pyridoxine-responsive seizures," JIMD Rep. 11:17-24 (2013).
Belkhouribchia et al., "Case Report: Osteomalacia with low alkaline phosphatase: a not so rare condition with important consequences," BMJ Case Rep. doi: 10.1136/bcr-2015-212827 (2016) (4 pages).
Bennett et al., "Extracellular domain-IgG fusion proteins for three human natriuretic peptide receptors," J Biol Chem. 266(34):23060-23067 (1991).
Berkseth et al., "Clinical spectrum of hypophosphatasia diagnosed in adults," Bone. 54(1):21-7 (2013).
Bernard, "Ultrastructural localization of alkaline phosphatase in initial intramembranous osteogenesis," Clin Orthop Relat Res. 135:218-225 (1978).
Bernardi, "Chromatography of proteins on hydroxyapatite," Methods Enzymol. 27:471-9 (1973).
Bhattacharyya et al., "Hypophosphatasia and the risk of atypical femur fractures: a case-control study," BMC Muscoloskelet Disord. 17:332 (2016) (4 pages).
Bianchi, "Hypophosphatasia: an overview of the disease and its treatment," Osteoporos Int. 26(12):2743-57; DOI 10.1007/s00198-015-3272-1 (2015) (15 pages).
Bishop et al., "Transformative therapy in hypophosphatasia," Arch Dis Child. 101(6):514-5 (2016).
Bishop, "Asfotase alfa for hypophosphatasia," Horizon Scanning Centre. National Institute for Health Research. http://www.hsric.nihr.ac.uk/topics/asfotase-alfa-for-hypophosphatasia/download, retrieved Oct. 20, 2013 (9 pages).
Bishop, "Clinical management of hypophosphatasia," Clin Cases Miner Bone Metab. 12(2):170-3 (2015).
Bloch-Zupan, "Hypophosphatasia: diagnosis and clinical signs—a dental surgeon perspective," Int J Paediatr Dent. 26(6):426-438 (2016).
Bobryshev et al., "Role of bone-type tissue-nonspecific alkaline phosphatase and PHOSPO1 in vascular calcification," Curr Pharm Des. 20(37):5821-8 (2014).
Bobyr et al., "High-resolution analysis of Zn(2+) coordination in the alkaline phosphatase superfamily by EXAFS and x-ray crystallography," J Mol Biol. 415(1):102-17 (2012).
Bobé et al., "Fas-mediated liver damage in MRL hemopoietic chimeras undergoing lpr-mediated graft-versus-host disease," J Immunol. 159:4197-4204 (1997).
Bocciardi et al., "Overexpression of the C-type natriuretic peptide (CNP) is associated with overgrowth and bone anomalies in an individual with balanced t(2;7) translocation," Hum Mutat. 28(7):724-731 (2007).
Bonilla, "Pharmacokinetics of immunoglobulin administered via intravenous or subcutaneous routes," Immunol Allergy Clin N Am. 28:803-819 (2008).

Boskey et al., "Matrix vesicles promote mineralization in a gelatin gel," Calcif Tissue Int 60(3):309-15 (1997).
Boskey, "Amorphous calcium phosphate: The contention of bone," J Dent Res. 76:1433-1436 (1997).
Bowden et al., "Asfotase alfa treatment for 1 year in a 16 year-old male with severe childhood hypophosphatasia," Osteoporos Int. 29(2):511-5; DOI: 10.1007/s00198-017-4267-x (2018) (5 pages).
Braunstein, "Multiple fractures, pain, and severe disability in a patient with adult-onset hypophosphatasia," Bone Rep. 4:1-4 (2015).
Brenner et al., "Diverse biological actions of atrial natriuretic peptide," Physiol Rev. 70(3):665-699 (1990).
Briot et al., "Adult hypophosphatasia," Curr Opin Rheumatol. 28(4):448-51 (2016).
Buchet et al., "Multisystemic functions of alkaline phosphatases," Methods Mol Biol. 1053:27-51 (2013).
Byers et al., "Effect of enzyme replacement therapy on bone formation in a feline model of mucopolysaccharidosis type VI," Bone. 21(5):425-431 (1997).
Cahill et al., "Infantile hypophosphatasia: transplantation therapy trial using bone fragments and cultured osteoblasts," J. Clin Endocrinol Metab. 92(8): 2923-30 (2007).
Cameron et al., "Minireview: Natriuretic peptides during development of the fetal heart and circulation," Endocrinology. 144(6):2191-2194 (2003).
Campbell et al., "Insulin-like growth factor (IGF)-binding protein-5-(201-218) region regulates hydroxyapatite and IGF-I binding," Am J Physiol. 273:E1005-1013 (1997).
Chen et al., "Gly369Cys mutation in mouse FGFR3 causes achondroplasia by affecting both chondrogenesis and osteogenesis," J Clin Invest. 104(11):1517-1525 (1999).
Choe et al., "Substrate profiling of cysteine proteases using a combinatorial peptide library identifies functionally unique specificities," J Biol Chem. 281(18):12824-12832 (2006).
Chusho et al., "Dwarfism and early death in mice lacking C-type natriuretic peptide," Proc Natl Acad Sci USA. 98(7):4016-4021 (2001).
Ciancaglini et al., "Contribution of matrix vesicles and alkaline phosphatase to ectopic bone formation," Braz. J Med Biol Res. 39(5):603-10 (2006).
Cleland et al., "Emerging protein delivery methods," Curr Opin Biotechnol. 12:212-219 (2001).
Clemens et al., "Pharmacokinetics and biological actions of subcutaneously administered human brain natriuretic peptide," J Pharmacol Exp Ther. 287(1):67-71 (1998).
Communication from Examining Division for European Application No. EP 05 73 9065.0, dated Jun. 11, 2010 (5 pages).
Communication from Examining Division for European Application No. EP 05 73 9065.0, dated Jun. 18, 2009 (6 pages).
Communication from Examining Division for European Application No. EP 08 757 088.3, dated Apr. 20, 2011 (4 pages).
Crawley et al., "Enzyme replacement therapy in a feline model of Maroteaux-Lamy Syndrome," J Clin Invest. 97(8):1864-73 (1996).
Daggubati et al., "Adrenomedullin, endothelin, neuropeptide Y, atrial, brain, and C-natriuretic prohormone peptides compared as early heart failure indicators," Cardiovasc Res. 36:246-255 (1997).
Data Sheet for pFUSE-SEAP-hFC "Plasmid designed for the expression of a SEAP-Fc Fusion protein," Invivogen, San Diego, CA (4 pages) (1989).
De la Croix Ndong et al., "Asfotase-alpha improves bone growth, mineralization and strength in mouse models of neurofibromatosis type-1," Nat Med. 20(8):904-10 (2014) (10 pages).
De Plater et al., "The natriuretic peptide (OVCNP-39) from platypus (*Ornithorhynchus anatinus*) venom relaxes the isolated rat uterus and promotes oedema and mast cell histamine release," Toxicon. 36(3):847-857 (1998).
De Roo et al., "Infantile hypophosphatasia without bone deformities presenting with severe pyridoxine-resistant seizures," Molecular Genetics and Metabolism 111(3):404-7 (2014).
Declaration of Dr. Philippe Crine for EP 08757088.3, executed Jan. 14, 2011 (6 pages).
Deeb et al., "Could alerting physicians for low alkaline phosphatase levels be helpful in early diagnosis of hypophosphatasia?," J Clin Res Pediatr Endocrinol. 10(1):19-24 (2018).

(56) References Cited

OTHER PUBLICATIONS

Di Mauro et al., "Kinetic characterization of hypophosphatasia mutations with physiological substrates," J Bone Miner Res. 17(8):1383-91 (2002).
Dumont et al., "Monomeric Fc fusions: impact on pharmacokinetic and biological activity of protein therapeutics," BioDrugs. 20(3):151-60 (2006).
Durussel et al., "Bone mineralization-dependent craniosynostosis and craniofacial shape abnormalities in the mouse model of infantile hypophosphatasia," Dev Dyn. 245(2):175-82 (2016).
EBI Blast for Accession No. ATD17216. Entered Oct. 16, 2008 (1 page).
Eng et al., "Safety and efficacy of recombinant human alpha-galactosidase A replacement therapy in Fabry's disease," N Engl J Med. 345(1):9-16 (2001).
Engel et al., "Characterization of the hormone binding site of natriuretic peptide receptor-C," FEBS Lett. 360:169-172 (1995).
Epps, "Application No. 125513Orig1s000 Medical Review(s)," Center for Drug Evaluation and Research, <http://www.accessdata.fda.gov/drugsatfda_docs/nda/2015/125513Orig1s000MedR.pdf>, Oct. 20, 2015 (254 pages).
European Collection of Authenticated Cell Cultures (ECACC) Accession No. 85110503. Retrieved May 2, 2018 (3 pages).
European Search Report for European Patent Application No. 12842640.0, dated Mar. 13, 2015 (7 pages).
Examiner's Answer to Appeal Brief for U.S. Appl. No. 12/638,527, dated Feb. 23, 2016 (9 pages).
Extended European Search Report for European Application No. 08757088.3, dated Jun. 21, 2010 (6 pages).
Extended European Search Report for European Application No. 11774253.6, dated Oct. 14, 2013 (8 pages).
Extended European Search Report for European Application No. 18173111.8, dated Aug. 21, 2018 (9 pages).
Extended European Search Report for European Application No. EP 11 00 0196.3, dated Jun. 22, 2011 (6 pages).
Extended European Search Report for European Application No. EP 11 00 4496.3, dated Aug. 26, 2011 (7 pages).
Farley et al., "Effects of tunicamycin, mannosamine, and other inhibitors of glycoprotein processing on skeletal alkaline phosphatase in human osteoblast-like cells," Calcif Tissue Int. 76:63-74 (2005).
Farnum et al., "In vivo delivery of fluoresceinated dextrans to the murine growth plate: imaging of three vascular routes by multiphoton microscopy," available in PMC Oct. 28, 2008, published in final edited form as: Anat Rec A Discov Mol Cell Evol Biol. 288(1):91-103 (2006) (22 pages).
Fedde et al., "Alkaline phosphatase knock-out mice recapitulate the metabolic and skeletal defects of infantile hypophosphatasia," available in PMC Mar. 7, 2011, published in final edited form as: J Bone Miner Res. 14(12):2015-2026 (1999) (19 pages).
Fodor et al., "Differencial diagnosis of the low alkaline phosphatase activities," Orv Hetil. 158(26): 1003-1007 (2017) (Article in Hungarian) (English Abstract included).
Fujisaki et al., "Osteotropic Drug Delivery System (ODDS) based on bisphosphonic prodrug. IV effects of osteotropic estradiol on bone mineral density and uterine weight in ovariectomized rats," J Drug Target. 5(2):129-138 (1997) (11 pages).
Fujisawa et al., "Acidic amino acid-rich sequences as binding sites of osteonectin to hydroxyapatite crystals," Biochim Biophys Acta. 1292:53-60 (1996).
Furbish et al., "Uptake and distribution of placental glucocerebrosidase in rat hepatic cells and effects of sequential deglycosylation," Biochim Biophys Acta. 673:425-434 (1981).
Furuya et al., "Structural requirements of C-type natriuretic peptide for elevation of cyclic GMP in cultured vascular smooth muscle cells," Biochem Biophys Res Commun. 183(3):964-969 (1992).
Garg, "Investigation of the role of FcRn in the absorption, distribution, and elimination of monoclonal antibodies," Dissertation: State University of New York at Buffalo, 2007 (Abstract only) (2 pages).

Gasque et al., "Improvement of the skeletal and dental hypophosphatasia phenotype in Alpl –/– mice by administration of soluble (non-targeted) chimeric alkaline phosphatase," Available in PMC Mar. 1, 2016, published in final edited form as: Bone. 72:137-147 (2015) (25 pages).
Gates et al., "Effects of age, sex, and comorbidities on the pediatric outcomes data collection instrument (PODCI) in the general population," J Pediatr Orthop. 35(2):203-9 (2015).
Gilbert et al., "Chimeric peptides of statherin and osteopontin that bind hydroxyapatite and mediate cell adhesion," J Biol Chem. 275(21):16213-8 (2000).
Glass et al., "The infant skull: a vault of information," Radiographics. 24(2):507-22 (2004).
Graham et al., "Characteristics of a human cell line transformed by DNA from human adenovirus type 5," J Gen Virol. 36(1):59-72 (1977).
Greenberg et al., "A homoallelic $Gly^{317}$ to Asp mutation in ALPL causes the perinatal (lethal) form of hypophosphatasia in Canadian mennonites," Genomics. 17:215-217 (1993).
Guo et al., "Protein tolerance to random amino acid change," Proc Natl Acad Sci USA. 101(25):9205-9210 (2004).
Güzel Nur et al., "Pyridoxine-responsive seizures in infantile hypophosphatasia and a novel homozygous mutation in ALPL gene," J Clin Res Pediatr Endocrinol. 8(3):360-4 (2016).
Hagiwara et al., "Autocrine regulation of rat chondrocyte proliferation by natriuretic peptide C and its receptor, natriuretic peptide receptor-B," J Biol Chem. 269(14):10729-10733 (1994).
Hagiwara et al., "cGMP produced in response to ANP and CNP regulates proliferation and differentiation of osteoblastic cells," Am J Physiol. 270:C1311-C1318 (1996).
Halling Linder et al., "Glycosylation differences contribute to distinct catalytic properties among bone alkaline phosphatase isoforms," available in PMC Nov. 1, 2010, published in final edited form as: Bone. 45(5):987-993 (2009) (17 pages).
Hardy et al., "Dissection of a carboxy-terminal region of the yeast regulatory protein RAP1 with effects on both transcriptional activation and silencing," Mol Cell Biol. 12(3):1209-1217 (1992).
Harmey et al., "Concerted regulation of inorganic pyrophosphate and osteopontin by Akp2, Enpp1, and Ank," Am J Pathol. 164(4):1199-1209 (2004).
Harmey et al., "Elevated skeletal osteopontin levels contribute to the hypophosphatasia phenotype in $Akp2^{-/-}$ mice," J Bone Miner Res. 21(9):1377-1386 (2006).
Harris, "The human alkaline phosphatases: what we know and what we don't know," Clin Chim Acta. 186:133-50 (1989).
Hawrylak et al., "The solubilization of tetrameric alkaline phosphatase from human liver and its conversion into various forms by phosphatidylinositol phospholipase C or proteolysis," J Biol Chem. 263(28):14368-14373 (1988).
Henthorn et al., "Different missense mutations at the tissue-nonspecific alkaline phosphatase gene locus in autosomal recessively inherited forms of mild and severe hypophosphatasia," Proc Natl Acad Sci USA. 89:9924-9928 (1992).
Henthorn et al., "Missense mutations of the tissue-nonspecific alkaline phosphatase gene in hypophosphatasia," Clin Chem. 38(12):2501-5 (1992).
Herasse et al., "Molecular study of three cases of odontohypophosphatasia resulting from heterozygosity for mutations in the tissue non-specific alkaline phosphatase gene," J Med Genet. 40(8):605-9 (2003).
Hessle et al., "Tissue-nonspecific alkaline phosphatase and plasma cell membrane glycoprotein-1 are central antagonistic regulators of bone mineralization," Proc Natl Acad Sci USA. 99(14): 9445-9449 (2002).
Highlights of Prescribing Information for Strensiq™, Alexion Pharmaceuticals, Inc., available <http://www.alexion.com/Documents/strensiq_pi-10-2015.aspx>, 2015 (19 pages).
Hofmann et al., "Asfotase alfa: enzyme replacement for the treatment of bone disease in hypophosphatasia," Drugs Today (Barc). 52(5):271-85 (2016).
Hofmann et al., "Clinical aspects of hypophosphatasia: an update," Clinic Rev Bone Miner Metab. 11(2):60-70 (2013).

(56) References Cited

OTHER PUBLICATIONS

Hofmann et al., "Compound heterozygosity of two functional null mutations in the ALPL gene associated with deleterious neurological outcome in an infant with hypophosphatasia," Bone. 55:150-7 (2013).
Hofmann et al., "Improvement in bone manifestations and respiratory status in infants and young children with HPP treated with asfotase alfa: an update on the ENB-010-10 trial," 7th International Conference on Children's Bone Health, Jun. 27-30, Austria, Salzburg. Bone Abstracts. 4: OC18 (2015) (3 pages).
Hofmann et al., "Recombinant enzyme replacement therapy in hypophosphatasia," Subcell Biochem. 76:323-41 (2015).
Horton et al., "Achondroplasia," Lancet. 370:162-172, 2007.
Hosain et al., "Targeted delivery of antineoplastic agent to bone: biodistribution studies of technetium-99m-labeled gem-bisphosphonate conjugate of methotrexate," J Nucl Med. 37(1):105-7 (1996).
Hult et al., "Engineered enzymes for improved organic synthesis," Curr Opin Biotechnol. 14:395-400 (2003).
Hunter et al., "Modulation of crystal formation by bone phosphoproteins: structural specificity of the osteopontin-mediated inhibition of hydroxyapatite formation," Biochem J. 300:723-728 (1994).
Husain et al., "Fc site-specific labeling of immunoglobulins with calf intestinal alkaline phosphatase," Bioconjug Chem. 5(5):482-90 (1994).
Ikezawa, "Glycosylphosphatidylinositol (GPI)-anchored proteins," *Biol Pharm Bull.* 25(4):409-417 (2002).
Inoue et al., "Four functionally distinct C-type natriuretic peptides found in fish reveal evolutionary history of the natriuretic peptide system," Proc Natl Acad Sci USA. 100(17):10079-10084 (2003).
International Preliminary Report on Patentability for International Patent Application No. PCT/CA2011/050258, dated Nov. 15, 2012 (9 pages).
International Preliminary Report on Patentability for International Patent Application No. PCT/US2012/039004, dated Apr. 22, 2014 (8 pages).
International Preliminary Report on Patentability for International Patent Application No. PCT/US2012/060869, dated Apr. 22, 2014 (7 pages).
International Preliminary Report on Patentability for International Patent Application No. PCT/US2016/015366, dated Aug. 10, 2017 (10 pages).
International Search Report and Written Opinion for International Application No. PCT/US18/26868, dated Sep. 7, 2018 (30 pages).
International Search Report and Written Opinion for International Patent Application No. PCT/CA2005/000615, dated Aug. 18, 2005 (14 pages).
International Search Report and Written Opinion for International Patent Application No. PCT/CA2008/000923, dated Sep. 12, 2008 (11 pages).
International Search Report and Written Opinion for International Patent Application No. PCT/CA2011/050258, dated Jul. 29, 2011 (14 pages).
International Search Report and Written Opinion for International Patent Application No. PCT/CA2011/050807, dated Apr. 13, 2012 (18 pages).
International Search Report and Written Opinion for International Patent Application No. PCT/US2012/039004, dated Nov. 2, 2012 (22 pages).
International Search Report and Written Opinion for International Patent Application No. PCT/US2015/039973, dated Oct. 5, 2015 (12 pages).
International Search Report and Written Opinion for International Patent Application No. PCT/US2015/058498, dated Jan. 22, 2016 (12 pages).
International Search Report and Written Opinion for International Patent Application No. PCT/US2015/064003, dated Mar. 31, 2016 (13 pages).
International Search Report and Written Opinion for International Patent Application No. PCT/US2016/015366, dated Aug. 9, 2016 (14 pages).
International Search Report and Written Opinion for International Patent Application No. PCT/US2016/025721, dated Aug. 17, 2016 (18 pages).
International Search Report and Written Opinion for International Patent Application No. PCT/US2016/039595, dated Feb. 21, 2017 (16 pages).
International Search Report and Written Opinion for International Patent Application No. PCT/US2016/047166, dated Nov. 7, 2016 (15 pages).
International Search Report and Written Opinion for International Patent Application No. PCT/US2016/049983, dated Nov. 29, 2016 (12 pages).
International Search Report and Written Opinion for International Patent Application No. PCT/US2016/054013, dated Dec. 13, 2016 (19 pages).
International Search Report and Written Opinion for International Patent Application No. PCT/US2017/025590, dated Jun. 29, 2017 (18 pages).
International Search Report and Written Opinion for International Patent Application No. PCT/US2017/025618, dated Jul. 11, 2017 (22 pages).
International Search Report and Written Opinion for International Patent Application No. PCT/US2017/036133, dated Aug. 24, 2017 (10 pages).
International Search Report and Written Opinion for International Patent Application No. PCT/US2017/047527, dated Nov. 6, 2017 (10 pages).
International Search Report and Written Opinion for International Patent Application No. PCT/US2018/020859, dated Jun. 19, 2018 (14 pages).
International Search Report and Written Opinion for International Patent Application No. PCT/US2018/025206, dated Jul. 3, 2018 (25 pages).
International Search Report for International Patent Application No. PCT/US2012/060869, dated Mar. 25, 2013 (5 pages).
Invitation to Pay Additional Fees for International Patent Application No. PCT/CA2011/050807, dated Feb. 13, 2012 (2 pages).
Invitation to Pay Additional Fees for International Patent Application No. PCT/US2012/039004, dated Aug. 29, 2012 (2 pages).
Invitation to Pay Additional Fees for International Patent Application No. PCT/US2016/015366, dated Jun. 1, 2016 (7 pages).
Iqbal et al., "Recurrent Metatarsal Fractures in Postmenopausal Woman With Low Serum Alkaline Phosphatase: A Rare Diagnosis Not to Miss," J Investig Med High Impact Case Rep. 5(3):1-3 (2017).
Ishida et al., "Tissue-nonspecific alkaline phosphatase with an Asp(289)→Val mutation fails to reach the cell surface and undergoes proteasome-mediated degradation," J Biochem. 134(1):63-70 (2003).
Jansonius, "Structure, evolution and action of vitamin $B_6$-dependent enzymes," Curr Opin Struct Biol. 8:759-769 (1998).
Jin et al., "Novel analog of atrial natriuretic peptide selective for receptor-A produces increased diuresis and natriuresis in rats," J Clin Invest. 98(4):969-976 (1996).
Johnson et al., "Matrix vesicle plasma cell membrane glycoprotein-1 regulates mineralization by murine osteoblastic MC3T3 cells," J Bone Miner Res. 14(6):883-892 (1999).
Johnson et al., "Motor proficiency in children with neurofibromatosis type 1," Pediatr Phys Ther. 22(4):344-8 (2010).
Kakkis et al., "Enzyme-replacement therapy in mucopolysaccharidosis I," N Engl J Med. 344(3):182-8 (2001).
Kalra et al., "The role of C-type natriuretic peptide in cardiovascular medicine," Eur Heart J. 22:997-1007 (2001).
Kasugai et al., "Selective drug delivery system to bone: small peptide $(Asp)_6$ conjugation," J Bone Miner Res. 15(5):936-943 (2000).
Kaufmann et al., "Influence of low temperature on productivity, proteome and protein phosphorylation of CHO cells," Biotechnol Bioeng. 63(5):573-82 (1999).

(56) References Cited

OTHER PUBLICATIONS

Kishnani et al., "Biochemical and physical function outcomes in adolescents and adults with hypophosphatasia treated with asfotase alfa for up to 4 years: interim results from a phase II study," Endocrine Society's 98th Annual Meeting and Expo, Apr. 1-4, Boston, MA. Abstract OR26-3 (2016) (2 pages).
Kishnani et al., "Monitoring guidance for patients with hypophosphatasia treated with asfotase alfa," Mol Genet Metab. 122(1-2):4-17 (2017).
Kishnani et al., "OR26-3 Biochemical and Physical Function Outcomes in Adolescents and Adults with Hypophosphatasia Treated with Asfotase Alfa for up to 4 Years: Interim Results from a Phase II Study," ENDO 2016, Boston, MA, Apr. 3, 2016 (22 pages).
Kitaoka et al., "Safety and efficacy of treatment with asfotase alfa in patients with hypophosphatasia: results from a Japanese clinical trial," Clin Endocrinol (Oxf). 87(1):10-19 (epub pp. 1-10) (2017).
Kochendoerfer, "Protein & peptide drug delivery—third international conference: Minimally invasive delivery methods," Sep. 22-23, Philadelphia, PA. IDrugs. 6(11):1043-1045 (2003).
Kosnik-Infinger et al., "Enzyme replacement therapy for congenital hypophosphatasia allows for surgical treatment of related complex craniosynostosis: a case series," Neurosurg Focus. 38(5):E10 (2015) (8 pages).
Kostenuik et al., "Infrequent delivery of a long-acting PTH-Fc fusion protein has potent anabolic effects on cortical and cancellous bone," J Bone Miner Res. 22(10):1534-1547 (2007).
Kulikova et al., "Hypophosphatasia: the clinical description of 3 cases of the disease with the molecular-genetic verification of the diagnosis," Problems of Endocrinology. 61(3):37-42 (2015) (Article in Russian) (English Abstract included).
Lazdunski et al., "Structure-function relationships for some metalloalkaline phosphatases of E. coli," Eur J Biochem. 8(4):510-7 (1969).
Le Du et al., "Crystal structure of alkaline phosphatase from human placenta at 1.8 A resolution. Implication for a substrate specificity," J Biol Chem. 276(12):9158-65 (2001) (9 pages).
Lee et al., "Disturbed osteoblastic differentiation of fibrous hamartoma cell from congenital pseudarthrosis of the tibia associated with neurofibromatosis type I," Clin Orthop Surg. 3(3):230-7 (2011).
Leone et al., "Allosteric modulation of pyrophosphatase activity of rat osseous plate alkaline phosphatase by magnesium ions," Int J Biochem Cell Biol. 30:89-97 (1998).
Li et al., "Standard reference for the six-minute-walk test in healthy children aged 7 to 16 years," Am J Respir Crit Care Med. 176(2):174-80 (2007).
Linglart et al., "Hypophosphatasia," Curr Osteoporos Rep. 14(3):95-105; DOI 10.1007/s11914-016-0309-0 (2016) (11 pages).
Liu et al., "Tissue-nonspecific alkaline phosphatase deficiency causes abnormal craniofacial bone development in the Alpl(−/−) mouse model of infantile hypophosphatasia," available in PMC Oct. 1, 2015, published in final edited form as: Bone. 67:81-94 (2014) (30 pages).
Lo et al., "High level expression and secretion of Fc-X fusion proteins in mammalian cells," Protein Eng. 11(6):495-500 (1998).
López-Delgado et al., "Abnormal bone turnover in individuals with low serum alkaline phosphatase," Osteoporosis Int. 29(9):2147-2150; doi: 10.1007/s00198-018-4571-0 (Supplementary information included) (2018) (6 pages).
Madson et al., "Asfotase alfa: sustained efficacy and tolerability in children with hypophosphatasia treated for 5 years," ESPE Abstracts. 84:FC2.4 (2015) (2 pages).
Mahmood et al., "Selection of the first-time dose in humans: comparison of different approaches based on interspecies scaling of clearance," J Clin Pharmacol. 43:692-697 (2003).
Martos-Moreno et al., "Hipofosfatasia: clinical manifestations, diagnostic recommendations and therapeutic options," An Pediatr (Barc). S1695-4033(17)30223-0 (2017) (11 pages) (Article in Spanish) (English Abstract included).
Mather, "Establishment and characterization of two distinct mouse testicular epithelial cell lines," Biol Reprod. 23(1):243-52 (1980).

Matsumoto et al., "Rescue of severe infantile hypophosphatasia mice by AAV-mediated sustained expression of soluble alkaline phosphatase," Hum Gene Ther. 22(11):1355-64 (2011).
Mayer, "Microbiology and immunology on-line: Immunoglobulins: structure and function" <http://pathmicro.med.sc.edu/mayer/IgStruct2000.htm>, University of South Carolina School of Medicine, 12 pages (2009).
McKiernan et al., "Clinical and radiographic findings in adults with persistent hypophosphatasemia," J Bone Miner Res. 29(7):1651-60 (2014).
Mericq et al., "Regulation of fetal rat bone growth by C-type natriuretic peptide and cGMP," Pediatr Res. 47(2):189-193 (2000) (9 pages).
Meyer, "Can biological calcification occur in the presence of pyrophosphate?" Arch Biochem Biophys. 231:1-8 (1984).
Michigami et al., "Common mutations F310L and T1559del in the tissue-nonspecific alkaline phosphatase gene are related to distinct phenotypes in Japanese patients with hypophosphatasia," Eur J Pediatr. 164:277-282 (2005).
Millan, "Mammalian Alkaline Phosphatases," Wiley-WCH Verlag GmbH & Co., Weinheim, Germany, 1-322 (2006).
Millán et al., "Alkaline phosphatase and hypophosphatasia," Calcif Tissue Int. 98(4):398-416 (2016).
Millán et al., "Enzyme replacement therapy for murine hypophosphatasia," J Bone Miner Res. 23(6): 777-87 (2008).
Millán et al., "Hypophosphatasia—pathophysiology and treatment," available in PMC Sep. 22, 2014, published in final edited form as: Actual Osteol. 8(3):164-182 (2012) (21 pages).
Miyazawa et al., "Cyclic GMP-dependent protein kinase II plays a critical role in C-type natriuretic peptide-mediated endochondral ossification," Endocrinology. 143(9):3604-3610 (2002).
Mori et al., "Case series: odontohypophosphatasia or missed diagnosis of childhood/adult-onset hypophosphatasia?—Call for a long-term follow-up of premature loss of primary teeth," Bone Rep. 5:228-232 (2016).
Mornet et al., "Hypophosphatasia," GeneReviews. https://www.ncbi.nlm.nih.gov/books/NBK1150/, retrieved Dec. 6, 2017, initially published Nov. 20, 2007, last updated Feb. 4, 2016 (25 pages).
Mornet et al., "Identification of fifteen novel mutations in the tissue-nonspecific alkaline phosphatase (TNSALP) gene in European patients with severe hypophosphatasia," Eur J Hum Genet. 6(4):308-14 (1998).
Mornet et al., "Structural evidence for a functional role of human tissue nonspecific alkaline phosphatase in bone mineralization," J Biol Chem. 276(33):31171-8 (2001).
Mornet, "Hypophosphatasia," Metabolism. 82:142-155; DOI: 10.1016/j.metabol.2017.08.013 (2018) (30 pages).
Mornet, "Hypophosphatasia," Orphanet J Rare Dis. 2:(40) (2007) (8 pages).
Mornet, "Molecular genetics of hypophosphatasia and phenotype-genotype correlations," Subcell Biochem. 76:25-43 (2015).
Morris et al., "Immunolocalization of alkaline phosphatase in osteoblasts and matrix vesicles of human fetal bone," Bone Miner. 19:287-298 (1992).
Morrow, "Expensive new biologic helps children fight hypophosphatasia," Manag Care. 24(12) (2015) (7 pages).
Moss et al., "Association of inorganic-pyrophosphatase activity with human alkaline-phosphatase preparations," Biochem J. 102:53-57 (1967).
Murray, "Lectin-specific targeting of lysosomal enzymes to reticuloendothelial cells," Methods Enzymol. 149:25-42 (1987).
Murshed et al., "Unique coexpression in osteoblasts of broadly expressed genes accounts for the spatial restriction of ECM mineralization to bone," Genes Dev. 19:1093-1104 (2005).
Nahabet et al., "Postnatal Pancraniosynostosis in a Patient With Infantile Hypophosphatasia," Cleft Palate Craniofac J. 53(6):741-4 (2016).
Nakao et al., "The pharmacokinetics of alpha-human atrial natriuretic polypeptide in healthy subjects," Eur J Clin Pharmacol. 31:101-103 (1986).
Narisawa et al., "Abnormal vitamin B6 metabolism in alkaline phosphatase knock-out mice causes multiple abnormalities, but not the impaired bone mineralization," J Pathol. 193:125-133 (2001).

(56) References Cited

OTHER PUBLICATIONS

Narisawa et al., "Inactivation of two mouse alkaline phosphatase genes and establishment of a model of infantile hypophosphatasia," Dev Dyn. 208:432-446 (1997).
Nasu et al., "Aberrant interchain disulfide bridge of tissue-nonspecific alkaline phosphatase with an Arg433 to Cys substitution associated with severe hypophosphatasia," FEBS Journal. 273:5612-5624 (2006).
NCBI Protein Database Accession No. AAC33858. Retrieved on Apr. 16, 2013 (1 page).
NCBI Protein Database Accession No. AAF64516. Retrieved on Apr. 16, 2013 (2 pages).
NCBI Protein Database Accession No. AAH21289. Retrieved on Apr. 16, 2013 (2 pages).
NCBI Protein Database Accession No. AAH66116. Retrieved on Apr. 16, 2013 (2 pages).
NCBI Protein Database Accession No. AAH90861. Retrieved on Apr. 16, 2013 (2 pages).
NCBI Protein Database Accession No. AAI10910. Retrieved on Apr. 16, 2013 (2 pages).
NCBI Protein Database Accession No. AAI18209. Retrieved on Apr. 17, 2013 (2 pages).
NCBI Protein Database Accession No. AAI26166. Retrieved on Apr. 16, 2013 (2 pages).
NCBI Protein Database Accession No. AAN64273. Retrieved on Apr. 16, 2013 (1 page).
NCBI Protein Database Accession No. NP_000469. Retrieved on Apr. 16, 2013 (3 pages).
NCBI Protein Database Accession No. NP_001036028. Retrieved on Apr. 16, 2013 (2 pages).
NCBI Protein Database Accession No. NP_001253798.1, downloaded on Apr. 17, 2013. (2 pages).
NCBI Protein Database Accession No. NP_001622. Retrieved on Apr. 16, 2013 (3 pages).
NCBI Protein Database Accession No. NP_001623. Retrieved on Apr. 16, 2013 (3 pages).
NCBI Protein Database Accession No. NP_031457. Retrieved on Apr. 16, 2013 (3 pages).
NCBI Protein Database Accession No. NP_037191. Retrieved on Apr. 16, 2013 (3 pages).
NCBI Protein Database Accession No. NP_112603. Retrieved on Apr. 16, 2013 (3 pages).
NCBI Protein Database Accession No. NP_776412. Retrieved on Apr. 17, 2013 (2 pages).
NCBI Protein Database Accession No. NP_789828. Retrieved on Apr. 16, 2013 (3 pages).
NCBI Protein Database Accession No. P01857. Retrieved on Apr. 18, 2013 (7 pages).
NCBI Protein Database Accession No. P05186. Retrieved on Apr. 16, 2013 (19 pages).
NCBI Protein Database Accession No. P05187. Retrieved on Apr. 16, 2013 (10 pages).
NCBI Protein Database Accession No. P08289. Retrieved on Apr. 16, 2013 (5 pages).
NCBI Protein Database Accession No. P09242. Retrieved on Apr. 16, 2013 (6 pages).
NCBI Protein Database Accession No. P09487. Retrieved on Apr. 16, 2013 (4 pages).
NCBI Protein Database Accession No. P09923. Retrieved on Apr. 16, 2013 (6 pages).
NCBI Protein Database Accession No. P10696. Retrieved on Apr. 16, 2013 (7 pages).
NCBI Protein Database Accession No. Q29486. Retrieved on Apr. 16, 2013 (3 pages).
NCBI Protein Database Accession No. Q6PYX1. Retrieved on Oct. 15, 2013 (2 pages).
NCBI Protein Database Accession No. Q9N0V0. Retrieved on Apr. 16, 2013 (1 page).
NCBI Protein Database Accession No. XP_001109717. Retrieved on Apr. 17, 2013 (1 page).
Ngo et al., Computational complexity, protein structure prediction, and the levinthal paradox. *The Protein Folding Problem and Tertiary Structure Prediction*. Merz et al. (ed.), 433, 492-495 (1994).
Nishioka et al., "Enhancement of drug delivery to bone: characterization of human tissue-nonspecific alkaline phosphatase tagged with an acidic oligopeptide," Mol Genet Metab. 88:244-255 (2006).
Nosjean et al., "Human tissue non-specific alkaline phosphatases: sugar-moiety-induced enzymic and antigenic modulations and genetic aspects," Biochem J. 321:297-303 (1997).
Oda et al., "A general method for rapid purification of soluble versions of glycosylphosphatidylinositol-anchored proteins expressed in insect cells: an application for human tissue-nonspecific alkaline phosphatase," J Biochem. 126(4):694-9 (1999).
Office Action for U.S. Appl. No. 11/111,664, dated Dec. 4, 2008 (7 pages).
Office Action for U.S. Appl. No. 11/111,664, dated May 14, 2008 (8 pages).
Office Action for U.S. Appl. No. 11/111,664, dated Oct. 4, 2007 (11 pages).
Office Action for U.S. Appl. No. 11/484,870, dated Aug. 11, 2009 (15 pages).
Office Action for U.S. Appl. No. 11/484,870, dated Feb. 2, 2009 (16 pages).
Office Action for U.S. Appl. No. 11/484,870, dated Jan. 25, 2007 (15 pages).
Office Action for U.S. Appl. No. 11/484,870, dated Jul. 5, 2007 (13 pages).
Office Action for U.S. Appl. No. 11/484,870, dated Jun. 25, 2008 (16 pages).
Office Action for U.S. Appl. No. 11/484,870, dated Oct. 1, 2007 (12 pages).
Office Action for U.S. Appl. No. 12/405,920, dated Aug. 9, 2010 (7 pages).
Office Action for U.S. Appl. No. 12/405,920, dated Dec. 17, 2009 (14 pages).
Office Action for U.S. Appl. No. 12/793,517, dated Aug. 16, 2010 (9 pages).
Office Action for U.S. Appl. No. 13/071,445, dated Feb. 6, 2012 (12 pages).
Office Action for U.S. Appl. No. 13/071,445, dated May 25, 2012 (14 pages).
Official Action for Japanese Application No. 2013-544989, dated Oct. 27, 2015 (3 pages).
Official Notification and Search Report for Eurasian Patent Application No. 201291138, dated May 17, 2013 (3 pages).
Oikawa et al., "Enzyme replacement therapy on hypophosphatasia mouse model," J Inherit Metab Dis. (2013) (9 pages).
Okazaki et al., "Lethal hypophosphatasia successfully treated with enzyme replacement from day 1 after birth," Eur J Pediatr. 175(3):433-7; DOI 10.1007/s00431-015-2641-2 (2016) (5 pages).
Orimo, "Pathophysiology of hypophosphatasia and the potential role of asfotase alfa," Ther Clin Risk Manag. 12:777-86 (2016).
Orimo, "The mechanism of mineralization and the role of alkaline phosphatase in health and disease," J Nippon Med Sch. 77(1):4-12 (2010).
Padidela et al., "Enzyme-replacement therapy in life-threatening perinatal hypophosphatasia in a premature infant," Endocrine Abstracts. 33:P9 (2013) (1 page).
Padidela et al., "p. 1-118: Management of Tracheobronchomalacia During Asfotase Alfa Treatment in Infants with Perinatal-Onset Hypophosphatasia: A Case Series," European Society for Paediatric Endocrinology (ESPE), Paris, France, Sep. 10-12, 2016 (1 page).
Panesar, "Hypophosphatasia: a rare disorder," US Pharm. 42(5) (2017) (8 pages).
Park et al., "Ex vivo assessment of contractility, fatigability and alternans in isolated skeletal muscles," J Vis Exp. 69:e4198 (2012) (8 pages).
Park et al., "First Korean case of infantile hypophosphatasia with novel mutation in ALPL and literature review," Ann Clin Lab Sci. 46(3):302-7 (2016).
Patti et al., "Critical residues in the ligand-binding site of the *Staphylococcus aureus* collagen-binding adhesin (MSCRAMM)," J Biol Chem. 270(20):12005-12011 (1995).

(56) References Cited

OTHER PUBLICATIONS

Pedersen et al., "Removal of N-terminal polyhistidine tags from recombinant proteins using engineered aminopeptidases," Protein Expr Purif. 15(3):389-400 (1999).
Pfeifer et al., "Intestinal secretory defects and dwarfism in mice lacking cGMP-dependent protein kinase II," Science. 274:2082-2086 (1996).
Phillips et al., "A modified performance-oriented mobility assessment tool for assessing clinically relevant gait impairments and change in children with hypophosphatasia: development and validation," Bone Abstracts. 4 p. 136 (2015).
Phillips et al., "FRI-224: Improved activities of daily living and physical function, with decreased pain, in children with hypophosphatasia treated for three years with asfotase alfa: results from the childhood health assessment questionnaire and the pediatric outcomes data collection instrument," The Endocrine Society's 97th Annual Meeting & Expo, San Diego, California, Mar. 5-8, 2015 (1 page).
Phillips et al., "Gait assessment in children with childhood hypophosphatasia: impairments in muscle strength and physical function," The Endocrine Society's 97th Annual Meeting & Expo, Mar. 5-8, 2015, San Diego, California (2 pages).
Phillips et al., "Physical therapy management of infants and children with hypophosphatasia," Mol Genet Metab. 119(1-2):14-9 (2016).
Phillips et al., "Significantly improved muscle strength, running speed, and agility in children with hypophosphatasia treated with asfotase alfa," Endocrine Society's 97th Annual Meeting and Expo, Mar. 5-8, San Diego, CA. Abstract OR29-4 (2015) (2 pages).
Potter et al., "Natriuretic peptides, their receptors, and cyclic guanosine monophosphate-dependent signaling functions," Endocr Rev. 27(1):47-72 (2006).
Ramachandran et al., "Treatment of an anabolic bone deficiency in neurofibromatosis with bone morphogenetic proteins and its potential application for congenital pseudarthrosis of the tibia," J Bone Joint Surg Br. 91-B (Suppl. 1), Abstract 137 (2009).
Ratner, "Alexion pays big for Synageva's rare disease drug candidate," Nat Biotechnol. 33(7):679 (2015).
Remde et al., "Successful asfotase alfa treatment in an adult dialysis patient with childhood-onset hypophosphatasia," J Endoc Soc. 1(9):1188-93 (2017).
Reply Brief as Filed in U.S. Appl. No. 12/638,527, mailed Apr. 22, 2016 (4 pages).
Reply to Final Office Action for U.S. Appl. No. 13/071,445, dated Oct. 25, 2012 (14 pages).
Reply to Office Action for U.S. Appl. No. 11/111,664, dated Sep. 10, 2008 (32 pages).
Restriction Requirement for U.S. Appl. No. 12/599,679, dated Jun. 12, 2012 (5 pages).
Rezende et al., "Inorganic pyrophosphate-phosphohydrolytic activity associated with rat osseous plate alkaline phosphatase," Cell Mol Biol. 44(2):293-302 (1998).
Rockman-Greenberg, "Hypophosphatasia," Pediatr Endocrinol Rev. 10 Suppl 2:380-8 (2013) (Abstract only).
Rodriguez et al., "Respiratory mechanics in an infant with perinatal lethal hypophosphatasia treated with human recombinant enzyme replacement therapy," Pediatr Pulmonol. 47(9):917-22 (2012).
Rowe et al., "MEPE, a new gene expressed in bone marrow and tumors causing osteomalacia," Genomics. 67:54-68 (2000).
Russell et al., "Inorganic pyrophosphate in plasma in normal persons and in patients with hypophosphatasia, osteogenesis imperfecta, and other disorders of bone," J Clin Invest. 50:961-969 (1971).
Saglam et al., "Clinical and genetic findings of Turkish hypophosphatasia cases," J Clin Res Pediatr Endocrinol. 9(3):229-236 (2017).
Salih et al., "Identification of the phosphorylated sites of metabolically 32P-labeled osteopontin from cultured chicken osteoblasts," J Biol Chem. 272(21):13966-73 (1997).
Sands et al., "Enzyme replacement therapy for murine mucopolysaccharidosis type VII," J Clin Invest. 93(6):2324-31 (1994).
Saraff et al., "A diagnostic algorithm for children with low alkaline phosphatase activities: lessons learned from laboratory screening for hypophosphatasia," J Pediatr. 172:181-6 (2016) (7 pages).
Sather, "008-case study: 3 year old female with hypophosphatasia, treated with asfotase alfa replacement," Journal of Pediatric Nursing. 34:104 (2017).
Sawai et al., "Severe perinatal hypophosphatasia due to homozygous deletion of T at nucleotide 1559 in the tissue nonspecific alkaline phosphatase gene,". Prenat Diagn. 23(9):743-6 (2003).
Schindeler et al., "Modeling bone morphogenetic protein and bisphosphonate combination therapy in wild-type and Nf1 haploinsufficient mice," J Orthop Res. 26(1):65-74 (2008).
Schmidt et al., "Clinical, radiographic and biochemical characteristics of adult hypophosphatasia," Osteoporos Int. 28(9):2653-2662 (2017).
Schmidt et al., "Hypophosphatasia: What is currently available for treatment?" Internist (Berl). 57(12):1145-1154 (2016) (Article in German) (English abstract).
Scott, "Asfotase alfa in perinatal/infantile-onset and juvenile-onset hypophosphatasia: a guide to its use in the USA," BioDrugs. 30(1):41-8 (2016).
Scott, "Asfotase alfa: a review in paediatric-onset hypophosphatasia," Drugs. 76(2):255-62 (2016).
Seefried et al., "Pharmacodynamic results from a phase 2a, randomized, multicenter, open-label, dose-ranging study of asfotase alfa in adults with pediatric hypophosphatasia," 100th Annual Meeting and Expo of the Endocrine Society, Mar. 17-20, 2018, Chicago, IL. (1 page).
Sekido et al., "Novel drug delivery system to bone using acidic oligopeptide: pharmacokinetic characteristics and pharmacological potential," J Drug Target. 9(2):111-21 (2001).
Shapiro et al., "Hypophosphatasia in adults: clinical assessment and treatment considerations," J Bone Miner Res. 32(10):1977-1980 (2017).
Sharom et al., "Glycosylphosphatidylinositol-anchored proteins: structure, function, and cleavage by phosphatidylinositol-specific phospholipase C," Biochem Cell Biol. 80:535-549 (2002).
Sheikh et al., "A newborn with no bones: neonatal hypophosphatasia with respiratory distress," J Pediatr. 188:306 (2017).
Shukla et al., "RNA interference and inhibition of MEK-ERK signaling prevent abnormal skeletal phenotypes in a mouse model of craniosynostosis," Nat Genet. 39(9):1145-1150 (2007).
Shull et al., "Enzyme replacement in a canine model of Hurler syndrome," Proc Natl Acad Sci USA. 91:12937-12941 (1994).
Siller et al., "Alkaline phosphatase: discovery and naming of our favorite enzyme," J Bone Miner Res. 33(2):362-4 (2018).
Simm et al., "Successful use of enzyme replacement therapy in infantile hypophosphatasia," J Paediatr Child Health. 53(9):925-926 (2017).
Siris et al., "Paget's disease of bone," Trends Endocrinol Metab. 2(6):207-12 (1991).
Skolnick et al., "From genes to protein structure and function: novel applications of computational approaches in the genomic era," Trends Biotechnol. 18(1):34-9 (2000).
Sotillo et al., "Signs and symptoms of hypophosphatasia," Dimensions of Dental Hygiene. 15(4):44-47 (2017) (6 pages).
Spears et al., "Deoxyuridylate effects on thymidylate synthase-5-fluorodeoxyuridylate-folate ternary complex formation," Biochem Pharmacol. 38(18):2985-2993 (1989).
Spentchian et al., "Severe hypophosphatasia: characterization of fifteen novel mutations in the ALPL gene," Hum Mutat. 22(1) (2003) (5 pages).
Srinivas et al., "Assessment of dose proportionality, absolute bioavailability, and immunogenicity response of CTLA4Ig (BMS-188667), a novel immunosuppressive agent, following subcutaneous and intravenous administration to rats," Pharmaceutical Res. 14(7):911-916 (1997).
Stahl et al., "Evidence for receptor-mediated binding of glycoproteins, glycoconjugates, and lysosomal glycosidases by alveolar macrophages," Proc Natl Acad Sci USA. 75(3):1399-1403 (1978).
Stec et al., "A revised mechanism for the alkaline phosphatase reaction involving three metal ions," J Mol Biol. 299(5):1303-11 (2000).

(56) References Cited

OTHER PUBLICATIONS

Sturtz et al., "A study of the delivery-targeting concept applied to antineoplasic drugs active on human osteosarcoma. I. Synthesis and biological activity in nude mice carrying human osteosarcoma xenografts of gem-bisphosphonic methotrexate analogues," Eur J Med Chemistry. 27:825-33 (1992).

Suda et al., "C-type natriuretic peptide as an autocrine/paracrine regulator of osteoblast: evidence for possible presence of bone natriuretic peptide system," Biochem Biophys Res Commun. 223:1-6 (1996).

Sugano et al., "Successful gene therapy in utero for lethal murine hypophosphatasia," Hum Gene Ther. 23(4):399-406 (2012).

Supplementary European Search Report for European Application No. EP 05 73 9065 (date of completion of search Nov. 7, 2008, dated Dec. 2, 2008) (3 pages).

Supplementary European Search Report for European Patent Application No. 11853820.6, dated Mar. 25, 2014 (3 pages).

Symersky et al., "Structure of the collagen-binding domain from a *Staphylococcus aureus* adhesin," Nat Struct Biol. 4(10):833-838 (1997).

Takahashi et al., "Parental serum alkaline phosphatase activity as an auxiliary tool for prenatal diagnosis of hypophosphatasia," Prenat Diagn. 37(5):491-6 (2017).

Takano et al., "Molecular evolution of shark C-type natriuretic peptides," Zoolog Sci. 11:451-454 (1994).

Taketani et al., "Clinical and genetic aspects of hypophosphatasia in Japanese patients," Arch Dis Child. 99(3):211-5 (2014) (6 pages).

Taketani et al., "Ex vivo expanded allogeneic mesenchymal stem cells with bone marrow transplantation improved osteogenesis in infants with severe hypophosphatasia," Cell Transplant. 24(10):1931-43 (2015).

Takinami et al., "The mutant (F310L and V365I) tissue-nonspecific alkaline phosphatase gene from hypophosphatasia," J Med Dent Sci. 51(1):67-74 (2004).

Tamura et al., "Critical roles of the guanylyl cyclase B receptor in endochondral ossification and development of female reproductive organs," Proc Natl Acad Sci USA. 101(49):17300-17305 (2004).

Teixeira et al., "Nitric oxide, C-type natriuretic peptide and cGMP as regulators of endochondral ossification," Dev Biol. 319:171-178 (2008).

Tenorio et al., "Molecular and clinical analysis of ALPL in a cohort of patients with suspicion of hypophosphatasia," Am J Med Genet A. 173(3):601-10 (2017).

Tomatsu, Declaration Under 37 C.F.R. § 1.132 for U.S. Appl. No. 11/484,870, dated Jun. 1, 2009 (3 pages).

Tomatsu, Declaration Under 37 C.F.R. § 1.132 for U.S. Appl. No. 11/484,870, dated Nov. 27, 2007 (2 pages).

Tomazos et al., "Determination of the Minimal Clinically Important Difference in the Six-Minute Walk Test for Patients with Hypophosphatasia," European Society for Paediatric Endocrinology, 55th Annual ESPE, Paris, France, Sep. 10-12, 2016, <http://abstracts.eurospe.org/hrp/0086/hrp0086FC2.5.htm>, (4 pages).

Tsiantouli et al., "Hypophosphatasia," Rev Med Suisse. 13(559):855-8 (2017) (Article in French) (English Abstract Included).

Tsuji et al., "A loss-of-function mutation in natriuretic peptide receptor 2 (Npr2) gene is responsible for disproportionate dwarfism in cn/cn mouse," J Biol Chem. 280(14):14288-14292 (2005).

Tye et al., "Delineation of the hydroxyapatite-nucleating domains of bone sialoprotein," J Biol Chem. 278(10):7949-7955 (2003).

Uludag et al., "Bone affinity of a bisphosphonate-conjugated protein in vivo," Biotechnol Prog. 16(6):1115-8 (2000).

UniProtKB Accession No. P01857. Retrieved May 2, 2018 (13 pages).

UniProtKB Accession No. P05186. Retrieved May 2, 2018 (19 pages).

Urlaub et al., "Deletion of the diploid dihydrofolate reductase locus from cultured mammalian cells," Cell. 33:405-412 (1983).

Urlaub et al., "Isolation of Chinese hamster cell mutants deficient in dihydrofolate reductase activity," Proc Natl Acad Sci U S A. 77(7):4216-20 (1980).

Wang et al., "A mouse model for achondroplasia produced by targeting fibroblast growth factor receptor 3," Proc Natl Acad Sci USA. 96:4455-4460 (1999).

Wang et al., "Current concepts in odontohypophosphatasia form of hypophosphatasia and report of two cases," BMC Oral Health. 16(1):70 (2016) (8 pages).

Wang et al., "Mice lacking Nf1 in osteochondroprogenitor cells display skeletal dysplasia similar to patients with neurofibromatosis type 1," Hum Mol Genet. 20(20):3910-3924 (2011).

Wang et al., "Structure-based chemical modification strategy for enzyme replacement treatment of phenylketonuria," Mol Genet Metab. 86:134-140 (2005).

Waymire et al., "Mice lacking tissue non-specific alkaline phosphatase die from seizures due to defective metabolism of vitamin B-6," Nat Genet. 11(1):45-51 (1995).

Weber et al., "Burden of disease in adult patients with hypophosphatasia: Results from two patient-reported surveys," Metabolism. 65(10):1522-30 (2016).

Weinberg, "An overview of infliximab, etanercept, efalizumab, and alefacept as biologic therapy for psoriasis," Clin Ther. 25(10):2487-505 (2003).

Weiss et al., "A missense mutation in the human liver/bone/kidney alkaline phosphatase gene causing a lethal form of hypophosphatasia," Proc Natl Acad Sci USA. 85:7666-7669 (1988).

Weiss et al., "Isolation and characterization of a cDNA encoding a human liver/bone/kidney-type alkaline phosphatase," Proc Natl Acad Sci USA. 83(19):7182-6 (1986) (6 pages).

Weiss et al., "Structure of the human liver/bone/kidney alkaline phosphatase gene," J Biol Chem. 263(24):12002-10 (1988).

Weninger et al., "Biochemical and morphological effects of human hepatic alkaline phosphatase in a neonate with hypophosphatasia," Acta Paediatr Scand. Suppl. 360:154-160 (1989).

Whyte et al., "Alkaline phosphatase: placental and tissue-nonspecific isoenzymes hydrolyze phosphoethanolamine, inorganic pyrophosphate, and pyridoxal 5'-phosphate. Substrate accumulation in carriers of hypophosphatasia corrects during pregnancy," J Clin Invest. 95(4):1440-5 (1995).

Whyte et al., "Asfotase alfa therapy for children with hypophosphatasia," JCI Insight. 1(9):e85971 (2016) (11 pages).

Whyte et al., "Asfotase alfa treatment improves survival for perinatal and infantile hypophosphatasia," J Clin Endocrinol Metab. 101(1):334-42 (2016) (17 pages).

Whyte et al., "Enzyme replacement therapy for infantile hypophosphatasia attempted by intravenous infusions of alkaline phosphatase-rich Paget plasma: results in three additional patients," J Pediatr. 105(6):926-33 (1984).

Whyte et al., "Enzyme-replacement therapy in life-threatening hypophosphatasia," N Engl J Med. 366(10):904-13 (2012).

Whyte et al., "Hypophosphatasia: Enzyme replacement therapy (asfotase alfa) decreases TNSALP substrate accumulation and improves functional outcomes in affected adolescents and adults," Bull Group Int Rech Sci Stomatol Odontol. 51 (1):35 (2012).

Whyte et al., "Hypophosphatasia: natural history study of 101 affected children investigated at one research center," Bone. 93:125-138 (2016).

Whyte et al., "Hypophosphatasia: validation and expansion of the clinical nosology for children from 25 years experience with 173 pediatric patients," Bone. 75:229-39 (2015).

Whyte et al., "Infantile hypophosphatasia: enzyme replacement therapy by intravenous infusion of alkaline phosphatase-rich plasma from patients with Paget bone disease," J Pediatr. 101(3):379-86 (1982).

Whyte et al., "Infantile hypophosphatasia: normalization of circulating bone alkaline phosphatase activity followed by skeletal remineralization. Evidence for an intact structural gene for tissue nonspecific alkaline phosphatase," J Pediatr. 108(1):82-8 (1986).

Whyte et al., "Markedly increased circulating pyridoxal-5'-phosphate levels in hypophosphatasia," J Clin Invest. 76:752-756 (1985).

Whyte et al., "Marrow cell transplantation for infantile hypophosphatasia," J Bone Miner Res. 18(4):624-36 (2003).

(56) References Cited

OTHER PUBLICATIONS

Whyte, "Heritable Forms of Rickets and Osteomalacia," in Connective Tissues and Its Heritable Disorders, pp. 765-787, 2002 (eds. R.M. Royce and B. Steinmann, Wiley-Liss, Inc. Hoboken).

Whyte, "Hypophosphatasia—aetiology, nosology, pathogenesis, diagnosis and treatment," Nat Rev Endocrinol. 12(4):233-46 (2016).

Whyte, "Hypophosphatasia and the role of alkaline phosphatase in skeletal mineralization," Endocr Rev. 15(4):439-461 (1994).

Whyte, "Hypophosphatasia," in The Metabolic and Molecular Bases of Inherited Disease (8th ed.), pp. 5313-5329, 2001 (McGraw-Hill Book Company) (epub pp. 1-41).

Whyte, "Hypophosphatasia: an overview for 2017," Bone. 102:15-25 (2017).

Whyte, "Hypophosphatasia: enzyme replacement therapy brings new opportunities and new challenges," J Bone Miner Res. 32(4):667-675 (2017).

Whyte, "Hypophosphatasia: Nature's window on alkaline phosphatase function in man," *Principles of Bone Biology*, 2nd ed., Bilezikian, Raisz, and Rodan. 2:1229-1248 (2002).

Whyte, "Physiological role of alkaline phosphatase explored in hypophosphatasia," Ann N Y Acad Sci. 1192:190-200 (2010).

Wickramasinghe et al., "A case of hypophosphatasia," Ceylon Med J. 48(3):94-5 (2003).

Williams et al., "Solute transport in growth plate cartilage: In vitro and in vivo," Biophys J. 93(3):1039-1050 (2007).

Wroblewski et al., "Pharmacokinetics, metabolic stability, and subcutaneous bioavailability of a genetically engineered analog of DcR3, flint [DcR3(R218Q)], in cynomolgus monkeys and mice," Drug Metab Dispos. 31(4):502-507 (2003).

Yadav et al., "Dose response of bone-targeted enzyme replacement for murine hypophosphatasia," available in PMC Aug. 1, 2012, published in final edited form as: Bone. 49(2):250-6 (2011) (20 pages).

Yamamoto et al., "A successful treatment with pyridoxal phosphate for West syndrome in hypophosphatasia," Pediatr Neurol. 30(3):216-8 (2004).

Yamamoto et al., "Long term phenotypic correction of severe infantile hypophosphatasia in a mouse model by neonatal injection of lentiviral vector," Mol Ther. 17:S67-S68, Abstract 171 (2009).

Yamamoto et al., "Prolonged survival and phenotypic correction of Akp2(−/−) hypophosphatasia mice by lentiviral gene therapy," J Bone Miner Res. 26(1):135-42 (2011).

Yasoda et al., "Natriuretic peptide regulation of endochondral ossification. Evidence for possible roles of the C-type natriuretic peptide/guanylyl cyclase-B pathway," J Biol Chem. 273(19):11695-11700 (1998).

Yasoda et al., "Overexpression of CNP in chondrocytes rescues achondroplasia through a MAPK-dependent pathway," Nat Med. 10(1):80-86 (2004).

Yasoda et al., "Systemic administration of C-type natriuretic peptide as a novel therapeutic strategy for skeletal dysplasias," Endocrinology. 150(7):3138-3144 (2009).

Yoder et al., "Reduced ability of C-type natriuretic peptide (CNP) to activate natriuretic peptide receptor B (NPR-B) causes dwarfism in lbab −/− mice," Peptides. 29(9):1575-1581 (2008).

Yokogawa et al., "Selective delivery of estradiol to bone by aspartic acid oligopeptide and its effects on ovariectomized mice," Endocrinology. 142(3):1228-1233 (2001).

Young et al., "Structure, expression, and regulation of the major noncollagenous matrix proteins of bone," Clin Orthop Relat Res. 281:275-294 (1992).

Zierhut et al., "Population PK-PD model for Fc-osteoprotegerin in healthy postmenopausal women," J Pharmacokinet Pharmacodyn. 35:379-399 (2008).

Zurutuza et al., "Correlations of genotype and phenotype in hypophosphatasia," Hum Mol Genet. 8(6):1039-1046 (1999).

"Sequence 4," SCORE Search Results for U.S. Appl. No. 12/599,679, retrieved Nov. 17, 2018 (2 pages).

Abrams et al., "Calcium and Vitamin D Requirements of Enterally Fed Preterm Infants," Pediatrics. 131(5): e1676-e1683 (2013) (9 pages).

Agochukwu et al., "Hearing loss in syndromic craniosynostoses: Introduction and consideration of mechanisms," available in PMC Aug. 13, 2014, published in final edited form as: Am J Audiol. 23(2):135-41 (2014) (13 pages).

Anderson, "Mechanism of Mineral Formation in Bone," *Pathology Reviews*. Emanuel Rubin and Ivan Damjanov (eds.), 13-23 (1990).

Balasubramaniam et al., "Perinatal hypophosphatasia presenting as neonatal epileptic encephalopathy with abnormal neurotransmitter metabolism secondary to reduced co-factor pyridoxal-5'-phosphate availability," J Inherit Metab Dis. 33(Suppl 3):S25-33 (2010).

Barcia et al., "Infantile hypophosphatasia: treatment options to control hypercalcemia, hypercalciuria, and chronic bone demineralization," J Pediatr. 130(5):825-8 (1997).

Barvencik et al., "Skeletal mineralization defects in adult hypophosphatasia—a clinical and histological analysis," Osteoporosis Int. 22(10):2667-75 (2011).

Baumgartner-Sigl et al., "Pyridoxine-responsive seizures as the first symptom of infantile hypophosphatasia caused by two novel missense mutations (c.677T>C, p. M226T; c.1112C>T, p. T371I) of the tissue-nonspecific alkaline phosphatase gene," Bone. 40(6):1655-61 (2007).

Beck et al., "Whole-body MRI in the childhood form of hypophosphatasia," Rheumatol Int. 31(10):1315-20 (2011).

Beederman et al., "Molecular basis of cranial suture biology and disease: osteoblastic and osteoclastic perspectives," Genes Dis. 1(1):120-5 (2014).

Boulet et al., "A population-based study of craniosynostosis in metropolitan Atlanta, 1989-2003," Am J Med Genet A. 146A(8): 984-91 (2008).

Carden et al., "Tracheomalacia and tracheobronchomalacia in children and adults: an in-depth review," Chest. 127(3):984-1005 (2005).

Chan et al., "Endoscope-assisted versus open repair of craniosynostosis: a comparison of perioperative cost and risk," J Craniofac Surg. 24(1):170-4 (2013).

Choi et al., "Craniosynostosis in growing children: pathophysiological changes and neurosurgical problems," J Korean Neurosurg Soc. 59(3):197-203 (2016).

Chong et al., "Minimally invasive suturectomy and postoperative helmet therapy: advantages and limitations," J Korean Neurosurg Soc. 59(3):227-32 (2016).

Clarke, "Normal bone anatomy and physiology," Clin J Am Soc Nephrol. 3(Suppl 3):S131-9 (2008).

Colantonio et al., "Closing the gaps in pediatric laboratory reference intervals: a CALIPER database of 40 biochemical markers in a healthy and multiethnic population of children," Clin Chem. 58(5):854-68 (2012).

Collmann et al., "Neurosurgical aspects of childhood hypophosphatasia," Childs Nerv Syst. 25(2):217-23 (2009).

Communication pursuant to Rule 164(2)(b) and Article 94(3) EPC for European Patent Application No. 16707571.2, dated Feb. 26, 2019 (12 pages).

Czerwinski et al., "Major morbidity and mortality rates in craniofacial surgery: an analysis of 8101 major procedures," Plast Reconstr Surg. 126(1):181-6 (2010).

Del Angel et al., "Birth prevalence estimation of severe Hypophosphatasia in European populations using large-scale protein-coding genetic variation databases," American Society of Human Genetics 66th Annual Meeting, Oct. 18-22, Vancouver, Canada. Poster abstract 1670T (2016) (2 pages).

Di Rocco et al., "Craniosynostosis and hypophosphatasia," Arch Pediatr. 24(5S2):5S89-5S92 (2017).

Dortschy et al., "Bevölkerungsbezogene verteilungswerte ausgewählter laborparameter aus der studie zur gesundheit von kindern und jugendlichen in Deutschland (KiGGS)," Gesundheitsberichterstattung des Bundes, Robert Koch Institute (2009) (136 pages).

Eade et al., "Pyrophosphate arthropathy in hypophosphatasia," Ann Rheum Dis. 40(2):164-70 (1981).

(56) References Cited

OTHER PUBLICATIONS

Esparza et al., "Complications in the surgical treatment of craniosynostosis and craniofacial syndromes: apropos of 306 transcranial procedures," Childs Nerv Syst. 24(12):1421-30 (2008).
Esparza et al., "Surgical treatment of isolated and syndromic craniosynostosis. Results and complications in 283 consecutive cases," Neurocirugía. 19(6):509-29 (2008).
Fong et al., "Hypocalcemia: Updates in diagnosis and management for primary care," Can Fam Physician. 58(2):158-62 (2012).
Fraser, "Hypophosphatasia," Am J Med. 22(5):730-46 (1957).
Garber et al., "Comparing outcomes and cost of 3 surgical treatments for sagittal synostosis: a retrospective study including procedure-related cost analysis," Neurosurgery. 81(4):680-7 (2017).
Ginelliová et al., "Sudden death associated with syndromic craniosynostosis," Forensic Sci Med Pathol. 12(4):506-9 (2016).
Greenwood et al., "Familial incidence and associated symptoms in a population of individuals with nonsyndromic craniosynostosis," Genet Med. 16(4):302-10 (2014).
Guañabens et al., "Calcific periarthritis as the only clinical manifestation of hypophosphatasia in middle-aged sisters," J Bone Miner Res. 29(4):929-34 (2014).
Hancarova et al., "Hypophosphatasia due to uniparental disomy," Bone. 81:765-766 (2015).
Herring, "Mechanical influences on suture development and patency," Front Oral Biol. 12:41-56 (2008).
Hollis et al., "Current concepts in hypophosphatasia: case report and literature review," Int J Paediatr Dent. 23(3):153-9 (2013).
Hwang et al., "Update of diagnostic evaluation of craniosynostosis with a focus on pediatric systematic evaluation and genetic studies," J Korean Neurosurg Soc. 59(3):214-8 (2016).
International Preliminary Report on Patentability for International Patent Application No. PCT/US2016/049983, dated Sep. 11, 2018 (9 pages).
International Search Report and Written Opinion for International Application No. PCT/US2019/045963, dated Jan. 30, 2020 (26 pages).
Johnson et al., "Craniosynostosis," Eur J Hum Genet. 19(4):369-76 (2011).
Kabbani et al., "Craniosynostosis," Am Fam Physician. 69(12):2863-70 (2004).
Kajdic et al., "Craniosynostosis—Recognition, clinical characteristics, and treatment," Bosn J Basic Med Sci. 18(2):110-6 (2018).
Katsianou et al., "Signaling mechanisms implicated in cranial sutures pathophysiology: Craniosynostosis," BBA Clin. 6:165-76 (2016).
Khanna et al., "Pictorial essay: the many faces of craniosynostosis," Indian J Radiol Imaging. 21(1):49-56 (2011).
Kim et al., "Craniosynostosis: Updates in radiologic diagnosis," J Korean Neurosurg Soc. 59(3):219-26 (2016).
Kozlowski et al., "Hypophosphatasia. Review of 24 Cases," Pediatr Radiol. 5(2):103-17 (1976) (15 pages).
Krakow et al., "Clinical and radiographic delineation of bent bone dysplasia-FGFR2 type or bent bone dysplasia with distinctive clavicles and angel-shaped phalanges," Am J Med Genet A. 170(10):2652-61 (2016).
Leung et al., "Outcome of perinatal hypophosphatasia in Manitoba Mennonites: a retrospective cohort analysis," JIMD Rep. 11:73-78 (2013).
Li et al., "Timing of the initiation of bisphosphonates after surgery for fracture healing: a systematic review and meta-analysis of randomized controlled trials," Osteoporos Int. 26(2):431-41 (2015) (11 pages).
Makras et al., "Medical treatment of Hypercalcaemia," Hormones. 8(2):83-95 (2009).
Mathijssen, "Guideline for care of patients with the diagnoses of craniosynostosis: working group on craniosynostosis," J Craniofac Surg. 26(6):1735-807 (2015).
Merrill et al., "Bent bone dysplasia-FGFR2 type, a distinct skeletal disorder, has deficient canonical FGF signaling," Am J Hum Genet. 90(3):550-7 (2012).

Miller et al., "Ultrasound diagnosis of craniosynostosis," Cleft Palate Craniofac J. 39(1):73-80 (2002).
Millichap, "Cognitive Development of Children with Craniosynostosis," Pediatr Neurol Briefs. 29(6):47 (2015).
Millán, "The role of phosphatases in the initiation of skeletal mineralization," Calcif Tissue Int. 93(4):299-306 (2013).
Mohn et al., "Hypophosphatasia in a child with widened anterior fontanelle: lessons learned from late diagnosis and incorrect treatment," Acta Paediatr. 100(7):e43-6 (2011).
Mornet et al., "A molecular-based estimation of the prevalence of hypophosphatasia in the European population," Ann Hum Genet. 75(3):439-45 (2011).
Mornet, "Hypophosphatasia," Best Pract Res Clin Rheumatol. 22(1):113-27 (2008).
Mornet, "The tissue nonspecific alkaline phosphatase gene mutations database," <www.sesep.uvsq.fr/03_hypo_mutations.php>, last updated Nov. 28, 2019 (14 pages).
Morrison et al., "Mitigation of tracheobronchomalacia with 3D-printed personalized medical devices in pediatric patients," available in PMC Apr. 29, 2016, published in final edited form as: Sci Transl Med. 7(285):285ra264 (2015) (23 pages).
Murgu et al., "Tracheobronchomalacia and excessive dynamic airway collapse," Respirology. 11(4):388-406 (2006).
Nakamura-Utsunomiya et al., "Clinical characteristics of perinatal lethal hypophosphatasia: a report of 6 cases," Clin Pediatr Endocrinol. 19(1):7-13 (2010).
Official Action and Translation for Japanese Application No. 2017-539393, dated Sep. 17, 2019 (14 pages).
Oginni et al., "Radiological and biochemical resolution of nutritional rickets with calcium," Arch Dis Child. 88(9):812-17 (2003).
Opperman, "Cranial sutures as intramembranous bone growth sites," Dev Dyn. 219(4):472-85 (2000).
Park et al., "The effect of alendronate loaded biphasic calcium phosphate scaffolds on bone regeneration in a rat tibial defect model," Int J Mol Sci. 16(11):26738-53 (2015) (17 pages).
Reginato et al., "Musculoskeletal manifestations of osteomalacia and rickets," Best Pract Res Clin Rheumatol. 17(6):1063-80 (2003).
Rockman-Greenberg et al., "Hypophosphatasia: Enzyme Replacement with ENB-0040, a Bone-Targeted Human Recombinant Tissue Nonspecific Alkaline Phosphatase (TNSALP) Fusion Protein," American College of Medical Genetics, 16th Annual Clinical Genetics Meeting, Mar. 25-29, Tampa, Florida (2009) (1 page).
Rodgers et al., "Spring-assisted cranioplasty for the correction of non-syndromic scaphocephaly: a quantitative analysis of 100 consecutive cases," Plast Reconstr Surg. 140(1):125-34 (2017).
Rodionova et al., "Hypophosphatasia in adults: clinical cases and literature review," Osteoporosis and Bone Diseases. 18(2):25-7 (2015) (4 pages).
Rottgers et al., "Outcomes of endoscopic suturectomy with post-operative helmet therapy in bilateral coronal craniosynostosis," J Neurosurg Pediatr. 18(3):281-6 (2016).
Rozovsky et al., "Cranial ultrasound as a first-line imaging examination for craniosynostosis," Pediatrics. 137(2):e20152230 (2016) (9 pages).
Sabbagh et al., "Hypophosphatemia leads to rickets by impairing caspase-mediated apoptosis of hypertrophic chondrocytes," Proc Natl Acad Sci U S A. 102(27):9637-42 (2005).
Sakamoto et al., "Physiological changes and clinical implications of syndromic craniosynostosis," J Korean Neurosurg Soc. 59(3):204-13 (2016).
Salva et al., "Signaling networks in joint development," Dev Dyn. 246(4):262-74 (2017).
Search Report and Translation for Russian Application No. 2018109368, dated Feb. 5, 2020 (4 pages).
Seshia et al., "Myopathy with hypophosphatasia," Arch Dis Child. 65(1):130-1 (1990).
Shah et al., "Sudden infant death in a patient with FGFR3 P250R mutation," Am J Med Genet A. 140A(24):2794-6 (2006).
Sharma et al., "Bilateral femoral neck fractures in a young patient suffering from hypophosphatasia, due to a first time epileptic seizure," J Orthop Case Rep. 5(3):66-8 (2015).
Sharma, "Craniosynostosis," Indian J Plast Surg. 46(1):18-27 (2013).

(56) References Cited

OTHER PUBLICATIONS

Silver et al., "Pulmonary hypoplasia in neonatal hypophosphatasia," Pediatr Pathol. 8(5):483-93 (1988) (12 pages).
Simmons, "Best Practices In: Recognizing and Diagnosing Hypophosphatasia," Clinical Endocrinology News. <www.mdedge.com/sites/default/files/issues/articles/Alexion_10_11_Final_Web.pdf>, published Sep. 30, 2013, retrieved on Mar. 27, 2019 (8 pages).
Stoll et al., "Severe hypophosphatasia due to mutations in the tissue-nonspecific alkaline phosphatase (TNSALP) gene," Genet Couns. 13(3):289-95 (2002).
Taketani et al., Chapter 9: Hypophosphatasia. *Human Pathobiochemistry*. T. Oohashi et al. (eds.), 91-100 (2019).
Thacher et al., "Radiographic scoring method for the assessment of the severity of nutritional rickets," J Trop Pediatr. 46(3):132-9 (2000).
Thurner et al., "Osteopontin deficiency increases bone fragility but preserves bone mass," Bone. 46(6):1564-73 (2010).
Tokumaru et al., "Skull base and calvarial deformities: association with intracranial changes in craniofacial syndromes," Am J Neuroradiol. 17(4):619-30 (1996).
Wang et al., "The effects of tissue-non-specific alkaline phosphatase gene therapy on craniosynostosis and craniofacial morphology in the FGFR2C342Y/+ mouse model of Crouzon craniosynostosis," Orthod Craniofac Res. 18 Suppl 1:196-206 (2015).
Watanabe et al., "Prevalence of c.1559delT in ALPL, a common mutation resulting in the perinatal (lethal) form of hypophosphatasia in Japanese and effects of the mutation on heterozygous carriers," J Hum Genet. 56(2):166-8 (2011).
Weber et al., "Burden of disease in children with hypophosphatasia: results from patient-reported surveys," 7th International Conference on Children's Bone Health, Jun. 27-30, Salzburg, Austria. *Bone Abstracts*. 4: p. 119 (2015) (3 pages).
Whyte et al., "A retrospective, multi-national, non-interventional, natural history study of the childhood form of hypophosphatasia," ENDO 2015: The Endocrine Society Annual Meeting, Mar. 5-8, San Diego, California. Abstract LB-OR01-4 (2015) (2 pages).
Whyte et al., "Adult hypophosphatasia treated with teriparatide," J Clin Endocrinol Metab. 92(4):1203-8 (2007).
Whyte et al., "Adult hypophosphatasia with chondrocalcinosis and arthropathy: variable penetrance of hypophosphatasemia in a large Oklahoma kindred," Am J Med. 72(4):631-41 (1982).
Whyte et al., "Asfotase alfa for infants and young children with hypophosphatasia: 7 year outcomes of a single-arm, open-label, phase 2 extension trial," Lancet Diabetes Endocrinol. 7(2):93-105 (2019) (52 pages).
Whyte et al., "Asfotase alfa: Sustained Efficacy and Tolerability in Infants and Young Children with Life-Threatening Hypophosphatasia," 2014 Pediatric Academic Societies and Asian Society for Pediatric Research Joint Meeting, May 3-6, Vancouver, BC, Canada. Poster 69 (2014) (1 page).
Whyte et al., "Hypophosphatasia (HPP) in children: enzyme replacement therapy (EzRT) using bone-targeted, tissue-nonspecific alkaline phosphatase (TNSALP)," Ann Neurol. 68(Suppl 14):S70 Abstract WIP-28 (2010) (1 page).
Whyte et al., "Hypophosphatasia: A Retrospective Natural History Study of the Severe Perinatal and Infantile Forms," 2014 European Calcified Tissue Society Congress, May 17-20, Prague, Czech Republic. Poster p. 364 (2014) (1 page).
Whyte et al., "Natural history of perinatal and infantile hypophosphatasia: a retrospective study," J Pediatr. 209:116-124.e4 (2019) (13 pages).
Whyte et al., "Rickets and osteomalacia," Medicine. 37(9):483-8 (2009).
Whyte, Chapter 22: Hypophosphatasia, *Genetics of Bone Biology and Skeletal Disease*. Rajesh V. Thakker, Michael P. Whyte, John A. Eisman and Takashi Igarashi (eds.), 337-360 (2013).
Whyte, Chapter 73: Hypophosphatasia: Nature's Window on Alkaline Phosphatase Function in Humans, *Principles of Bone Biology*, vol. 1, Third Edition. John P. Bilezikian, Lawrence G. Raisz and T. John Martin (eds.), 1573-98 (2008).
Zaleckas et al., "Diagnosis and treatment of craniosynostosis: Vilnius team experience," Acta Med Litu. 22(2):111-21 (2015).
Bishop et al., "Life-threatening hypophosphatasia (HPP): Results of up to two years bone-targeted Enzyme Replacement Therapy (ERT) in infants and young children," Bone. 48:S82 (2011).
Kim et al., "Comparison of phenylketonuria (PKU) patients' height, weight and body mass index (BMI) to the general population," Mol Genet Metab. 105:328-329, 2012.
Whyte et al., "Treatment of children with hypophosphatasia (HPP) with ENB-0040: radiographic and DXA outcomes after 6 months of therapy," Horm Res Paediatr. 76(Suppl 2):26 (2011).
Office Action for Japanese Patent Application No. 2018-515934, dated Jul. 28, 2020 (7 pages).
Sequencia—"Bone targeted alkaline phosphatase, kits and methods of use thereof," UniParc, (Nov. 2, 2010), Database No. HI520929, accessed Nov. 2, 2020 (1 page).
Seefried et al., "Long-term Effectiveness of Asfotase Alfa Treatment in Adults with Pediatric-onset Hypophosphatasia in Routine Clinical Practice" 2020 American Society for Bone and Mineral Research Virtual Conference, Sep. 11-15, 2020.
Seefried et al., "Real-world Clinical Profiles of Adults with Hypophosphatasia (HPP) from the Global HPP Registry," The American Society for Bone and Mineral Research 2020 Annual Meeting, Sep. 11-15, virtually (2020).
Seefried et al., "Bone Turnover and Mineral Metabolism in Adult Patients with Pediatric-Onset Hypophosphatasia Treated With Asfotase Alfa," The American Society for Bone and Mineral Research 2020 Annual Meeting, Sep. 11-15, virtually (2020).
Seefried et al., "Long-term Effectiveness of Asfotase Alfa Treatment in Adults with Pediatric-onset Hypophosphatasia in Routine Clinical Practice" 22nd European Congress of Endocrinology, Sep. 5-9, virtual (2020).
Seefried et al., "Long-term Effectiveness of Asfotase Alfa Treatment in Adults with Pediatric-onset Hypophosphatasia in Routine Clinical Practice" 2020 World Congress of Osteoporosis, Osteoarthritis, and Muscoskeletal Diseases, Aug. 20-23, Barcelona, Spain (2020).
Anonymous: "Scale-up of CHO fed-batch cultures in HyClone (TM) ActiPro (TM) medium supplemented with Cell Boost (TM) 7a and 7b," Oct. 11, 2016, pp. 1-4, XP055461185.
Fu-Hang et al., "Preliminary study on the effect of $Zn^{2+}$ on the activities of peptidase and alkaline phosphatase," Marine Sciences. 27(3):64-65 (2003).
Office Action for Chinese Patent Application No. 201680048588.5, dated Jan. 18, 2021 (13 pages).
Dutta et al., "Men and mice: Relating their ages," Life Sci. 152:244-8 (2015).
Zhang et al., "Engineering *E. coli* Alkaline Phosphatase Yields Changes of Catalytic Activity, Thermal Stability and Phosphate Inhibition," Biocatal Biotransfor. 20(6):381-389 (2002).
Nangia et al., "Disorders of Calcium Metabolism in Newborns," Journal of Neonatology. 17(2):43-49 (2003).
Kochanowski et al., "Medium and feed optimization for fed-batch production of a monoclonal antibody in CHO cells," BMC Proc. 5(Suppl 8):P75 (2011) (3 pages).
"Xcellerex™ XDR cell culture bioreactor systems," GE Healthcare Life Sciences, retrieved from <https://www.cytivallifesciences.co.jp/catalog/pdf/29092925AA.pdf>, published Feb. 2014 (4 pages).
Yagasaki et al., "Animal Cell Technology: Basic & Applied Aspects," Proceedings of the Fifteenth Annual Meeting of the Japanese Association for Animal Cell Technology (JAACT), vol. 13, Fuchu, Nov. 11-15, 2002 (461 pages).
Kozlenkov et al., "Residues determining the binding specificity of uncompetitive inhibitors to tissue-nonspecific alkaline phosphatase," J Bone Miner Res. 19(11):1862-72 (2004).
NCBI Protein Database Accession No. NM_000478, retrieved on Feb. 23, 2021 (7 pages).
Pradhan et al., "Exposure-Response Modeling and Simulation to Support Evaluation of Efficacious and Safe Exposure and Dose Range for Asfotase alfa in Patients with Hypophosphatasia," ASBMR 2015 Annual Meeting Abstracts. J Bone and Med Res. SU0380:S316 (2015) (1 page).
Abbruzzese, L., "The Tinetti Performance-Oriented Mobility Assessment Tool," Am J Nursing. 98(12):16J-16L (1998) (3 pages).

(56) References Cited

OTHER PUBLICATIONS

International Search Report and Written Opinion for International Patent Application No. PCT/US20/64140, dated Apr. 23, 2021 (70 pages).

Kishnani et al., "Five-year efficacy and safety of asfotase alfa therapy for adults and adolescents with hypophosphatasia," Bone. 121:149-162 (2019).

Alexion Pharmaceuticals, "Safety Study of Human Recombinant Tissue Non-Specific Alkaline Phosphatase Fusion Protein Asfotase Alfa in Adults With Hypophosphatasia (HPP)," ClinicalTrials.gov. NCT00739505 (2008).

Alexion Pharmaceuticals, "Safety and Efficacy Study of Asfotase Alfa in Adolescents and Adults With Hypophosphatasia (HPP)," ClinicalTrials.gov. NCT01163149 (2010).

Alexion Pharmaceuticals, "Strensiq (asfotase alfa) for injection," <World wide web at globalgenes.org/2015/11/05/alexion-announces-fda-approval-for--strensiq/?gclid=CjwKCAjwwqaGBhBKEiwAMk-FtFQOKvuVN-WmNcDVyu9Q9X3f6QB-V0Two0x216TR2H4_Qc6jSlhvxoCiLMQAvD_BwE>, dated Nov. 5, 2015 (1 page).

European Medicines Agency, "Strensiq: Asfotase Alfa," <www.ema.europa.eu/en/medicines/human/EPAR/strensiq>, dated Mar. 25, 2021 (8 pages).

Hoffmann et al. "Efficacy and safety of asfotase alfa in infants and young children with hypophosphatasia: a phase 2 open-label study," J Clin Endocrinol Metab. 104(7): 2735-2747 (2019) (14 pages).

\* cited by examiner

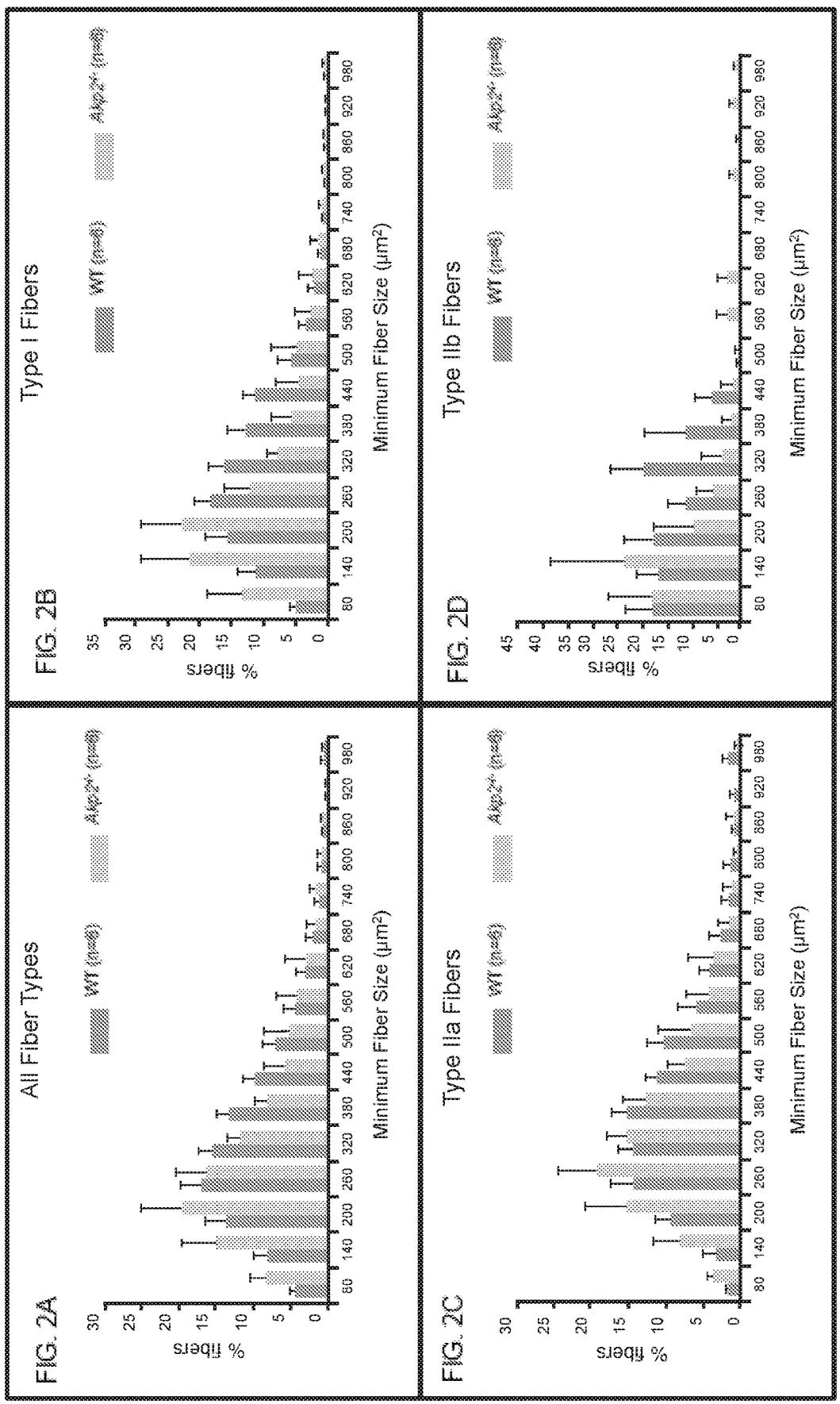

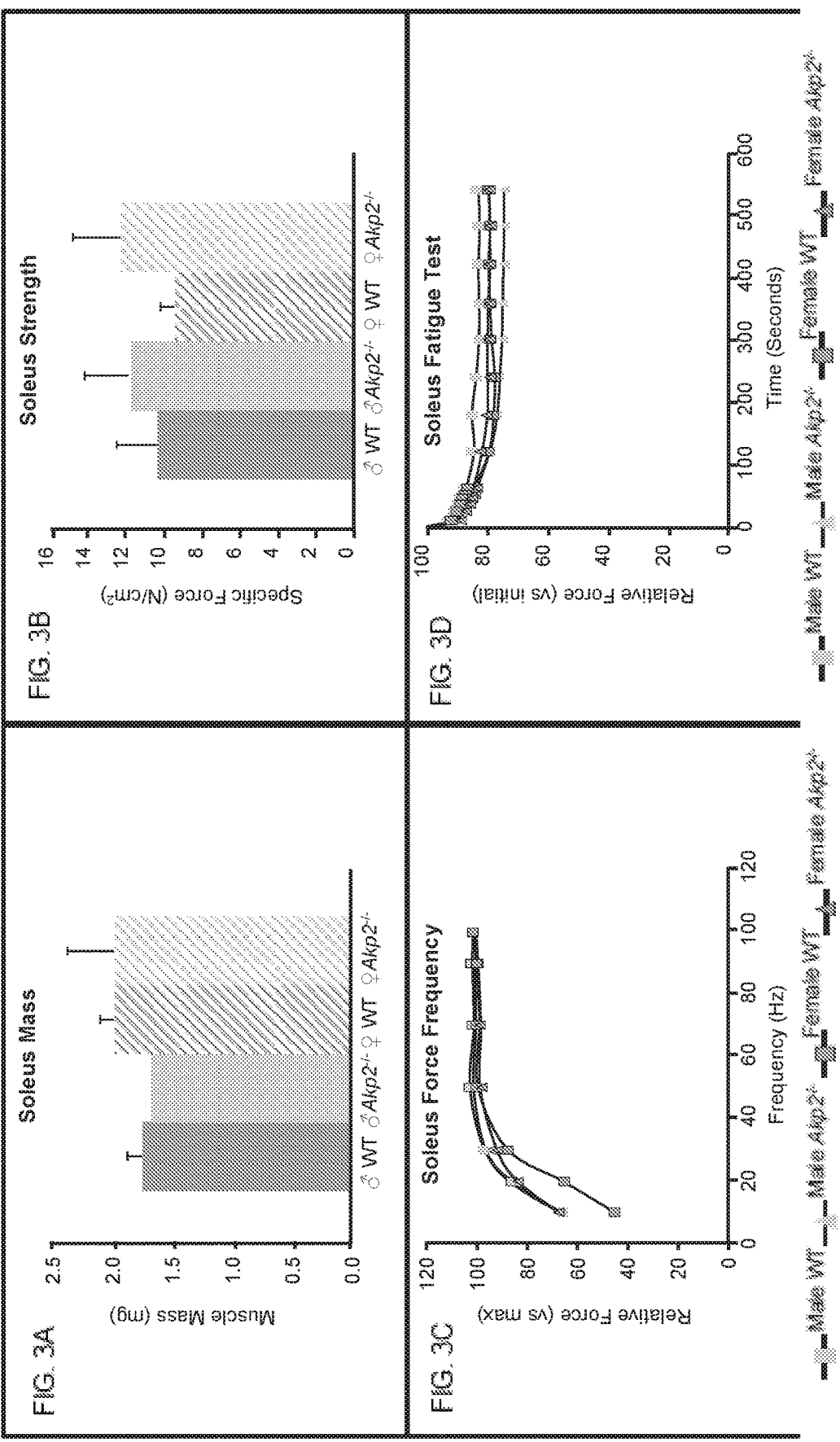

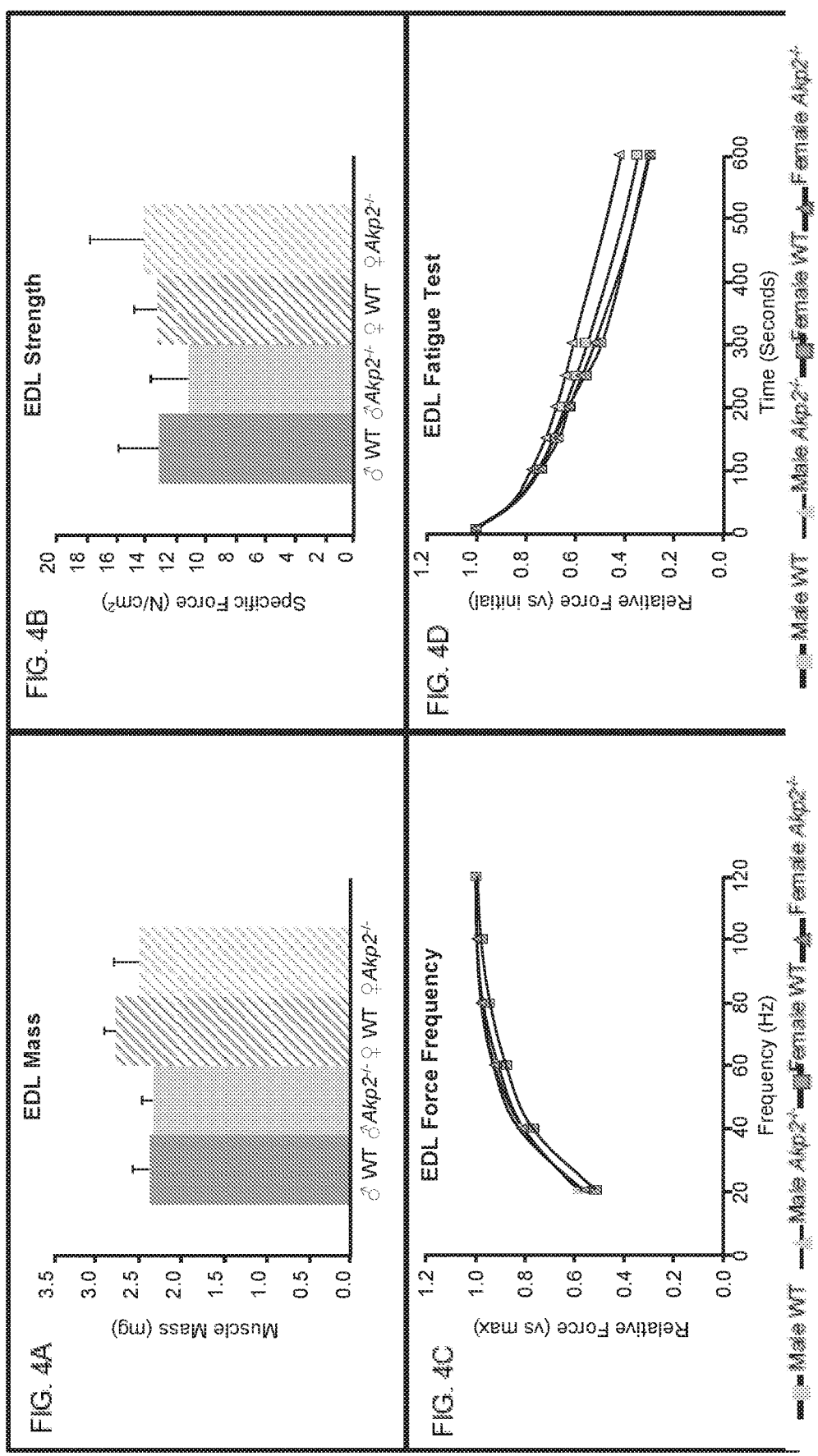

```
SEQUENCE LISTING

<160> NUMBER OF SEQ ID NOS: 20

<210> SEQ ID NO 1
<211> LENGTH: 726
<212> TYPE: PRT
<213> ORGANISM: Artificial Sequence
<220> FEATURE:
<223> OTHER INFORMATION: Synthetic Construct

<400> SEQUENCE: 1

Leu Val Pro Glu Lys Glu Lys Asp Pro Lys Tyr Trp Arg Asp Gln Ala
1               5                   10                  15

Gln Glu Thr Leu Lys Tyr Ala Leu Glu Leu Gln Lys Leu Asn Thr Asn
            20                  25                  30

Val Ala Lys Asn Val Ile Met Phe Leu Gly Asp Gly Met Gly Val Ser
        35                  40                  45

Thr Val Thr Ala Ala Arg Ile Leu Lys Gly Gln Leu His His Asn Pro
    50                  55                  60

Gly Glu Glu Thr Arg Leu Glu Met Asp Lys Phe Pro Phe Val Ala Leu
65                  70                  75                  80

Ser Lys Thr Tyr Asn Thr Asn Ala Gln Val Pro Asp Ser Ala Gly Thr
                85                  90                  95

Ala Thr Ala Tyr Leu Cys Gly Val Lys Ala Asn Glu Gly Thr Val Gly
            100                 105                 110

Val Ser Ala Ala Thr Glu Arg Ser Arg Cys Asn Thr Thr Gln Gly Asn
        115                 120                 125

Glu Val Thr Ser Ile Leu Arg Trp Ala Lys Asp Ala Gly Lys Ser Val
    130                 135                 140

Gly Ile Val Thr Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175

Pro Glu Ala Leu Ser Gln Gly Cys Lys Asp Ile Ala Tyr Gln Leu Met
            180                 185                 190

His Asn Ile Arg Asp Ile Asp Val Ile Met Gly Gly Gly Arg Lys Tyr
        195                 200                 205

Met Tyr Pro Lys Asn Lys Thr Asp Val Glu Tyr Glu Ser Asp Glu Lys
    210                 215                 220

Ala Arg Gly Thr Arg Leu Asp Gly Leu Asp Leu Val Asp Thr Trp Lys
225                 230                 235                 240
```

-continued

Ser Phe Lys Pro Arg Tyr Lys His Ser His Phe Ile Trp Asn Arg Thr
            245                 250                 255

Glu Leu Leu Thr Leu Asp Pro His Asn Val Asp Tyr Leu Leu Gly Leu
        260                 265                 270

Phe Glu Pro Gly Asp Met Gln Tyr Glu Leu Asn Arg Asn Asn Val Thr
        275                 280                 285

Asp Pro Ser Leu Ser Glu Met Val Val Ala Ile Gln Ile Leu Arg
    290                 295                 300

Lys Asn Pro Lys Gly Phe Phe Leu Leu Val Glu Gly Gly Arg Ile Asp
305                 310                 315                 320

His Gly His His Glu Gly Lys Ala Lys Gln Ala Leu His Glu Ala Val
                325                 330                 335

Glu Met Asp Arg Ala Ile Gly Gln Ala Gly Ser Leu Thr Ser Ser Glu
                340                 345                 350

Asp Thr Leu Thr Val Val Thr Ala Asp His Ser His Val Phe Thr Phe
        355                 360                 365

Gly Gly Tyr Thr Pro Arg Gly Asn Ser Ile Phe Gly Leu Ala Pro Met
    370                 375                 380

Leu Ser Asp Thr Asp Lys Lys Pro Phe Thr Ala Ile Leu Tyr Gly Asn
385                 390                 395                 400

Gly Pro Gly Tyr Lys Val Val Gly Gly Glu Arg Glu Asn Val Ser Met
                405                 410                 415

Val Asp Tyr Ala His Asn Asn Tyr Gln Ala Gln Ser Ala Val Pro Leu
                420                 425                 430

Arg His Glu Thr His Gly Gly Glu Asp Val Ala Val Phe Ser Lys Gly
        435                 440                 445

Pro Met Ala His Leu Leu His Gly Val His Glu Gln Asn Tyr Val Pro
    450                 455                 460

His Val Met Ala Tyr Ala Ala Cys Ile Gly Ala Asn Leu Gly His Cys
465                 470                 475                 480

Ala Pro Ala Ser Ser Leu Lys Asp Lys Thr His Thr Cys Pro Pro Cys
                485                 490                 495

Pro Ala Pro Glu Leu Leu Gly Gly Pro Ser Val Phe Leu Phe Pro Pro
            500                 505                 510

Lys Pro Lys Asp Thr Leu Met Ile Ser Arg Thr Pro Glu Val Thr Cys
    515                 520                 525

Val Val Val Asp Val Ser His Glu Asp Pro Glu Val Lys Phe Asn Trp
530                 535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
                580                 585                 590

Lys Ala Leu Pro Ala Pro Ile Glu Lys Thr Ile Ser Lys Ala Lys Gly
        595                 600                 605

Gln Pro Arg Glu Pro Gln Val Tyr Thr Leu Pro Pro Ser Arg Glu Glu
    610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
                645                 650                 655

```
Asn Tyr Lys Thr Thr Pro Val Leu Asp Ser Asp Gly Ser Phe Phe
            660                 665                 670

Leu Tyr Ser Lys Leu Thr Val Asp Lys Ser Arg Trp Gln Gln Gly Asn
        675                 680                 685

Val Phe Ser Cys Ser Val Met His Glu Ala Leu His Asn His Tyr Thr
    690                 695                 700

Gln Lys Ser Leu Ser Leu Ser Pro Gly Lys Asp Ile Asp Asp Asp
705                 710                 715                 720

Asp Asp Asp Asp Asp Asp
                725

<210> SEQ ID NO 2
<211> LENGTH: 524
<212> TYPE: PRT
<213> ORGANISM: Homo sapiens

<400> SEQUENCE: 2

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
    290                 295                 300
```

```
Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
                340                 345                 350

Val Glu Met Asp Arg Ala Ile Gly Gln Ala Gly Ser Leu Thr Ser Ser
            355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
                420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ser Lys
450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
                500                 505                 510

Leu Ala Leu Ala Leu Tyr Pro Leu Ser Val Leu Phe
                515                 520

<210> SEQ ID NO 3
<211> LENGTH: 524
<212> TYPE: PRT
<213> ORGANISM: Homo sapiens

<400> SEQUENCE: 3

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
                20                  25                  30

Ala Gln Glu Thr Leu Lys Tyr Ala Leu Glu Leu Gln Lys Leu Asn Thr
            35                  40                  45

Asn Val Ala Lys Asn Val Ile Met Phe Leu Gly Asp Gly Met Gly Val
        50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
                100                 105                 110

Thr Ala Thr Ala Tyr Leu Cys Gly Val Lys Ala Asn Glu Gly Thr Val
            115                 120                 125

Gly Val Ser Ala Ala Thr Glu Arg Ser Arg Cys Asn Thr Thr Gln Gly
130                 135                 140

Asn Glu Val Thr Ser Ile Leu Arg Trp Ala Lys Asp Ala Gly Lys Ser
```

```
            145                 150                 155                 160
Val Gly Ile Val Thr Thr Thr Arg Val Asn His Ala Thr Pro Ser Ala
                        165                 170                 175

Ala Tyr Ala His Ser Ala Asp Arg Asp Trp Tyr Ser Asp Asn Glu Met
                180                 185                 190

Pro Pro Glu Ala Leu Ser Gln Gly Cys Lys Asp Ile Ala Tyr Gln Leu
            195                 200                 205

Met His Asn Ile Arg Asp Ile Asp Val Ile Met Gly Gly Gly Arg Lys
        210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                        245                 250                 255

Lys Ser Phe Lys Pro Arg His Lys His Ser His Phe Ile Trp Asn Arg
                260                 265                 270

Thr Glu Leu Leu Thr Leu Asp Pro His Asn Val Asp Tyr Leu Leu Gly
            275                 280                 285

Leu Phe Glu Pro Gly Asp Met Gln Tyr Glu Leu Asn Arg Asn Asn Val
        290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                        325                 330                 335

Asp His Gly His His Glu Gly Lys Ala Lys Gln Ala Leu His Glu Ala
                340                 345                 350

Val Glu Met Asp Arg Ala Ile Gly Gln Ala Gly Ser Leu Thr Ser Ser
            355                 360                 365

Glu Asp Thr Leu Thr Val Val Thr Ala Asp His Ser His Val Phe Thr
        370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                        405                 410                 415

Asn Gly Pro Gly Tyr Lys Val Val Gly Glu Arg Glu Asn Val Ser
                420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ser Lys
        450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                        485                 490                 495

Cys Ala Pro Ala Ser Ser Ala Gly Ser Leu Ala Ala Gly Pro Leu Leu
                500                 505                 510

Leu Ala Leu Ala Leu Tyr Pro Leu Ser Val Leu Phe
            515                 520

<210> SEQ ID NO 4
<211> LENGTH: 524
<212> TYPE: PRT
<213> ORGANISM: Homo sapiens

<400> SEQUENCE: 4
```

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
            35                  40                  45

Asn Val Ala Lys Asn Val Ile Met Phe Leu Gly Asp Gly Met Gly Val
            50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
            85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
            115                 120                 125

Gly Val Ser Ala Ala Thr Glu Arg Ser Arg Cys Asn Thr Thr Gln Gly
            130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
            165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
            195                 200                 205

Met His Asn Ile Arg Asp Ile Asp Val Ile Met Gly Gly Gly Arg Lys
            210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
            245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
            275                 280                 285

Leu Phe Glu Pro Gly Asp Met Gln Tyr Glu Leu Asn Arg Asn Asn Val
            290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
            325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
            355                 360                 365

Glu Asp Thr Leu Thr Val Val Thr Ala Asp His Ser His Val Phe Thr
            370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
            405                 410                 415

Asn Gly Pro Gly Tyr Lys Val Val Gly Gly Glu Arg Glu Asn Val Ser

```
                    420             425             430
Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ser Lys
        450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
            485                 490                 495

Cys Ala Pro Ala Ser Ser Ala Gly Ser Leu Ala Ala Gly Pro Leu Leu
        500                 505                 510

Leu Ala Leu Ala Leu Tyr Pro Leu Ser Val Leu Phe
            515                 520

<210> SEQ ID NO 5
<211> LENGTH: 524
<212> TYPE: PRT
<213> ORGANISM: Homo sapiens

<400> SEQUENCE: 5

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270
```

```
Thr Glu Leu Leu Thr Leu Asp Pro His Asn Val Asp Tyr Leu Leu Gly
            275                 280                 285

Leu Phe Glu Pro Gly Asp Met Gln Tyr Glu Leu Asn Arg Asn Asn Val
290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Lys Gln Ala Leu His Glu Ala
            340                 345                 350

Val Glu Met Asp Arg Ala Ile Gly Gln Ala Gly Ser Leu Thr Ser Ser
            355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
                420                 425                 430

Met Val Asp Tyr Ala His Asn Asn Tyr Gln Ala Gln Ser Ala Val Pro
435                 440                 445

Leu Arg His Glu Thr His Gly Gly Glu Asp Val Ala Val Phe Ser Lys
            450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
                500                 505                 510

Leu Ala Leu Ala Leu Tyr Pro Leu Ser Val Leu Phe
            515                 520

<210> SEQ ID NO 6
<211> LENGTH: 524
<212> TYPE: PRT
<213> ORGANISM: Homo sapiens

<400> SEQUENCE: 6

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125
```

```
Gly Val Ser Ala Ala Thr Glu Arg Ser Arg Cys Asn Thr Thr Gln Gly
            130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg His Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
        355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ser Lys
450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
            500                 505                 510

Leu Ala Leu Ala Leu Tyr Pro Leu Ser Val Leu Phe
        515                 520

<210> SEQ ID NO 7
<211> LENGTH: 652
```

```
<212> TYPE: PRT
<213> ORGANISM: Macaca mulatta

<400> SEQUENCE: 7
```

| | | | | | | | | | | | | | | | |
|---|---|---|---|---|---|---|---|---|---|---|---|---|---|---|---|
| Met | Pro | Thr | Val | Lys | Thr | Lys | Gln | Glu | Ser | His | Ala | Gly | Ser | Gly | Ser |
| 1 | | | | 5 | | | | | 10 | | | | | 15 | |
| Gly | Pro | Arg | Leu | Ala | Glu | Arg | Lys | Gly | Arg | Val | Gly | Ala | Ala | Arg | Arg |
| | | | 20 | | | | | 25 | | | | | 30 | | |
| Gln | Ser | Pro | Arg | Ala | Pro | Gly | Gly | Leu | Pro | Gly | Pro | Arg | Ser | Gly | |
| | | 35 | | | | 40 | | | | | 45 | | | | |
| Pro | Ala | Ala | Ala | Phe | Ile | Arg | Arg | Gly | Arg | Trp | Pro | Gly | Pro | Arg | |
| | 50 | | | | | 55 | | | | | 60 | | | | |
| Cys | Ala | Pro | Ala | Thr | Pro | Arg | Pro | Arg | Ser | Arg | Leu | Cys | Ala | Pro | Thr |
| 65 | | | | | 70 | | | | | 75 | | | | | 80 |
| Arg | Leu | Cys | Leu | Asp | Glu | Pro | Ser | Ser | Val | Leu | Cys | Ala | Gly | Leu | Glu |
| | | | | 85 | | | | | 90 | | | | | 95 | |
| His | Gln | Leu | Thr | Ser | Asp | His | Cys | Gln | Pro | Thr | Pro | Ser | His | Pro | Arg |
| | | | 100 | | | | | 105 | | | | | 110 | | |
| Arg | Ser | His | Leu | Trp | Ala | Ser | Gly | Ile | Lys | Gln | Val | Leu | Gly | Cys | Thr |
| | | 115 | | | | | 120 | | | | | 125 | | | |
| Met | Ile | Ser | Pro | Phe | Leu | Val | Leu | Ala | Ile | Gly | Thr | Cys | Leu | Thr | Asn |
| 130 | | | | | 135 | | | | | 140 | | | | | |
| Ser | Leu | Val | Pro | Glu | Lys | Glu | Lys | Asp | Pro | Lys | Tyr | Trp | Arg | Asp | Gln |
| 145 | | | | | 150 | | | | | 155 | | | | | 160 |
| Ala | Gln | Glu | Thr | Leu | Lys | Tyr | Ala | Leu | Glu | Leu | Gln | Lys | Leu | Asn | Thr |
| | | | | 165 | | | | | 170 | | | | | 175 | |
| Asn | Val | Ala | Lys | Asn | Val | Ile | Met | Phe | Leu | Gly | Asp | Gly | Met | Gly | Val |
| | | | 180 | | | | | 185 | | | | | 190 | | |
| Ser | Thr | Val | Thr | Ala | Thr | Arg | Ile | Leu | Lys | Gly | Gln | Leu | His | His | Asn |
| | | | 195 | | | | | 200 | | | | | 205 | | |
| Pro | Gly | Glu | Glu | Thr | Arg | Leu | Glu | Met | Asp | Lys | Phe | Pro | Phe | Val | Ala |
| | 210 | | | | | 215 | | | | | 220 | | | | |
| Leu | Ser | Lys | Thr | Tyr | Asn | Thr | Asn | Ala | Gln | Val | Pro | Asp | Ser | Ala | Gly |
| 225 | | | | | 230 | | | | | 235 | | | | | 240 |
| Thr | Ala | Thr | Ala | Tyr | Leu | Cys | Gly | Val | Lys | Ala | Asn | Glu | Gly | Thr | Val |
| | | | | 245 | | | | | 250 | | | | | 255 | |
| Gly | Val | Ser | Ala | Ala | Thr | Glu | Arg | Ser | Arg | Cys | Asn | Thr | Thr | Gln | Gly |
| | | | 260 | | | | | 265 | | | | | 270 | | |
| Asn | Glu | Val | Thr | Ser | Ile | Leu | Arg | Trp | Ala | Lys | Asp | Ala | Gly | Lys | Ser |
| | | | 275 | | | | | 280 | | | | | 285 | | |
| Val | Gly | Ile | Val | Thr | Thr | Thr | Arg | Val | Asn | His | Ala | Thr | Pro | Ser | Ala |
| | 290 | | | | | 295 | | | | | 300 | | | | |
| Ala | Tyr | Ala | His | Ser | Ala | Asp | Arg | Asp | Trp | Tyr | Ser | Asp | Asn | Glu | Met |
| 305 | | | | | 310 | | | | | 315 | | | | | 320 |
| Pro | Pro | Glu | Ala | Leu | Ser | Gln | Gly | Cys | Lys | Asp | Ile | Ala | Tyr | Gln | Leu |
| | | | | 325 | | | | | 330 | | | | | 335 | |
| Val | His | Asn | Ile | Arg | Asp | Ile | Asp | Val | Ile | Met | Gly | Gly | Gly | Arg | Lys |
| | | | 340 | | | | | 345 | | | | | 350 | | |
| Tyr | Met | Tyr | Pro | Lys | Asn | Lys | Thr | Asp | Val | Glu | Tyr | Glu | Ile | Asp | Glu |
| | | | 355 | | | | | 360 | | | | | 365 | | |
| Lys | Ala | Arg | Gly | Thr | Arg | Leu | Asp | Gly | Leu | Asp | Leu | Val | Asn | Ile | Trp |
| | 370 | | | | | 375 | | | | | 380 | | | | |
| Lys | Ser | Phe | Lys | Pro | Arg | His | Lys | His | Ser | His | Phe | Ile | Trp | Asn | Arg |
| 385 | | | | | 390 | | | | | 395 | | | | | 400 |

```
Thr Glu Leu Leu Thr Leu Asp Pro His Asn Val Asp Tyr Leu Leu Gly
            405                 410                 415
Leu Phe Glu Pro Gly Asp Met Glu Tyr Glu Leu Asn Arg Asn Asn Val
            420                 425                 430
Thr Asp Pro Ser Leu Ser Glu Met Val Val Ala Ile Gln Ile Leu
            435                 440                 445
Arg Lys Asn Pro Lys Gly Phe Phe Leu Leu Val Glu Gly Gly Arg Ile
450                 455                 460
Asp His Gly His His Glu Gly Lys Ala Lys Gln Ala Leu His Glu Ala
465                 470                 475                 480
Val Glu Met Asp Arg Ala Ile Gly Gln Ala Gly Ser Met Thr Ser Leu
            485                 490                 495
Glu Asp Thr Leu Thr Val Val Thr Ala Asp His Ser His Val Phe Thr
            500                 505                 510
Phe Gly Gly Tyr Thr Pro Arg Gly Asn Ser Ile Phe Gly Leu Ala Pro
            515                 520                 525
Met Leu Ser Asp Thr Asp Lys Lys Pro Phe Thr Ala Ile Leu Tyr Gly
            530                 535                 540
Asn Gly Pro Gly Tyr Lys Val Val Gly Gly Glu Arg Glu Asn Val Ser
545                 550                 555                 560
Met Val Asp Tyr Ala His Asn Asn Tyr Gln Ala Gln Ser Ala Val Pro
            565                 570                 575
Leu Arg His Glu Thr His Gly Gly Glu Asp Val Ala Val Phe Ser Lys
            580                 585                 590
Gly Pro Met Ala His Leu Leu His Gly Val His Glu Gln Asn Tyr Ile
            595                 600                 605
Pro His Val Met Ala Tyr Ala Ala Cys Ile Gly Ala Asn Leu Asp His
            610                 615                 620
Cys Ala Pro Ala Ser Ser Ala Gly Ser Leu Ala Ala Gly Pro Leu Leu
625                 630                 635                 640
Leu Pro Leu Ala Leu Phe Pro Leu Ser Ile Leu Phe
            645                 650

<210> SEQ ID NO 8
<211> LENGTH: 524
<212> TYPE: PRT
<213> ORGANISM: Rattus norvegicus

<400> SEQUENCE: 8

Met Ile Leu Pro Phe Leu Val Leu Ala Ile Gly Pro Cys Leu Thr Asn
1               5                   10                  15
Ser Phe Val Pro Glu Lys Glu Lys Asp Pro Ser Tyr Trp Arg Gln Gln
            20                  25                  30
Ala Gln Glu Thr Leu Lys Asn Ala Leu Lys Leu Gln Lys Leu Asn Thr
            35                  40                  45
Asn Val Ala Lys Asn Ile Ile Met Phe Leu Gly Asp Gly Met Gly Val
            50                  55                  60
Ser Thr Val Thr Ala Ala Arg Ile Leu Lys Gly Gln Leu His His Asn
65                  70                  75                  80
Thr Gly Glu Glu Thr Arg Leu Glu Met Asp Lys Phe Pro Phe Val Ala
            85                  90                  95
Leu Ser Lys Thr Tyr Asn Thr Asn Ala Gln Val Pro Asp Ser Ala Gly
            100                 105                 110
Thr Ala Thr Ala Tyr Leu Cys Gly Val Lys Ala Asn Glu Gly Thr Val
```

```
            115                 120                 125
Gly Val Ser Ala Ala Thr Glu Arg Thr Arg Cys Asn Thr Thr Gln Gly
            130                 135                 140
Asn Glu Val Thr Ser Ile Leu Arg Trp Ala Lys Asp Ala Gly Lys Ser
145                 150                 155                 160
Val Gly Ile Val Thr Thr Thr Arg Val Asn His Ala Thr Pro Ser Ala
                    165                 170                 175
Ala Tyr Ala His Ser Ala Asp Arg Asp Trp Tyr Ser Asp Asn Glu Met
                180                 185                 190
Arg Pro Glu Ala Leu Ser Gln Gly Cys Lys Asp Ile Ala Tyr Gln Leu
            195                 200                 205
Met His Asn Ile Lys Asp Ile Asp Val Ile Met Gly Gly Gly Arg Lys
        210                 215                 220
Tyr Met Tyr Pro Lys Asn Arg Thr Asp Val Glu Tyr Glu Leu Asp Glu
225                 230                 235                 240
Lys Ala Arg Gly Thr Arg Leu Asp Gly Leu Asp Leu Ile Ser Ile Trp
                245                 250                 255
Lys Ser Phe Lys Pro Arg His Lys His Ser His Tyr Val Trp Asn Arg
                260                 265                 270
Thr Glu Leu Leu Ala Leu Asp Pro Ser Arg Val Asp Tyr Leu Leu Gly
            275                 280                 285
Leu Phe Glu Pro Gly Asp Met Gln Tyr Glu Leu Asn Arg Asn Asn Leu
        290                 295                 300
Thr Asp Pro Ser Leu Ser Glu Met Val Glu Val Ala Leu Arg Ile Leu
305                 310                 315                 320
Thr Lys Asn Pro Lys Gly Phe Phe Leu Leu Val Glu Gly Gly Arg Ile
                325                 330                 335
Asp His Gly His His Glu Gly Lys Ala Lys Gln Ala Leu His Glu Ala
            340                 345                 350
Val Glu Met Asp Glu Ala Ile Gly Lys Ala Gly Thr Met Thr Ser Gln
            355                 360                 365
Lys Asp Thr Leu Thr Val Val Thr Ala Asp His Ser His Val Phe Thr
370                 375                 380
Phe Gly Gly Tyr Thr Pro Arg Gly Asn Ser Ile Phe Gly Leu Ala Pro
385                 390                 395                 400
Met Val Ser Asp Thr Asp Lys Lys Pro Phe Thr Ala Ile Leu Tyr Gly
                405                 410                 415
Asn Gly Pro Gly Tyr Lys Val Val Asp Gly Glu Arg Glu Asn Val Ser
                420                 425                 430
Met Val Asp Tyr Ala His Asn Asn Tyr Gln Ala Gln Ser Ala Val Pro
            435                 440                 445
Leu Arg His Glu Thr His Gly Gly Glu Asp Val Ala Val Phe Ala Lys
            450                 455                 460
Gly Pro Met Ala His Leu Leu His Gly Val His Glu Gln Asn Tyr Ile
465                 470                 475                 480
Pro His Val Met Ala Tyr Ala Ser Cys Ile Gly Ala Asn Leu Asp His
                485                 490                 495
Cys Ala Trp Ala Ser Ser Ala Ser Ser Pro Ser Pro Gly Ala Leu Leu
                500                 505                 510
Leu Pro Leu Ala Leu Phe Pro Leu Arg Thr Leu Phe
            515                 520

<210> SEQ ID NO 9
```

<211> LENGTH: 502
<212> TYPE: PRT
<213> ORGANISM: Canis lupus familiaris

<400> SEQUENCE: 9

```
Glu Lys Asp Pro Lys Tyr Trp Arg Asp Gln Ala Gln Gln Thr Leu Lys
1               5                   10                  15

Tyr Ala Leu Arg Leu Gln Asn Leu Asn Thr Asn Val Ala Lys Asn Val
            20                  25                  30

Ile Met Phe Leu Gly Asp Gly Met Gly Val Ser Thr Val Thr Ala Thr
        35                  40                  45

Arg Ile Leu Lys Gly Gln Leu His His Asn Pro Gly Glu Glu Thr Arg
    50                  55                  60

Leu Glu Met Asp Lys Phe Pro Tyr Val Ala Leu Ser Lys Thr Tyr Asn
65                  70                  75                  80

Thr Asn Ala Gln Val Pro Asp Ser Ala Gly Thr Ala Thr Ala Tyr Leu
                85                  90                  95

Cys Gly Val Lys Ala Asn Glu Gly Thr Val Gly Val Ser Ala Ala Thr
            100                 105                 110

Gln Arg Thr His Cys Asn Thr Thr Gln Gly Asn Glu Val Thr Ser Ile
        115                 120                 125

Leu Arg Trp Ala Lys Asp Ala Gly Lys Ser Val Gly Ile Val Thr Thr
    130                 135                 140

Thr Arg Val Asn His Ala Thr Pro Ser Ala Ala Tyr Ala His Ser Ala
145                 150                 155                 160

Asp Arg Asp Trp Tyr Ser Asp Asn Glu Met Pro Pro Glu Ala Leu Ser
                165                 170                 175

Gln Gly Cys Lys Asp Ile Ala Tyr Gln Leu Met His Asn Val Lys Asp
            180                 185                 190

Ile Glu Val Ile Met Gly Gly Gly Arg Lys Tyr Met Phe Pro Lys Asn
        195                 200                 205

Arg Thr Asp Val Glu Tyr Glu Met Asp Glu Lys Ser Thr Gly Ala Arg
    210                 215                 220

Leu Asp Gly Leu Asn Leu Ile Asp Ile Trp Lys Asn Phe Lys Pro Arg
225                 230                 235                 240

His Lys His Ser His Tyr Val Trp Asn Arg Thr Glu Leu Leu Ala Leu
                245                 250                 255

Asp Pro Tyr Thr Val Asp Tyr Leu Leu Gly Leu Phe Asp Pro Gly Asp
            260                 265                 270

Met Gln Tyr Glu Leu Asn Arg Asn Asn Val Thr Asp Pro Ser Leu Ser
        275                 280                 285

Glu Met Val Glu Ile Ala Ile Lys Ile Leu Ser Lys Lys Pro Arg Gly
    290                 295                 300

Phe Phe Leu Leu Val Glu Gly Gly Arg Ile Asp His Gly His His Glu
305                 310                 315                 320

Gly Lys Ala Lys Gln Ala Leu His Glu Ala Val Glu Met Asp Arg Ala
                325                 330                 335

Ile Gly Lys Ala Gly Val Met Thr Ser Leu Glu Asp Thr Leu Thr Val
            340                 345                 350

Val Thr Ala Asp His Ser His Val Phe Thr Phe Gly Gly Tyr Thr Pro
        355                 360                 365

Arg Gly Asn Ser Ile Phe Gly Leu Ala Pro Met Val Ser Asp Thr Asp
    370                 375                 380

Lys Lys Pro Phe Thr Ala Ile Leu Tyr Gly Asn Gly Pro Gly Tyr Lys
```

```
                385                 390                 395                 400
Val Val Gly Gly Glu Arg Glu Asn Val Ser Met Val Asp Tyr Ala His
                    405                 410                 415

Asn Asn Tyr Gln Ala Gln Ser Ala Val Pro Leu Arg His Glu Thr His
                420                 425                 430

Gly Gly Glu Asp Val Ala Val Phe Ala Lys Gly Pro Met Ala His Leu
                435                 440                 445

Leu His Gly Val His Glu Gln Asn Tyr Ile Pro His Val Met Ala Tyr
            450                 455                 460

Ala Ala Cys Ile Gly Ala Asn Gln Asp His Cys Ala Ser Ala Ser Ser
465                 470                 475                 480

Ala Gly Gly Pro Ser Pro Gly Pro Leu Leu Leu Leu Ala Leu Leu
                    485                 490                 495

Pro Val Gly Ile Leu Phe
            500

<210> SEQ ID NO 10
<211> LENGTH: 252
<212> TYPE: PRT
<213> ORGANISM: Sus scrofa

<400> SEQUENCE: 10

Ala Glu Leu Leu Ala Leu Asp Pro His Thr Val Asp Tyr Leu Leu Gly
1               5                   10                  15

Leu Phe Glu Pro Gly Asp Met Gln Tyr Glu Leu Asn Arg Asn Asn Val
                20                  25                  30

Thr Asp Pro Ser Leu Ser Glu Met Val Glu Met Ala Ile Arg Ile Leu
            35                  40                  45

Ile Lys Asn Pro Lys Gly Phe Phe Leu Leu Val Glu Gly Gly Arg Ile
50                  55                  60

Asp His Gly His His Glu Gly Lys Ala Lys Gln Ala Leu His Glu Ala
65                  70                  75                  80

Val Glu Met Asp Arg Ala Ile Glu Gln Ala Gly Ser Met Thr Ser Val
                85                  90                  95

Glu Asp Thr Leu Thr Val Val Thr Ala Asp His Ser His Val Phe Thr
            100                 105                 110

Phe Gly Gly Tyr Thr Pro Arg Gly Asn Ser Ile Phe Gly Leu Ala Pro
        115                 120                 125

Met Val Ser Asp Thr Asp Lys Lys Pro Phe Thr Ala Ile Leu Tyr Gly
130                 135                 140

Asn Gly Pro Gly Tyr Lys Val Val Gly Gly Glu Arg Glu Asn Val Ser
145                 150                 155                 160

Met Val Asp Tyr Ala His Asp Asn Tyr Gln Ala Gln Ser Ala Val Pro
                165                 170                 175

Leu Arg His Glu Thr His Gly Gly Glu Asp Val Ala Ile Phe Ala Arg
            180                 185                 190

Gly Pro Met Ala His Leu Leu His Gly Val His Glu Gln Asn Tyr Ile
        195                 200                 205

Pro His Val Met Ala Tyr Ala Ala Cys Val Gly Ala Asn Arg Asp His
    210                 215                 220

Cys Ala Ser Ala Ser Ser Gly Ser Pro Ser Pro Gly Pro Leu Leu
225                 230                 235                 240

Leu Leu Leu Ala Leu Leu Pro Leu Gly Ile Leu Phe
                245                 250
```

```
<210> SEQ ID NO 11
<211> LENGTH: 524
<212> TYPE: PRT
<213> ORGANISM: Mus musculus

<400> SEQUENCE: 11
```

| | | | | | | | | | | | | | | | |
|---|---|---|---|---|---|---|---|---|---|---|---|---|---|---|---|
| Met | Ile | Ser | Pro | Phe | Leu | Val | Leu | Ala | Ile | Gly | Thr | Cys | Leu | Thr | Asn |
| 1 | | | | 5 | | | | | 10 | | | | | 15 | |
| Ser | Phe | Val | Pro | Glu | Lys | Glu | Arg | Asp | Pro | Ser | Tyr | Trp | Arg | Gln | Gln |
| | | | 20 | | | | | 25 | | | | | 30 | | |
| Ala | Gln | Glu | Thr | Leu | Lys | Asn | Ala | Leu | Lys | Leu | Gln | Lys | Leu | Asn | Thr |
| | | | | 35 | | | | | 40 | | | | | 45 | |
| Asn | Val | Ala | Lys | Asn | Val | Ile | Met | Phe | Leu | Gly | Asp | Gly | Met | Gly | Val |
| | 50 | | | | | 55 | | | | | 60 | | | | |
| Ser | Thr | Val | Thr | Ala | Ala | Arg | Ile | Leu | Lys | Gly | Gln | Leu | His | His | Asn |
| 65 | | | | | 70 | | | | | 75 | | | | | 80 |
| Thr | Gly | Glu | Glu | Thr | Arg | Leu | Glu | Met | Asp | Lys | Phe | Pro | Phe | Val | Ala |
| | | | | 85 | | | | | 90 | | | | | 95 | |
| Leu | Ser | Lys | Thr | Tyr | Asn | Thr | Asn | Ala | Gln | Val | Pro | Asp | Ser | Ala | Gly |
| | | | 100 | | | | | 105 | | | | | 110 | | |
| Thr | Ala | Thr | Ala | Tyr | Leu | Cys | Gly | Val | Lys | Ala | Asn | Glu | Gly | Thr | Val |
| | | | | 115 | | | | | 120 | | | | | 125 | |
| Gly | Val | Ser | Ala | Ala | Thr | Glu | Arg | Thr | Arg | Cys | Asn | Thr | Thr | Gln | Gly |
| | 130 | | | | | 135 | | | | | 140 | | | | |
| Asn | Glu | Val | Thr | Ser | Ile | Leu | Arg | Trp | Ala | Lys | Asp | Ala | Gly | Lys | Ser |
| 145 | | | | | 150 | | | | | 155 | | | | | 160 |
| Val | Gly | Ile | Val | Thr | Thr | Thr | Arg | Val | Asn | His | Ala | Thr | Pro | Ser | Ala |
| | | | | 165 | | | | | 170 | | | | | 175 | |
| Ala | Tyr | Ala | His | Ser | Ala | Asp | Arg | Asp | Trp | Tyr | Ser | Asp | Asn | Glu | Met |
| | | | 180 | | | | | 185 | | | | | 190 | | |
| Pro | Pro | Glu | Ala | Leu | Ser | Gln | Gly | Cys | Lys | Asp | Ile | Ala | Tyr | Gln | Leu |
| | | | | 195 | | | | | 200 | | | | | 205 | |
| Met | His | Asn | Ile | Lys | Asp | Ile | Asp | Val | Ile | Met | Gly | Gly | Gly | Arg | Lys |
| | 210 | | | | | 215 | | | | | 220 | | | | |
| Tyr | Met | Tyr | Pro | Lys | Asn | Arg | Thr | Asp | Val | Glu | Tyr | Glu | Leu | Asp | Glu |
| 225 | | | | | 230 | | | | | 235 | | | | | 240 |
| Lys | Ala | Arg | Gly | Thr | Arg | Leu | Asp | Gly | Leu | Asp | Leu | Ile | Ser | Ile | Trp |
| | | | | 245 | | | | | 250 | | | | | 255 | |
| Lys | Ser | Phe | Lys | Pro | Arg | His | Lys | His | Ser | His | Tyr | Val | Trp | Asn | Arg |
| | | | 260 | | | | | 265 | | | | | 270 | | |
| Thr | Glu | Leu | Leu | Ala | Leu | Asp | Pro | Ser | Arg | Val | Asp | Tyr | Leu | Leu | Gly |
| | | | | 275 | | | | | 280 | | | | | 285 | |
| Leu | Phe | Glu | Pro | Gly | Asp | Met | Gln | Tyr | Glu | Leu | Asn | Arg | Asn | Asn | Leu |
| | 290 | | | | | 295 | | | | | 300 | | | | |
| Thr | Asp | Pro | Ser | Leu | Ser | Glu | Met | Val | Glu | Val | Ala | Leu | Arg | Ile | Leu |
| 305 | | | | | 310 | | | | | 315 | | | | | 320 |
| Thr | Lys | Asn | Leu | Lys | Gly | Phe | Phe | Leu | Leu | Val | Glu | Gly | Gly | Arg | Ile |
| | | | | 325 | | | | | 330 | | | | | 335 | |
| Asp | His | Gly | His | His | Glu | Gly | Lys | Ala | Lys | Gln | Ala | Leu | His | Glu | Ala |
| | | | 340 | | | | | 345 | | | | | 350 | | |
| Val | Glu | Met | Asp | Gln | Ala | Ile | Gly | Lys | Ala | Gly | Ala | Met | Thr | Ser | Gln |
| | | | | 355 | | | | | 360 | | | | | 365 | |
| Lys | Asp | Thr | Leu | Thr | Val | Val | Thr | Ala | Asp | His | Ser | His | Val | Phe | Thr |
| | 370 | | | | | 375 | | | | | 380 | | | | |

```
Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ala Ile Leu Tyr Gly
                405                 410                 415

Asn Gly Pro Gly Tyr Lys Val Val Asp Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ala Lys
450                 455                 460

Gly Pro Met Ala His Leu Leu His Gly Val His Glu Gln Asn Tyr Ile
465                 470                 475                 480

Pro His Val Met Ala Tyr Ala Ser Cys Ile Gly Ala Asn Leu Asp His
                485                 490                 495

Cys Ala Trp Ala Gly Ser Gly Ser Ala Pro Ser Pro Gly Ala Leu Leu
            500                 505                 510

Leu Pro Leu Ala Val Leu Ser Leu Arg Thr Leu Phe
515                 520

<210> SEQ ID NO 12
<211> LENGTH: 524
<212> TYPE: PRT
<213> ORGANISM: Bos taurus

<400> SEQUENCE: 12

Met Ile Ser Pro Phe Leu Leu Ala Ile Gly Thr Cys Phe Ala Ser
1               5                   10                  15

Ser Leu Val Pro Glu Lys Glu Lys Asp Pro Lys Tyr Trp Arg Asp Gln
            20                  25                  30

Ala Gln Gln Thr Leu Lys Asn Ala Leu Arg Leu Gln Thr Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Ser
65                  70                  75                  80

Pro Gly Glu Glu Thr Lys Leu Glu Met Asp Lys Phe Pro Tyr Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Gln Arg Ser Gln Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ser Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Lys Asp Ile Glu Val Ile Met Gly Gly Gly Arg Lys
    210                 215                 220

Tyr Met Phe Pro Lys Asn Arg Thr Asp Val Glu Tyr Glu Leu Asp Glu
```

```
            225                 230                 235                 240

Lys Ala Arg Gly Thr Arg Leu Asp Gly Leu Asn Leu Ile Asp Ile Trp
                        245                 250                 255

Lys Ser Phe Lys Pro Lys His Lys Ser His Tyr Val Trp Asn Arg
                    260                 265                 270

Thr Asp Leu Ala Leu Asp Pro His Ser Val Asp Tyr Leu Leu Gly
                275                 280                 285

Leu Phe Glu Pro Gly Asp Met Gln Tyr Glu Leu Asn Arg Asn Asn Ala
            290                 295                 300

Thr Asp Pro Ser Leu Ser Glu Met Val Glu Met Ala Ile Arg Ile Leu
        305                 310                 315                 320

Asn Lys Asn Pro Lys Gly Phe Phe Leu Leu Val Glu Gly Gly Arg Ile
                        325                 330                 335

Asp His Gly His His Glu Gly Lys Ala Lys Gln Ala Leu His Glu Ala
                    340                 345                 350

Val Glu Met Asp Gln Ala Ile Gly Gln Ala Gly Ala Met Thr Ser Val
                355                 360                 365

Glu Asp Thr Leu Thr Val Val Thr Ala Asp His Ser His Val Phe Thr
            370                 375                 380

Phe Gly Gly Tyr Thr Pro Arg Gly Asn Ser Ile Phe Gly Leu Ala Pro
        385                 390                 395                 400

Met Val Ser Asp Thr Asp Lys Lys Pro Phe Thr Ala Ile Leu Tyr Gly
                        405                 410                 415

Asn Gly Pro Gly Tyr Lys Val Val Gly Gly Glu Arg Glu Asn Val Ser
                    420                 425                 430

Met Val Asp Tyr Ala His Asn Asn Tyr Gln Ala Gln Ser Ala Val Pro
                435                 440                 445

Leu Arg His Glu Thr His Gly Gly Glu Asp Val Ala Val Phe Ala Lys
            450                 455                 460

Gly Pro Met Ala His Leu Leu His Gly Val His Glu Gln Asn Tyr Ile
        465                 470                 475                 480

Pro His Val Met Ala Tyr Ala Ala Cys Ile Gly Ala Asn Arg Asp His
                        485                 490                 495

Cys Ala Ser Ala Ser Ser Ser Gly Ser Pro Ser Pro Gly Pro Leu Leu
                    500                 505                 510

Leu Leu Leu Ala Leu Leu Pro Leu Gly Ser Leu Phe
                515                 520

<210> SEQ ID NO 13
<211> LENGTH: 524
<212> TYPE: PRT
<213> ORGANISM: Bos taurus

<400> SEQUENCE: 13

Met Ile Ser Pro Phe Leu Leu Leu Ala Ile Gly Thr Cys Phe Ala Ser
1               5                   10                  15

Ser Leu Val Pro Glu Lys Glu Lys Asp Pro Lys Tyr Trp Arg Asp Gln
            20                  25                  30

Ala Gln Gln Thr Leu Lys Asn Ala Leu Arg Leu Gln Thr Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Ser
65                  70                  75                  80
```

```
Pro Gly Glu Glu Thr Lys Leu Glu Met Asp Lys Phe Pro Tyr Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Gln Arg Ser Gln Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ser Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Lys Asp Ile Glu Val Ile Met Gly Gly Gly Arg Lys
    210                 215                 220

Tyr Met Phe Pro Lys Asn Arg Thr Asp Val Glu Tyr Glu Leu Asp Glu
225                 230                 235                 240

Lys Ala Arg Gly Thr Arg Leu Asp Gly Leu Asn Leu Ile Asp Ile Trp
                245                 250                 255

Lys Ser Phe Lys Pro Lys His Lys Ser His Tyr Val Trp Asn Arg
            260                 265                 270

Thr Asp Leu Leu Ala Leu Asp Pro His Ser Val Asp Tyr Leu Leu Gly
        275                 280                 285

Leu Phe Glu Pro Gly Asp Met Gln Tyr Glu Leu Asn Arg Asn Asn Ala
    290                 295                 300

Thr Asp Pro Ser Leu Ser Glu Met Val Glu Met Ala Ile Arg Ile Leu
305                 310                 315                 320

Asn Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Gln Ala Ile Gly Gln Ala Gly Ala Met Thr Ser Val
        355                 360                 365

Glu Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ala Lys
    450                 455                 460

Gly Pro Met Ala His Leu Leu His Gly Val His Glu Gln Asn Tyr Ile
465                 470                 475                 480

Pro His Val Met Ala Tyr Ala Ala Cys Ile Gly Ala Asn Arg Asp His
                485                 490                 495

Cys Ala Ser Ala Ser Ser Ser Gly Ser Pro Ser Pro Gly Pro Leu Leu
```

```
                500               505               510
Leu Leu Leu Ala Leu Leu Pro Leu Gly Ser Leu Phe
            515                 520

<210> SEQ ID NO 14
<211> LENGTH: 124
<212> TYPE: PRT
<213> ORGANISM: Bos taurus

<400> SEQUENCE: 14

Asp Pro Lys Tyr Trp Arg Asp Gln Ala Gln Gln Thr Leu Lys Asn Ala
1               5                   10                  15

Leu Gly Leu Gln Lys Leu Asn Thr Lys Val Ala Lys Asn Val Ile Leu
            20                  25                  30

Phe Leu Gly Asp Gly Met Gly Val Ser Thr Val Thr Ala Ala Arg Ile
        35                  40                  45

Leu Lys Gly Gln Leu His His Asn Pro Gly Glu Glu Thr Arg Leu Glu
    50                  55                  60

Met Asp Lys Phe Pro Phe Val Ala Leu Ser Lys Thr Tyr Asn Thr Asn
65                  70                  75                  80

Ala Gln Val Pro Asp Ser Ala Gly Thr Ala Pro His Pro Val Arg Val
                85                  90                  95

Lys Ala Met Arg Ala Pro Trp Gly Glu Pro His Gln Arg Gln Cys Asn
            100                 105                 110

Thr Arg Arg Ala Thr Ser Thr His Leu Leu Ala Gly
        115                 120

<210> SEQ ID NO 15
<211> LENGTH: 524
<212> TYPE: PRT
<213> ORGANISM: Felis catus

<400> SEQUENCE: 15

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Gln Thr Leu Lys Asn Ala Leu Arg Leu Gln Lys Leu Asn Thr
        35                  40                  45

Asn Val Val Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Tyr Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Gln Arg Thr Gln Cys Asn Thr Thr Gln Gly
    130                 135                 140

Asn Glu Val Thr Ser Ile Leu Arg Trp Ala Lys Asp Ser Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
```

```
                180                 185                 190
Pro Pro Glu Ala Leu Ser Gln Gly Cys Lys Asp Ile Ala Tyr Gln Leu
            195                 200                 205

Met His Asn Val Arg Asp Ile Glu Val Ile Met Gly Gly Gly Arg Lys
        210                 215                 220

Tyr Met Phe Pro Lys Asn Arg Thr Asp Val Glu Tyr Glu Met Asp Glu
225                 230                 235                 240

Lys Ala Arg Gly Thr Arg Leu Asp Gly Leu Asn Leu Val Asp Ile Trp
                245                 250                 255

Lys Ser Phe Lys Pro Arg His Lys His Ser His Tyr Val Trp Asn Arg
            260                 265                 270

Thr Glu Leu Leu Thr Leu Asp Pro Tyr Gly Val Asp Tyr Leu Leu Gly
        275                 280                 285

Leu Phe Glu Pro Gly Asp Met Gln Tyr Glu Leu Asn Arg Asn Ser Thr
290                 295                 300

Thr Asp Pro Ser Leu Ser Glu Met Val Glu Ile Ala Ile Lys Ile Leu
305                 310                 315                 320

Ser Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Gln Ala Ile Gly Arg Ala Gly Ala Met Thr Ser Val
        355                 360                 365

Glu Asp Thr Leu Thr Ile Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ser Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ala Lys
450                 455                 460

Gly Pro Met Ala His Leu Leu His Gly Val His Glu Gln Asn Tyr Ile
465                 470                 475                 480

Pro His Val Met Ala Tyr Ala Ala Cys Ile Gly Ala Asn Leu Asp His
                485                 490                 495

Cys Ala Ser Ala Ser Ser Ala Gly Gly Pro Ser Pro Gly Pro Leu Phe
            500                 505                 510

Leu Leu Leu Ala Leu Pro Ser Leu Gly Ile Leu Phe
        515                 520

<210> SEQ ID NO 16
<211> LENGTH: 532
<212> TYPE: PRT
<213> ORGANISM: Homo sapiens

<400> SEQUENCE: 16

Met Gln Gly Pro Trp Val Leu Leu Leu Leu Gly Leu Arg Leu Gln Leu
1               5                   10                  15

Ser Leu Gly Ile Ile Pro Val Glu Glu Glu Asn Pro Asp Phe Trp Asn
            20                  25                  30
```

```
Arg Gln Ala Ala Glu Ala Leu Gly Ala Ala Lys Lys Leu Gln Pro Ala
                35                  40                  45
Gln Thr Ala Ala Lys Asn Leu Ile Ile Phe Leu Gly Asp Gly Met Gly
 50                  55                  60
Val Ser Thr Val Thr Ala Ala Arg Ile Leu Lys Gly Gln Lys Lys Asp
 65                  70                  75                  80
Lys Leu Gly Pro Glu Thr Phe Leu Ala Met Asp Arg Phe Pro Tyr Val
                 85                  90                  95
Ala Leu Ser Lys Thr Tyr Ser Val Asp Lys His Val Pro Asp Ser Gly
                100                 105                 110
Ala Thr Ala Thr Ala Tyr Leu Cys Gly Val Lys Gly Asn Phe Gln Thr
                115                 120                 125
Ile Gly Leu Ser Ala Ala Ala Arg Phe Asn Gln Cys Asn Thr Thr Arg
130                 135                 140
Gly Asn Glu Val Ile Ser Val Met Asn Arg Ala Lys Lys Ala Gly Lys
145                 150                 155                 160
Ser Val Gly Val Val Thr Thr Thr Arg Val Gln His Ala Ser Pro Ala
                165                 170                 175
Gly Ala Tyr Ala His Thr Val Asn Arg Asn Trp Tyr Ser Asp Ala Asp
                180                 185                 190
Val Pro Ala Ser Ala Arg Gln Glu Gly Cys Gln Asp Ile Ala Thr Gln
                195                 200                 205
Leu Ile Ser Asn Met Asp Ile Asp Val Ile Leu Gly Gly Gly Arg Lys
                210                 215                 220
Tyr Met Phe Pro Met Gly Thr Pro Asp Pro Glu Tyr Pro Asp Asp Tyr
225                 230                 235                 240
Ser Gln Gly Gly Thr Arg Leu Asp Gly Lys Asn Leu Val Gln Glu Trp
                245                 250                 255
Leu Ala Lys His Gln Gly Ala Arg Tyr Val Trp Asn Arg Thr Glu Leu
                260                 265                 270
Leu Gln Ala Ser Leu Asp Pro Ser Val Thr His Leu Met Gly Leu Phe
                275                 280                 285
Glu Pro Gly Asp Met Lys Tyr Glu Ile His Arg Asp Ser Thr Leu Asp
290                 295                 300
Pro Ser Leu Met Glu Met Thr Glu Ala Ala Leu Leu Leu Leu Ser Arg
305                 310                 315                 320
Asn Pro Arg Gly Phe Phe Leu Phe Val Glu Gly Gly Arg Ile Asp His
                325                 330                 335
Gly His His Glu Ser Arg Ala Tyr Arg Ala Leu Thr Glu Thr Ile Met
                340                 345                 350
Phe Asp Asp Ala Ile Glu Arg Ala Gly Gln Leu Thr Ser Glu Glu Asp
                355                 360                 365
Thr Leu Ser Leu Val Thr Ala Asp His Ser His Val Phe Ser Phe Gly
370                 375                 380
Gly Tyr Pro Leu Arg Gly Ser Ser Ile Phe Gly Leu Ala Pro Gly Lys
385                 390                 395                 400
Ala Arg Asp Arg Lys Ala Tyr Thr Val Leu Leu Tyr Gly Asn Gly Pro
                405                 410                 415
Gly Tyr Val Leu Lys Asp Gly Ala Arg Pro Asp Val Thr Glu Ser Glu
                420                 425                 430
Ser Gly Ser Pro Glu Tyr Arg Gln Gln Ser Ala Val Pro Leu Asp Gly
                435                 440                 445
Glu Thr His Ala Gly Glu Asp Val Ala Val Phe Ala Arg Gly Pro Gln
```

```
                450                 455                 460
Ala His Leu Val His Gly Val Gln Glu Gln Thr Phe Ile Ala His Val
465                 470                 475                 480

Met Ala Phe Ala Ala Cys Leu Glu Pro Tyr Thr Ala Cys Asp Leu Ala
                485                 490                 495

Pro Arg Ala Gly Thr Thr Asp Ala Ala His Pro Gly Pro Ser Val Val
                500                 505                 510

Pro Ala Leu Leu Pro Leu Leu Ala Gly Thr Leu Leu Leu Leu Gly Thr
            515                 520                 525

Ala Thr Ala Pro
        530

<210> SEQ ID NO 17
<211> LENGTH: 535
<212> TYPE: PRT
<213> ORGANISM: Homo sapiens

<400> SEQUENCE: 17

Met Leu Gly Pro Cys Met Leu Leu Leu Leu Leu Leu Leu Gly Leu Arg
1               5                   10                  15

Leu Gln Leu Ser Leu Gly Ile Ile Pro Val Glu Glu Asn Pro Asp
            20                  25                  30

Phe Trp Asn Arg Glu Ala Ala Glu Ala Leu Gly Ala Ala Lys Lys Leu
        35                  40                  45

Gln Pro Ala Gln Thr Ala Ala Lys Asn Leu Ile Ile Phe Leu Gly Asp
    50                  55                  60

Gly Met Gly Val Ser Thr Val Thr Ala Ala Arg Ile Leu Lys Gly Gln
65                  70                  75                  80

Lys Lys Asp Lys Leu Gly Pro Glu Ile Pro Leu Ala Met Asp Arg Phe
                85                  90                  95

Pro Tyr Val Ala Leu Ser Lys Thr Tyr Asn Val Asp Lys His Val Pro
            100                 105                 110

Asp Ser Gly Ala Thr Ala Thr Ala Tyr Leu Cys Gly Val Lys Gly Asn
        115                 120                 125

Phe Gln Thr Ile Gly Leu Ser Ala Ala Ala Arg Phe Asn Gln Cys Asn
    130                 135                 140

Thr Thr Arg Gly Asn Glu Val Ile Ser Val Met Asn Arg Ala Lys Lys
145                 150                 155                 160

Ala Gly Lys Ser Val Gly Val Val Thr Thr Thr Arg Val Gln His Ala
                165                 170                 175

Ser Pro Ala Gly Thr Tyr Ala His Thr Val Asn Arg Asn Trp Tyr Ser
            180                 185                 190

Asp Ala Asp Val Pro Ala Ser Ala Arg Gln Glu Gly Cys Gln Asp Ile
        195                 200                 205

Ala Thr Gln Leu Ile Ser Asn Met Asp Ile Asp Val Ile Leu Gly Gly
    210                 215                 220

Gly Arg Lys Tyr Met Phe Arg Met Gly Thr Pro Asp Pro Glu Tyr Pro
225                 230                 235                 240

Asp Asp Tyr Ser Gln Gly Gly Thr Arg Leu Asp Gly Lys Asn Leu Val
                245                 250                 255

Gln Glu Trp Leu Ala Lys Arg Gln Gly Ala Arg Tyr Val Trp Asn Arg
            260                 265                 270

Thr Glu Leu Met Gln Ala Ser Leu Asp Pro Ser Val Thr His Leu Met
        275                 280                 285
```

```
Gly Leu Phe Glu Pro Gly Asp Met Lys Tyr Glu Ile His Arg Asp Ser
    290                 295                 300

Thr Leu Asp Pro Ser Leu Met Glu Met Thr Glu Ala Ala Leu Arg Leu
305                 310                 315                 320

Leu Ser Arg Asn Pro Arg Gly Phe Phe Leu Phe Val Glu Gly Gly Arg
                325                 330                 335

Ile Asp His Gly His His Glu Ser Arg Ala Tyr Arg Ala Leu Thr Glu
            340                 345                 350

Thr Ile Met Phe Asp Asp Ala Ile Glu Arg Ala Gly Gln Leu Thr Ser
        355                 360                 365

Glu Glu Asp Thr Leu Ser Leu Val Thr Ala Asp His Ser His Val Phe
370                 375                 380

Ser Phe Gly Gly Tyr Pro Leu Arg Gly Ser Ser Ile Phe Gly Leu Ala
385                 390                 395                 400

Pro Gly Lys Ala Arg Asp Arg Lys Ala Tyr Thr Val Leu Leu Tyr Gly
                405                 410                 415

Asn Gly Pro Gly Tyr Val Leu Lys Asp Gly Ala Arg Pro Asp Val Thr
            420                 425                 430

Glu Ser Glu Ser Gly Ser Pro Glu Tyr Arg Gln Gln Ser Ala Val Pro
        435                 440                 445

Leu Asp Glu Glu Thr His Ala Gly Glu Asp Val Ala Val Phe Ala Arg
450                 455                 460

Gly Pro Gln Ala His Leu Val His Gly Val Gln Glu Gln Thr Phe Ile
465                 470                 475                 480

Ala His Val Met Ala Phe Ala Ala Cys Leu Glu Pro Tyr Thr Ala Cys
                485                 490                 495

Asp Leu Ala Pro Pro Ala Gly Thr Thr Asp Ala Ala His Pro Gly Arg
            500                 505                 510

Ser Val Val Pro Ala Leu Leu Pro Leu Leu Ala Gly Thr Leu Leu Leu
        515                 520                 525

Leu Glu Thr Ala Thr Ala Pro
530                 535

<210> SEQ ID NO 18
<211> LENGTH: 532
<212> TYPE: PRT
<213> ORGANISM: Homo sapiens

<400> SEQUENCE: 18

Met Gln Gly Pro Trp Val Leu Leu Leu Gly Leu Arg Leu Gln Leu
1               5                   10                  15

Ser Leu Gly Ile Ile Pro Val Glu Glu Glu Asn Pro Asp Phe Trp Asn
                20                  25                  30

Arg Gln Ala Ala Glu Ala Leu Gly Ala Ala Lys Lys Leu Gln Pro Ala
            35                  40                  45

Gln Thr Ala Ala Lys Asn Leu Ile Ile Phe Leu Gly Asp Gly Met Gly
        50                  55                  60

Val Ser Thr Val Thr Ala Ala Arg Ile Leu Lys Gly Gln Lys Lys Asp
65                  70                  75                  80

Lys Leu Gly Pro Glu Thr Phe Leu Ala Met Asp Arg Phe Pro Tyr Val
                85                  90                  95

Ala Leu Ser Lys Thr Tyr Ser Val Asp Lys His Val Pro Asp Ser Gly
            100                 105                 110

Ala Thr Ala Thr Ala Tyr Leu Cys Gly Val Lys Gly Asn Phe Gln Thr
        115                 120                 125
```

```
Ile Gly Leu Ser Ala Ala Ala Arg Phe Asn Gln Cys Asn Thr Thr Arg
    130                 135                 140

Gly Asn Glu Val Ile Ser Val Met Asn Arg Ala Lys Lys Ala Gly Lys
145                 150                 155                 160

Ser Val Gly Val Val Thr Thr Thr Arg Val Gln His Ala Ser Pro Ala
                165                 170                 175

Gly Ala Tyr Ala His Thr Val Asn Arg Asn Trp Tyr Ser Asp Ala Asp
            180                 185                 190

Val Pro Ala Ser Ala Arg Gln Glu Gly Cys Gln Asp Ile Ala Thr Gln
        195                 200                 205

Leu Ile Ser Asn Met Asp Ile Asp Val Ile Leu Gly Gly Gly Arg Lys
    210                 215                 220

Tyr Met Phe Pro Met Gly Thr Pro Asp Pro Glu Tyr Pro Asp Asp Tyr
225                 230                 235                 240

Ser Gln Gly Gly Thr Arg Leu Asp Gly Lys Asn Leu Val Gln Glu Trp
                245                 250                 255

Leu Ala Lys His Gln Gly Ala Arg Tyr Val Trp Asn Arg Thr Glu Leu
            260                 265                 270

Leu Gln Ala Ser Leu Asp Pro Ser Val Thr His Leu Met Gly Leu Phe
        275                 280                 285

Glu Pro Gly Asp Met Lys Tyr Glu Ile His Arg Asp Ser Thr Leu Asp
    290                 295                 300

Pro Ser Leu Met Glu Met Thr Glu Ala Ala Leu Leu Leu Leu Ser Arg
305                 310                 315                 320

Asn Pro Arg Gly Phe Phe Leu Phe Val Glu Gly Gly Arg Ile Asp His
                325                 330                 335

Gly His His Glu Ser Arg Ala Tyr Arg Ala Leu Thr Glu Thr Ile Met
            340                 345                 350

Phe Asp Asp Ala Ile Glu Arg Ala Gly Gln Leu Thr Ser Glu Glu Asp
        355                 360                 365

Thr Leu Ser Leu Val Thr Ala Asp His Ser His Val Phe Ser Phe Gly
    370                 375                 380

Gly Tyr Pro Leu Arg Gly Ser Ser Ile Phe Gly Leu Ala Pro Gly Lys
385                 390                 395                 400

Ala Arg Asp Arg Lys Ala Tyr Thr Val Leu Leu Tyr Gly Asn Gly Pro
                405                 410                 415

Gly Tyr Val Leu Lys Asp Gly Ala Arg Pro Asp Val Thr Glu Ser Glu
            420                 425                 430

Ser Gly Ser Pro Glu Tyr Arg Gln Gln Ser Ala Val Pro Leu Asp Gly
        435                 440                 445

Glu Thr His Ala Gly Glu Asp Val Ala Val Phe Ala Arg Gly Pro Gln
    450                 455                 460

Ala His Leu Val His Gly Val Gln Glu Gln Thr Phe Ile Ala His Val
465                 470                 475                 480

Met Ala Phe Ala Ala Cys Leu Glu Pro Tyr Thr Ala Cys Asp Leu Ala
                485                 490                 495

Pro Arg Ala Gly Thr Thr Asp Ala Ala His Pro Gly Pro Ser Val Val
            500                 505                 510

Pro Ala Leu Leu Pro Leu Leu Ala Gly Thr Leu Leu Leu Leu Gly Thr
        515                 520                 525

Ala Thr Ala Pro
    530
```

```
<210> SEQ ID NO 19
<211> LENGTH: 528
<212> TYPE: PRT
<213> ORGANISM: Homo sapiens

<400> SEQUENCE: 19

Met Gln Gly Pro Trp Val Leu Leu Leu Leu Gly Leu Arg Leu Gln Leu
1               5                   10                  15

Ser Leu Gly Val Ile Pro Ala Glu Glu Asn Pro Ala Phe Trp Asn
            20                  25                  30

Arg Gln Ala Ala Glu Ala Leu Asp Ala Ala Lys Lys Leu Gln Pro Ile
            35                  40                  45

Gln Lys Val Ala Lys Asn Leu Ile Leu Phe Leu Gly Asp Gly Leu Gly
        50                  55                  60

Val Pro Thr Val Thr Ala Thr Arg Ile Leu Lys Gly Gln Lys Asn Gly
65                  70                  75                  80

Lys Leu Gly Pro Glu Thr Pro Leu Ala Met Asp Arg Phe Pro Tyr Leu
                85                  90                  95

Ala Leu Ser Lys Thr Tyr Asn Val Asp Arg Gln Val Pro Asp Ser Ala
            100                 105                 110

Ala Thr Ala Thr Ala Tyr Leu Cys Gly Val Lys Ala Asn Phe Gln Thr
            115                 120                 125

Ile Gly Leu Ser Ala Ala Arg Phe Asn Gln Cys Asn Thr Thr Arg
        130                 135                 140

Gly Asn Glu Val Ile Ser Val Met Asn Arg Ala Lys Gln Ala Gly Lys
145                 150                 155                 160

Ser Val Gly Val Val Thr Thr Thr Arg Val Gln His Ala Ser Pro Ala
                165                 170                 175

Gly Thr Tyr Ala His Thr Val Asn Arg Asn Trp Tyr Ser Asp Ala Asp
            180                 185                 190

Met Pro Ala Ser Ala Arg Gln Glu Gly Cys Gln Asp Ile Ala Thr Gln
            195                 200                 205

Leu Ile Ser Asn Met Asp Ile Asp Val Ile Leu Gly Gly Gly Arg Lys
        210                 215                 220

Tyr Met Phe Pro Met Gly Thr Pro Asp Pro Glu Tyr Pro Ala Asp Ala
225                 230                 235                 240

Ser Gln Asn Gly Ile Arg Leu Asp Gly Lys Asn Leu Val Gln Glu Trp
                245                 250                 255

Leu Ala Lys His Gln Gly Ala Trp Tyr Val Trp Asn Arg Thr Glu Leu
            260                 265                 270

Met Gln Ala Ser Leu Asp Gln Ser Val Thr His Leu Met Gly Leu Phe
            275                 280                 285

Glu Pro Gly Asp Thr Lys Tyr Glu Ile His Arg Asp Pro Thr Leu Asp
        290                 295                 300

Pro Ser Leu Met Glu Met Thr Glu Ala Ala Leu Arg Leu Leu Ser Arg
305                 310                 315                 320

Asn Pro Arg Gly Phe Tyr Leu Phe Val Glu Gly Gly Arg Ile Asp His
                325                 330                 335

Gly His His Glu Gly Val Ala Tyr Gln Ala Leu Thr Glu Ala Val Met
            340                 345                 350

Phe Asp Asp Ala Ile Glu Arg Ala Gly Gln Leu Thr Ser Glu Glu Asp
            355                 360                 365

Thr Leu Thr Leu Val Thr Ala Asp His Ser His Val Phe Ser Phe Gly
        370                 375                 380
```

Gly Tyr Thr Leu Arg Gly Ser Ser Ile Phe Gly Leu Ala Pro Ser Lys
385                 390                 395                 400

Ala Gln Asp Ser Lys Ala Tyr Thr Ser Ile Leu Tyr Gly Asn Gly Pro
                405                 410                 415

Gly Tyr Val Phe Asn Ser Gly Val Arg Pro Asp Val Asn Glu Ser Glu
            420                 425                 430

Ser Gly Ser Pro Asp Tyr Gln Gln Gln Ala Ala Val Pro Leu Ser Ser
        435                 440                 445

Glu Thr His Gly Gly Glu Asp Val Ala Val Phe Ala Arg Gly Pro Gln
450                 455                 460

Ala His Leu Val His Gly Val Gln Glu Gln Ser Phe Val Ala His Val
465                 470                 475                 480

Met Ala Phe Ala Ala Cys Leu Glu Pro Tyr Thr Ala Cys Asp Leu Ala
                485                 490                 495

Pro Pro Ala Cys Thr Thr Asp Ala Ala His Pro Val Ala Ala Ser Leu
            500                 505                 510

Pro Leu Leu Ala Gly Thr Leu Leu Leu Gly Ala Ser Ala Ala Pro
        515                 520                 525

<210> SEQ ID NO 20
<211> LENGTH: 227
<212> TYPE: PRT
<213> ORGANISM: Artificial Sequence
<220> FEATURE:
<223> OTHER INFORMATION: Synthetic Construct

<400> SEQUENCE: 20

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

-continued

```
Asp Lys Ser Arg Trp Gln Gln Gly Asn Val Phe Ser Cys Ser Val Met
    195                 200                 205

His Glu Ala Leu His Asn His Tyr Thr Gln Lys Ser Leu Ser Leu Ser
    210                 215                 220

Pro Gly Lys
225
```

TREATING MUSCLE WEAKNESS WITH ALKALINE PHOSPHATASES

SEQUENCE LISTING

The amino acid sequences listed in the accompanying sequence listing are shown using standard three-letter code for amino acids, as defined in 37 C.F.R. 1.822. The Sequence Listing is submitted as an ASCII text file, created on Mar. 30, 2017, about 84 KB, which is incorporated by reference herein.

BACKGROUND

Hypophosphatasia (HPP) is a rare, heritable skeletal disease with an incidence of 1 per 100,000 births for the most severe forms of the disease. HPP is often fatal when observed at birth, having an infant mortality rate of ~70%. Severely affected patients often die in infancy from respiratory insufficiency due to progressive chest deformity.

HPP can result from loss-of-function mutations in the gene coding for tissue-nonspecific alkaline phosphatase (TNALP). HPP leads to a remarkable range of symptoms and severity, from rickets (osteomalacia) to almost complete absence of bone mineralization in utero. Most patients exhibit the characteristics of skeletal changes, short stature, painful lower limbs, gait disturbance, and premature shedding of teeth. For instance, infantile symptoms of HPP can include inadequate weight gain, the appearance of rickets, impaired skeletal mineralization, progressive skeletal demineralization, rib fractures, and chest deformity, while childhood symptoms of HPP can include short stature and skeletal deformities, such as bowed legs and enlarged wrists, knees, and ankles as a result of flared metaphyses. Muscle weakness (or hypotonia) is also an important symptom associated with HPP. Due to physical impairments associated with HPP, patients afflicted with HPP often exhibit a decreased ability or inability to perform routine activities that healthy patients perform on a daily basis without requiring assistance.

Hypotonia in HPP has been asserted, without data, to be a result of PPi toxicity (Whyte, M.; *J. Bone Mineral Res.* (January 2017)). One paper showed PPi was able to disrupt actin/myosin interactions in a *bovine muscle model* (*Meat Science* 84: 364-370 (2010)). However, specific data on muscle weakness and PPi/ALP levels has not been available. Early data implicated skeletal changes (with a focus on Radiographic Global Impression of Change (RGI-C), but failed to isolate muscle weakness from the phenotypic heterogeneity of HPP.

Notably, the treatment of HPP, particularly the outgoing impairments associated with HPP such as muscle weakness, for an extended period of time, is unknown. Thus, there exists a need for methods that can be used to treat muscle weakness associated with HPP or with other diseases. There additionally exists a need for methods of treatment of hypotonia or muscle weakness in human subjects, as caused by or associated with elevated PPi and/or low alkaline phosphatase activity.

SUMMARY

Muscle weakness has been reported as a symptom in some patients with HPP and in other diseases or disorders. In HPP, elevated PPi concentration is due to loss of function mutation(s) in the gene ALPL that encodes the tissue non-specific isozyme of alkaline phosphatase (TNALP; a.k.a. liver/bone/kidney type ALP), which is an enzyme for substrates such as inorganic pyrophosphate (PPi), phosphoethanolamine (PEA) and pyridoxal 5'-phosphate (PLP). The instant disclosure teaches methods of treating a muscle weakness disease in a subject characterized with an elevated pyrophosphate (PPi) concentration and/or decreased alkaline phosphatase concentration.

The muscle weakness phenotype of HPP patients may be considered as secondary and caused by the bone mineralization defects, which is taken as the characteristic feature of HPP. Surprisingly, the instant disclosure teaches that muscle weakness in HPP is probably not due to the bone defect, since no difference among the muscles from wild type (WT) mice and AKP2$^{-/-}$ mice were observed in their soleus fiber type proportions or soleus or EDL muscle contractile properties ex vivo. On the contrary, muscle weakness in HPP was found to be more correlated to the elevated PPi concentration, since reducing PPi by administering asfotase alfa improved AKP2$^{-/-}$ mice muscle grip strength. Thus, a subject having a muscle weakness disease characterized by elevated PPi concentration, even without other HPP symptoms or not being diagnosed with HPP yet, may still be treated by asfotase alfa. Methods of testing grip strength have been disclosed, see, e.g., Whyte, M. et al., *Bone* 2016 December; 93: 125-138; Whyte, M., et al. *JCI Insight* 2016; 27:87-102; Whyte, M. et al., *Bone* 2015 June; 75: 229-39.

Disclosed are (1) methods to identify subjects (e.g., humans) having or being prone to a muscle weakness disease for treatment with a recombinant polypeptide having alkaline phosphatase activity (such as TNALP, for example the sALP polypeptide of SEQ ID NO: 1 or a polypeptide variant having at least 95% sequence identity to the sequence of SEQ ID NO: 1, e.g., asfotase alfa), and (2) treatment of such subjects with a recombinant polypeptide having alkaline phosphatase activity. Exemplary metrics useful for evaluating the need for or the efficacy of treatment using a recombinant polypeptide having alkaline phosphatase activity include (1) plasma PPi and/or alkaline phosphatase concentration, (2) the Bruininks-Oseretsky Test of Motor Proficiency 2nd Edition (BOT-2), (3) the Childhood Health Assessment Questionnaire (CHAQ), (4) the Pediatric Outcomes Data Collection Instrument (PODCI), (5) Bayley Scales of Infant and Toddler Development, 3$^{rd}$ Edition (BSID-III), (6) the Peabody Developmental Motor Scales, 2nd Edition (PDMS-2), (7) the Six Minute Walk Test (6 MWT), (8) the Muscle Strength Grade, and (9) Hand Held Dynamometry (HHD). The methods further include the use of one or more of the described metrics (e.g., plasma PPi concentration, alkaline phosphatase concentration, the BOT-2, the CHAQ, the PODCI, the BSID-III, the PDMS-2, the 6 MWT, the Muscle Strength Grade, and HHD) singly or in any combination to assess treatment efficacy using a recombinant polypeptide having alkaline phosphatase activity in a subject having or being prone to a muscle weakness disease in which improvements relative to a certain score or value demonstrate that the recombinant polypeptide having alkaline phosphatase activity is effective for treating a muscle weakness disease.

In one aspect, the instant disclosure provides a method of treating or ameliorating a muscle weakness in a subject having or being prone to a muscle weakness disease, comprising administering to said subject a therapeutically effective amount of at least one recombinant polypeptide having alkaline phosphatase activity. In some embodiments, said subject has an elevated concentration of inorganic pyrophosphate (PPi) and/or low alkaline phosphatase activity or concentration. In one embodiment, said subject has an elevated serum concentration of inorganic pyrophosphate (PPi). In other embodiments, said subject has an elevated concentration of at least one alkaline phosphatase substrate (e.g., PPi, PLP, PEA, etc.).

In another aspect, the instant disclosure also provides a method of identifying a subpopulation of subjects having or being prone to a muscle weakness disease, wherein the subjects in said subpopulation have an elevated inorganic pyrophosphate (PPi) concentration.

In some embodiments, a muscle of said subject is not significantly different from a muscle of a normal subject without said muscle weakness disease in at least one property of such muscle. Such property may be selected from muscle fiber type proportion, fiber contractile properties, or other muscle properties known in the art. Such muscles may include any muscle of the subject, including, e.g., skeletal or striated muscles, cardiac muscles, or smooth muscles. In some embodiments, such muscles include at least one type of arm and leg muscles, particularly at least one type of muscles selected from soleus and extensor digitorum longus (EDL) muscles.

In some embodiments, the muscle weakness disease described herein is caused by an elevated concentration of inorganic pyrophosphate (PPi), such as a PPi concentration of greater than about 4.5 µM. In one embodiment, the muscle weakness disease described herein is caused by an elevated serum concentration of inorganic pyrophosphate (PPi). For example, an elevated concentration of PPi in a sample (e.g., a plasma sample) from an infant or child (e.g., a subject less than about 12 years of age) may be about 5.71 µM or greater, an elevated concentration of PPi in a sample (e.g., a plasma sample) from an adolescent (e.g., a subject of about 13 to about 18 years of age) may be about 4.78 µM or greater; and an elevated concentration of PPi in a sample (e.g., a plasma sample) from an adult (e.g., a subject of greater than 18 years of age) may be about 5.82 µM or greater. In other embodiments, the muscle weakness disease described herein is caused by an elevated concentration of at least one alkaline phosphatase substrate (e.g., PPi, PLP, PEA, etc.). In some embodiments, an elevated concentration of pyrophosphate (PPi) enhances the muscle weakness disease described herein in said subject. In one embodiment, an elevated serum concentration of PPi enhances the muscle weakness disease described herein in said subject. For example, an elevated serum concentration of inorganic PPi that enhances the muscle weakness disease can be, e.g., about 5.71 µM or greater in a sample (e.g., a plasma sample) from an infant or child (e.g., a subject less than about 12 years of age), about 4.78 µM or greater in a sample (e.g., a plasma sample) from an adolescent (e.g., a subject of about 13 to about 18 years of age); and about 5.82 µM or greater in a sample (e.g., a plasma sample) from an adult (e.g., a subject of greater than about 18 years of age).

In some embodiments, the muscle weakness disease is caused or enhanced by a low alkaline phosphatase concentration in the subject. For example, the low alkaline phosphatase concentration in a sample (e.g., a plasma sample) from the subject may be, e.g., about 90 U/L or less for a subject of 0 to 14 days of age; about 134 U/L or less for a subject of 15 days of age to less than 1 year of age; about 156 U/L or less for a subject of about 1 year of age to less than 10 years of age; about 141 U/L or less for a subject of about 10 years of age to less than about 13 years of age; about 62 U/L or less for a female subject of about 13 years of age to less than about 15 years of age; about 127 U/L or less for a male subject of about 13 years of age to less than about 15 years of age; about 54 U/L or less for a female subject of about 15 years of age to less than about 17 years of age; about 89 U/L or less for a male subject of about 15 years of age to less than about 17 years of age; about 48 U/L or less for a female subject of about 17 years of age or older; or about 59 U/L or less for a male subject of about 17 years of age or older.

In other embodiments, an elevated concentration of at least one alkaline phosphatase substrate (e.g., PPi, PLP, PEA, etc.) enhances the muscle weakness disease described herein in said subject.

The muscle weakness disease described herein includes at least one of, e.g., hypophosphatasia (HPP), calcium pyrophosphate dihydrate crystal deposition (CPPD), familial hypophosphatemia (such as autosomal dominant hypophosphatemic rickets (ADHR), autosomal recessive hypophosphatemic rickets, X-linked hypophosphatemic rickets, X-linked hypophosphatemia (XLH), etc.), or other diseases having a muscle weakness phenotype and an elevated concentration of at least one alkaline phosphatase substrate (e.g., PPi, PLP, PEA, etc.). In one embodiment, the muscle weakness disease described herein includes at least one of, e.g., hypophosphatasia (HPP), calcium pyrophosphate dihydrate crystal deposition (CPPD), familial hypophosphatemia (such as autosomal dominant hypophosphatemic rickets (ADHR), autosomal recessive hypophosphatemic rickets, X-linked hypophosphatemic rickets, X-linked hypophosphatemia (XLH), etc.), or other diseases having a muscle weakness phenotype and an elevated concentration (e.g., serum concentration) of inorganic pyrophosphate (PPi).

In some embodiments, administration of at least one recombinant polypeptide having alkaline phosphatase activity (such as TNALP, for example the sALP polypeptide of SEQ ID NO: 1 or a polypeptide variant having at least 95% sequence identity to the sequence of SEQ ID NO: 1, e.g., asfotase alfa) reduces the concentration of PPi in a sample (e.g., a plasma sample) from said subject. For example, administration of the at least one recombinant polypeptide having alkaline phosphatase activity to the subject reduces the concentration of PPi in a sample (e.g., a plasma sample) to less than about 5.71 µM for an infant or child (e.g., a plasma PPi concentration of about 3.5 µM, about 4 µM, about 4.5 µM, about 5 µM, or about 5.5 µM or a plasma PPi concentration within the range of about 3.5 µM to about 5.5 µM); less than about 4.78 µM for an adolescent (e.g., a plasma PPi concentration of about 3.5 µM, about 4 µM, or about 4.5 µM, or a plasma PPi concentration within the range of about 3.5 µM to about 4.5 µM); or less than about 5.82 µM for an adult (e.g., a plasma PPi concentration of about 3.5 µM, about 4 µM, about 4.5 µM, about 5 µM, or about 5.5 µM or a plasma PPi concentration within the range of about 3.5 µM to about 5.5 µM).

In another aspect, the instant disclosure also provides a method, comprising: (i) identifying a population of subjects having or being prone to a muscle weakness disease; (ii) identifying a subpopulation of subjects among the population in step (i) wherein: (a) the subjects in said subpopulation have an elevated concentration of inorganic pyrophosphate (PPi); (b) an elevated concentration of inorganic pyrophosphate (PPi) that enhances muscle weakness in the subjects in said subpopulation; or (c) both (a) and (b); and (iii) treating said subpopulation in step (ii).

In another aspect, the instant disclosure also provides a method comprising: (i) identifying a population of subjects having or being prone to a muscle weakness disease; (ii) identifying a subpopulation of subjects among the population in step (i) wherein: (a) the subjects in said subpopulation have an elevated concentration of inorganic pyrophosphate (PPi); (b) an elevated concentration of inorganic pyrophosphate (PPi) that enhances muscle weakness in the subjects in said subpopulation; or (c) both (a) and (b); and (iii) treating or ameliorating at least one symptom of the muscle weakness disease of a subject in the subpopulation in step (ii), comprising administering to said subject a therapeutically effective amount of at least one recombinant polypeptide having alkaline phosphatase activity. In one embodiment, said subjects in the subpopulation have an elevated serum concentration of inorganic pyrophosphate (PPi).

In some embodiments, the muscle of the subject in step (iii) described herein is not significantly different from the muscle of a normal subject without said type of muscle weakness in at least one property of the muscle. In one embodiment, the at least one property of the muscle includes, e.g., fiber type proportion and/or fiber contractile properties. Such muscles may include any muscle of the subject, including, e.g., skeletal or striated muscles, cardiac muscles, or smooth muscles. In some embodiments, such muscles include at least one type of arm and/or leg muscles, particularly at least one type of muscle selected from soleus and extensor digitorum longus (EDL) muscle. In some embodiments, the method includes identifying a subject having or being prone to a muscle weakness disease and having an elevated concentration of PPi, an elevated concentration of alkaline phosphatase, decreased grip strength, an average BOT-2 strength score of, e.g., less than 10, an average BOT-2 running speed and agility score of, e.g., less than 5, an average CHAQ index score of, e.g., greater than about 0.8, an average PODCI score of, e.g., less than about 40, an average 6 MWT of, e.g., less than about 80% of the predicted 6 MWT value, and/or a Muscle Strength Grade of, e.g., less than 5.

For example, an elevated concentration of PPi in a sample (e.g., a plasma sample) from an infant or child (e.g., a subject less than about 12 years of age) may be about 5.71 µM or greater, an elevated concentration of PPi in a sample (e.g., a plasma sample) from an adolescent (e.g., a subject of about 13 to about 18 years of age) may be about 4.78 µM or greater; and an elevated concentration of PPi in a sample (e.g., a plasma sample) from an adult (e.g., a subject of greater than about 18 years of age) may be about 5.82 µM or greater. Additionally, an elevated concentration of alkaline phosphatase in a sample (e.g., a plasma sample) from the subject may be, about 90 U/L or less for a subject of 0 to 14 days of age; about 134 U/L or less for a of 15 days of age to less than 1 year of age; about 156 U/L or less for a subject of about 1 year of age to less than 10 years of age; about 141 U/L or less for a subject of about 10 years of age to less than about 13 years of age; about 62 U/L or less for a female subject of about 13 years of age to less than about 15 years of age; about 127 U/L or less for a male subject of about 13 years of age to less than about 15 years of age; about 54 U/L or less for a female subject of about 15 years of age to less than about 17 years of age; about 89 U/L or less for a male subject of about 15 years of age to less than about 17 years of age; about 48 U/L or less for a female subject of about 17 years of age or older; or about 59 U/L or less for a male subject of about 17 years of age or older.

In some embodiments, the muscle weakness disease described herein is caused by an elevated concentration of inorganic pyrophosphate (PPi). In one embodiment, the muscle weakness disease described herein is caused by an elevated serum concentration of inorganic pyrophosphate (PPi). For example, an elevated concentration of PPi in a sample (e.g., a plasma sample) from an infant or child (e.g., a subject less than about 12 years of age) may be about 5.71 µM or greater, an elevated concentration of PPi in a sample (e.g., a plasma sample) from an adolescent (e.g., a subject of about 13 to about 18 years of age) may be about 4.78 µM or greater; and an elevated concentration of PPi in a sample (e.g., a plasma sample) from an adult (e.g., a subject of greater than about 18 years of age) may be about 5.82 µM. In other embodiments, the muscle weakness disease described herein is caused by an elevated concentration of at least one alkaline phosphatase substrate (e.g., PPi, PLP, PEA, etc.).

In some embodiments, an elevated concentration of pyrophosphate (PPi) enhances the muscle weakness disease described herein in said subject in step (iii) described herein. In one embodiment, an elevated serum concentration of inorganic pyrophosphate (PPi) enhances the muscle weakness disease described herein in said subject. For example, an elevated concentration of PPi in a sample (e.g., a plasma sample) from an infant or child (e.g., a subject less than about 12 years of age) may be about 5.71 µM or greater, an elevated concentration of PPi in a sample (e.g., a plasma sample) from an adolescent (e.g., a subject of about 13 to about 18 years of age) may be about 4.78 µM or greater; and an elevated concentration of PPi in a sample (e.g., a plasma sample) from an adult (e.g., a subject of greater than about 18 years of age) may be about 5.82 µM In other embodiments, by an elevated concentration of at least one alkaline phosphatase substrate (e.g., PPi. PLP, PEA, etc.) enhances the muscle weakness disease described herein in said subject.

The muscle weakness disease described herein for subpopulation selection includes at least one of, e.g., hypophosphatasia (HPP), calcium pyrophosphate dihydrate crystal deposition (CPPD), familial hypophosphatemia (such as autosomal dominant hypophosphatemic rickets (ADHR), autosomal recessive hypophosphatemic rickets, X-linked hypophosphatemic rickets, X-linked hypophosphatemia (XLH), etc.), or other diseases having a muscle weakness phenotype and an elevated concentration of at least one alkaline phosphatase substrate (e.g., PPi, PLP, PEA, etc.). In one embodiment, the muscle weakness disease described herein includes at least one of, e.g., hypophosphatasia (HPP), calcium pyrophosphate dihydrate crystal deposition (CPPD), familial hypophosphatemia (such as autosomal dominant hypophosphatemic rickets (ADHR), autosomal recessive hypophosphatemic rickets, X-linked hypophosphatemic rickets, X-linked hypophosphatemia (XLH), etc.), or other diseases having a muscle weakness phenotype and an elevated concentration (e.g., serum concentration) of inorganic pyrophosphate (PPi).

In some embodiments, administration of at least one recombinant polypeptide having alkaline phosphatase activity (such as TNALP, for example the sALP polypeptide of SEQ ID NO: 1 or a polypeptide variant having at least 95% sequence identity to the sequence of SEQ ID NO: 1, e.g., asfotase alfa) reduces the concentration of inorganic pyrophosphate (PPi) in a sample (e.g., a plasma sample) from said subject. For example, administration of the at least one recombinant polypeptide having alkaline phosphatase activity to the subject reduces the concentration of PPi in a sample (e.g., a plasma sample) to less than about 5.71 µM for an infant or child (e.g., a plasma PPi concentration of about 3.5 µM, about 4 µM, about 4.5 µM, about 5 µM, or about 5.5 µM or a plasma PPi concentration within the range of about 3.5 µM to about 5.5 µM); less than about 4.78 µM for an adolescent (e.g., a plasma PPi concentration of about 3.5 µM, about 4 µM, or about 4.5 µM, or a plasma PPi concentration within the range of about 3.5 µM to about 4.5

μM); or less than about 5.82 μM for an adult (e.g., a plasma PPi concentration of about 3.5 μM, about 4 μM, about 4.5 μM, about 5 μM, or about 5.5 μM or a plasma PPi concentration within the range of about 3.5 μM to about 5.5 μM).

In some embodiments, administration of at least one recombinant polypeptide having alkaline phosphatase activity (such as TNALP, for example the sALP polypeptide of SEQ ID NO: 1 or a polypeptide variant having at least 95% sequence identity to the sequence of SEQ ID NO: 1, e.g., asfotase alfa) increases the concentration of alkaline phosphatase in a sample (e.g., a plasma sample) from said subject. For example, administration of the at least one recombinant polypeptide having alkaline phosphatase activity increases the alkaline phosphatase concentration in a sample (e.g., a plasma sample) from the subject to, e.g., about 273 U/L or greater for a subject of 0 to 14 days of age; about 518 U/L or greater for a subject of 15 days of age to less than 1 year of age; about 369 U/L or greater for a subject of about 1 year of age to less than 10 years of age; about 460 U/L or greater for a subject of about 10 years of age to less than about 13 years of age; about 280 U/L or greater for a female subject of about 13 years of age to less than about 15 years of age; about 517 U/L or greater for a male subject of about 13 years of age to less than about 15 years of age; about 128 U/L or greater for a female subject of about 15 years of age to less than about 17 years of age; about 365 U/L or greater for a male subject of about 15 years of age to less than about 17 years of age; about 95 U/L or greater for a female subject of about 17 years of age or older; or about 164 U/L or greater for a male subject of about 17 years of age or older.

In some embodiments, the subject may also exhibit decreased reliance on an assistive mobility device (e.g., a walker, a wheelchair, braces, crutches, and orthotics) after administration of the at least one recombinant polypeptide having alkaline phosphatase activity.

In any of the above aspects, prior to administration of the at least one recombinant polypeptide having alkaline phosphatase activity, the subject is characterized as having an average Hand Held Dynamometry (HHD) value of less than about 80% of a predicted HHD value (e.g., relative to a normal subject of about the same age, the same gender, and/or the same height), in particular, in which the HHD value represents the grip strength, knee flexion, knee extension, hip flexion, hip extension, or hip abduction of the subject. For example, administration of the at least one recombinant polypeptide having alkaline phosphatase activity results in an average HHD value of the subject of about 50% or more of a predicted HHD value, e.g., in which the HHD value represents the grip strength, knee flexion, knee extension, hip flexion, hip extension, or hip abduction of the subject.

In some embodiments, the at least one recombinant polypeptide having alkaline phosphatase activity described herein is or can be administered to the subject daily, twice a week, once a week, or in even lower frequency. In one embodiment, the at least one recombinant polypeptide having alkaline phosphatase activity described herein is administered to the subject daily. The at least one recombinant polypeptide having alkaline phosphatase activity described herein can be administered to the subject for at least one week, two weeks, one month, three months, six months, one year, or a longer period, up to the whole life of the subject.

In some embodiments, the at least one recombinant polypeptide having alkaline phosphatase activity described herein is or can be administered by at least one route. Such routes include, e.g., subcutaneous, intravenous, intramuscular, sublingual, intrathecal, intradermal, or other routes known in the art. In one embodiment, the at least one recombinant polypeptide having alkaline phosphatase activity described herein is administered subcutaneously.

In some embodiments, the at least one recombinant polypeptide having alkaline phosphatase activity described herein comprises at least one of a tissue nonspecific alkaline phosphatase (TNALP), a placental alkaline phosphatase (PALP), a germ cell alkaline phosphatase (GCALP), an intestinal alkaline phosphatase (IALP), and biologically functional fragments, fusions, or chimeric constructs thereof. In one embodiment, the at least one recombinant polypeptide having alkaline phosphatase activity described herein comprises at least one of a soluble fragment of TNALP, PALP, GCALP, and IALP. In one embodiment, the tissue nonspecific alkaline phosphatase (TNALP) described herein comprises or consists of an amino acid sequence of the amino acids 1-485 of SEQ ID NO: 1. In another embodiment, the tissue nonspecific alkaline phosphatase (TNALP) described herein comprises or consists of an amino acid sequence of SEQ ID NO: 1.

In some embodiments, the at least one recombinant polypeptide having alkaline phosphatase activity described herein is a fusion protein. In one embodiment, the at least one recombinant polypeptide having alkaline phosphatase activity described herein comprise an immunoglobulin molecule. Such immunoglobulin molecule may be, e.g., a fragment crystallizable region (Fc), or a full-length, or fragment thereof of, an IgG, including but not limited to $IgG_1$, $IgG_2$, $IgG_3$, $IgG_4$, $IgG_{2/4}$, or other IgG fusions. In one embodiment, the Fc described herein comprises an amino acid sequence of SEQ ID NO: 20.

In some embodiments, the at least one recombinant polypeptide having alkaline phosphatase activity described herein comprises a negatively charged peptide. Such negatively charged peptide may include at least one poly(glutamic acid) (polyE) or a poly(aspartic acid) (polyD) peptide, e.g., the at least one recombinant polypeptide having alkaline phosphatase activity includes 6, 7, 8, 9, 10, 11, 12, 13, 14, 15, or 16 consecutive acidic residues, in particular, aspartic acid (D) or glutamic acid (E), such as at least one of $D_{10}$, $D_{16}$, $E_{10}$, and $E_{16}$. In some embodiments, the at least one recombinant polypeptide having alkaline phosphatase activity includes $E_6$, $E_7$, $E_8$, $E_9$, $E_{10}$, $E_{11}$, $E_{12}$, $E_{13}$, $E_{14}$, $E_{15}$, $E_{16}$, $D_6$, $D_7$, $D_8$, $D_9$, $D_{10}$, $D_{11}$, $D_{12}$, $D_{13}$, $D_{14}$, $D_{15}$, or $D_{16}$, e.g., $E_6$, $E_{10}$, $D_6$, or $D_{10}$.

In some embodiments, the at least one recombinant polypeptide having alkaline phosphatase activity described herein comprises a bone targeted alkaline phosphatase comprising a polypeptide having the structure: Z-sALP-Y-spacer-X-Wn-V, wherein sALP is the extracellular domain of the alkaline phosphatase; V is absent or is an amino acid sequence of at least one amino acid; X is absent or is an amino acid sequence of at least one amino acid; Y is absent or is an amino acid sequence of at least one amino acid; Z is absent or is an amino acid sequence of at least one amino acid; and Wn is a polyaspartate or a polyglutamate wherein n=10 to 16.

In some embodiments, the spacer described herein comprises a fragment crystallizable region (Fc). In one embodiment, the Fc described herein comprises an amino acid sequence of SEQ ID NO: 20.

In some embodiments, the at least one recombinant polypeptide having alkaline phosphatase activity described herein comprises a structure of sALP-Fc-$D_{10}$.

In one embodiment, the at least one recombinant polypeptide having alkaline phosphatase activity described herein comprises a dimer comprising monomers of an amino acid sequence of SEQ ID NO: 1.

In some embodiments, the at least one recombinant polypeptide having alkaline phosphatase activity described herein is administered in a dosage from about 0.1 mg/kg/day to about 20 mg/kg/day, or a comparable weekly dosage. In one embodiment, the at least one recombinant polypeptide having alkaline phosphatase activity described herein is administered in a dosage from about 0.5 mg/kg/day to about 20 mg/kg/day, or a comparable weekly dosage. In another embodiment, the at least one recombinant polypeptide having alkaline phosphatase activity described herein is administered in a dosage from about 0.5 mg/kg/day to about 10 mg/kg/day, or a comparable weekly dosage. In another embodiment, the at least one recombinant polypeptide having alkaline phosphatase activity described herein is administered in a dosage from about 1 mg/kg/day to about 10 mg/kg/day, or a comparable weekly dosage.

In some embodiments, the subject described herein is a mammal (e.g., a human).

Definitions

As used herein, "a" or "an" means "at least one" or "one or more" unless otherwise indicated. In addition, the singular forms "a", "an", and "the" include plural referents unless the context clearly dictates otherwise.

As used herein, "about" refers to an amount that is ±10% of the recited value and is preferably ±5% of the recited value, or more preferably ±2% of the recited value.

As used herein, "at least" refers to an amount that is ≤10% of the recited value and is preferably ≤5% of the recited value, or more preferably <2% of the recited value.

By "asfotase alfa" is meant a human TNALP (hTNALP) fusion protein formulated for the treatment of HPP. Asfotase alfa is a fusion protein including a soluble glycoprotein of two identical polypeptide chains, in which each polypeptide chain includes amino acid residues 1-726 of SEQ ID NO: 1. The structure of each polypeptide chain includes the catalytic domain of hTNALP, the human immunoglobulin Gi Fc domain, and a deca-aspartate peptide used as a bone targeting domain (the structure hTNALP-Fc-$D_{10}$). The two polypeptide chains are covalently linked by two disulfide bonds. Asfotase alfa has been approved under the trade name STRENSIQ® (Alexion Pharmaceuticals, Inc., New Haven, Conn.) in the United States, Europe, Japan, Canada, Israel, Australia, and Korea.

The terms "individual," "subject" and "patient" are used interchangeably and refer to any subject for whom diagnosis, treatment or therapy is desired, particularly humans. Other subjects may include, for example, cattle, dogs, cats, guinea pigs, rabbits, rats, mice, horses and the like. As used herein, an "at risk" subject or a subject "being prone to" a disease is a subject who is identified as having a risk of developing a disease, disorder or symptoms associated with a muscle weakness disease.

As used herein, "average" refers to a numerical value expressing the mean or median of a data set. The mean of a data set is calculated by dividing the sum of the values in the data set by their number. The median of a data set is calculated by determining the middle value in a list data of odd numbers or by determining the mean of the two data values in the middle in a list of even numbers.

The term "wild-type" "or "wild-type sequence" used for TNALP or other genes or proteins in the instant disclosure refers to the typical form of such genes or proteins as it occurs in nature in normal human, non-human mammals, or other living organisms. A wild-type sequence may refer to the standard "normal" allele at a locus for a gene or the standard "normal" primary amino acid sequence (optionally with the standard "normal" post-translational modifications to and/or inter-chain bonds and/or interactions among amino acid residues) for a polypeptide or protein, in contrast to that produced by a non-standard, "mutant" allele or amino acid sequence/modification/interaction. "Mutant" alleles can vary to a great extent, and even become the wild type if a genetic shift occurs within the population. It is now appreciated that most or all gene loci (and less frequently, but still possible, for most polypeptide sequences) exist in a variety of allelic forms, which vary in frequency throughout the geographic range of a species, and that a uniform wild type may not necessarily exist. In general, however, the most prevalent allele or amino acid sequence—i.e., the one with the highest frequency among normal individual human or other organisms—is the one deemed as wild type in the instant disclosure.

The term "normal" used for human or other organisms in this specification refers to, except for specified otherwise, a human or other organisms without any diseases (e.g., HPP), disorders, and/or symptoms or physiological consequences (e.g., muscle weakness) caused by or related to the aberrant activity (which may be due to, e.g., deficient or lack of gene or protein product and/or defective or loss-of-function of gene or protein product) of the relevant gene or polypeptide/protein. The most obvious example for a normal human is a human being who lacks muscle weakness or muscle weakness symptoms and lacks mutations or modifications to genes or proteins (e.g., the ALPL gene and ALP proteins) which may result in HPP-related muscle weakness. In another scenario focusing on ALP functions, the scope of a "normal" human in the present disclosure may be broadened to include any human beings having no aberrant endogenous alkaline phosphatase activity (which may be tested by, e.g., the substrate (PPi, PEA and PLP) levels and compared to the corresponding activity in other healthy or normal human beings).

As used herein, an "elevated" or "increased" concentration refers to a concentration (e.g., of PPi) in a subject having or being prone to a muscle weakness disease described herein which is higher than the concentration in a wild-type subject, in another subject without the muscle weakness disease, in the same subject at a time point when the subject has no such muscle weakness disease, or in the same subject should the subject have had no such muscle weakness disease. Such "elevated concentration" refers to an elevated concentration inside the subject described herein, including any cell, tissue, organ, or part of the subject. In one embodiment, such "elevated concentration" comprises an elevated concentration in the serum of the subject.

The terms "Bayley Scales of Infant and Toddler Development, $3^{rd}$ Edition" or "BSID-III" as used herein refer to a standardized series of measurements used to assess the motor (fine and gross), language (receptive and expressive), and cognitive development of patients. See Bayley, (2006). *Bayley scales of infant and toddler development: administration manual*. San Antonio, Tex.: Harcourt Assessment, hereby incorporated by reference in its entirety. The BSID-III measurements include a series of developmental play tasks to be administered to the patient. Raw scores of successfully completed items are converted to scaled scores. The scaled scores are then used to determine the patient's performance compared to healthy, age-adjusted patients. The BSID-III can also include the Social-Emotional Adaptive Behavior Questionnaire, which is completed by the parent/guardian, to establish the range of adaptive behaviors of the patient. For example, measurements for determining the BSID-III score (e.g., the BSID-III gross motor function score) can include prehension, perceptual-motor integration, motor planning and speed, visual tracking, reaching, object grasping, object manipulation, functional hand skills, responses to tactile information, movement of the limbs and torso, static positioning, dynamic movement, balance, and motor planning. These patient measurements are then converted into a BSID-III scaled score (e.g., the BSID-III gross motor function scaled score) ranging from 0 to 14, in which scores of about 7 to about 13 are considered the normal range of healthy patients.

The term "bone-targeting moiety," as used herein, refers to an amino acid sequence of between 1 and 50 amino acid residues in length having a sufficient affinity to the bone matrix, such that the bone-targeting moiety, singularly, has an in vivo binding affinity to the bone matrix of about $10^{-6}$ M to about $10^{-15}$ M (e.g., $10^{-7}$ M, $10^{-8}$ M, $10^{-9}$ M, $10^{-10}$ M, $10^{-11}$ M, $10^{-12}$ M, $10^{-13}$ M, $10^{-14}$ M, or $10^{-15}$ M).

The terms "Bruininks-Oseretsky Test of Motor Proficiency $2^{nd}$ Edition" or "BOT-2," as used herein, refer to the second edition of a standardized test of gross and fine motor performance for patients, e.g., from about 4 to about 21 years of age. See Bruininks, R. H. (2005). *Bruininks-Oseretsky Test of Motor Proficiency*, (BOT-2). Minneapolis, Minn.: Pearson Assessment, hereby incorporated by reference in its entirety. The BOT-2 is administered individually to assess gross and fine motor skills of a range of patients. In particular, the BOT-2 can be used to evaluate physical impairments and mobility restrictions in patients having HPP. The BOT-2 provides composite BOT-2 scores in the following areas: strength, running speed and agility, fine motor precision, fine motor integration, manual dexterity, bilateral coordination, balance, and upper-limb coordination. For example, a BOT-2 strength score can be determined by having a patient perform sit-ups, v-ups, standing long jump, wall sit, and push-ups. A running speed and agility score can be determined by having a patient step over a balance beam or perform a shuttle run, two-legged side hop, or one-legged side hop. Both BOT-2 strength and BOT-2 running speed and agility scores range from 0 to 25, in which a score of about 10 to 20 is considered representative of healthy patients.

The terms "Childhood Health Assessment Questionnaire" or "CHAQ," as used herein refer to a questionnaire that is used to assess the health status (e.g., ability to perform activities of daily living (ADLs) and incidence of pain) of patients of 1 to 19 years of age, such as patients with HPP. For a description of the CHAQ index, see Bruce & Fries (*J. Rheumatol.* 30(1): 167-178, 2003), hereby incorporated by reference in its entirety. The CHAQ may be administered by interview or self-report for children greater than 8 years of age. The CHAQ includes eight sub-scales for dressing/grooming, arising, eating, walking, hygiene, reach, grip, and activities. The range of scores within each category is from 0 to 3, in which a score of 0 indicates without any difficulty; a score of 1 indicates with some difficulty; a score of 2 indicates with much difficulty; and a score of 3 indicates that the patient is unable to perform the activity. The CHAQ index may also be used to determine the presence and severity of pain.

By "extracellular domain" is meant any functional extracellular portion of the native protein, e.g., alkaline phosphatase. In particular, the extracellular domain lacks the signal peptide.

By "Fc" is meant a fragment crystallizable region of an immunoglobulin, e.g., IgG-1, IgG-2, IgG-3, IgG-3 or IgG-4, including the CH2 and CH3 domains of the immunoglobulin heavy chain. Fc may also include any portion of the hinge region joining the Fab and Fc regions. The Fc can be of any mammal, including human, and may be post-translationally modified (e.g., by glycosylation). In a non-limiting example, Fc can be the fragment crystallizable region of human IgG-1 having the amino acid sequence of SEQ ID NO: 20.

By "fragment" is meant a portion of a polypeptide or nucleic acid molecule that contains, preferably, at least 10%, 20%, 30%, 40%, 50%, 60%, 70%, 75%, 80%, 85%, 90%, 95%, 96%, 97%, 98%, 99%, or more of the entire length of the reference nucleic acid molecule or polypeptide. A fragment may contain, e.g., 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 400, 500, 600, 700, or more amino acid residues, up to the entire length of the polypeptide. Exemplary sALP fragments have amino acid residues 18-498, 18-499, 18-500, 18-501, 18-502, 18-503, 18-504, 18-505, 18-506, 18-507, 18-508, 18-509, 18-510, 18-511, or 18-512 of a ALP (e.g., SEQ ID NOs: 2-6), and may include additional C-terminal and/or N-terminal portions.

The terms "Hand Held Dynamometry" and "HHD" as used interchangeably herein refer to a method to measure the grip and muscle strength of subjects, in particular, subjects having or being prone to a muscle weakness disease. A dynamometer can be used to assess grip strength, knee flexion, knee extension, hip flexion, hip extension, and hip abduction of a subject (e.g., a subject having or being prone to a muscle weakness disease). For example, knee flexion and extension and also hip flexion, extension, and abduction of a subject having or being prone to a muscle weakness disease can be measured using, e.g., a MICROFET2™ Dynamometer, while grip strength of the subject can be measured using, e.g., a Jamar Grip Dynamometer. In particular, the administrator holds the dynamometer stationary, and the subject exerts a maximal force against the dynamometer. Peak force data is collected in pounds, then converted to Newtons (N). Torque values are then calculated using limb length in N-meters. The torque value can then be compared to the value of, e.g., a normal subject of about the same age, the same gender, and/or the same height, and expressed as a percentage value to generate the HHD value of the subject.

The terms "hypophosphatasia" or "HPP," as used herein, refer to a rare, heritable skeletal disorder caused by, e.g., one or more loss-of-function mutations in the ALPL (alkaline phosphatase, liver/bone/kidney) gene, which encodes tissue-nonspecific alkaline phosphatase (TNALP). HPP may be further characterized as infantile HPP, childhood HPP, perinatal HPP (e.g., benign perinatal HPP or lethal perinatal HPP), or odonto-HPP.

By "naïve patient" or "naïve subject" is meant a patient or subject having a muscle weakness disease described herein that has never received treatment with an alkaline phosphatase, or a polypeptide having alkaline phosphatase activity, such as a sALP (e.g., TNALP, for example the sALP polypeptide of SEQ ID NO: 1 or a polypeptide variant having at least 95% sequence identity to the sequence of SEQ ID NO: 1, e.g., asfotase alfa).

By "pain" as used herein refers to physical suffering or discomfort caused by a muscle weakness disease described herein, such as muscle pain. For instance, symptoms of pain can include, e.g., soreness, tightness, or stiffness. The severity of pain can vary between patients (e.g., chronic pain or acute pain). In particular, chronic pain refers to pain that lasts longer than three to six months or pain that extend beyond the expected period of healing. In contrast, acute pain refers to pain that typically lasts less than three to six months. As described herein, therapeutic compositions (e.g., including a sALP, such as asfotase alfa) can be administered to a patient suffering from pain (e.g., muscle pain) in an amount sufficient to relieve or at least partially relieve the symptoms of pain (e.g., discomfort, soreness, tightness, or stiffness) and its complications (e.g., fatigue, sleeplessness, weakened immune system, depression, anxiety, stress, irritability, or disability).

The terms "peptide," "polypeptide," and "protein" are used interchangeably and refer to any chain of two or more natural or unnatural amino acid residues, regardless of post-translational modification (e.g., glycosylation or phosphorylation), constituting all or part of a naturally-occurring or non-naturally occurring polypeptide or peptide, as is described herein.

By "pharmaceutically acceptable carrier" or "pharmaceutically acceptable excipient" is meant at least one carrier or excipient, respectively, which is physiologically acceptable to the treated patient while retaining the therapeutic properties of the compound with which it is administered. One exemplary pharmaceutically acceptable carrier substance is physiological saline. For instance, the pharmaceutically acceptable carrier can include sodium chloride (e.g., 150 mM sodium chloride) and sodium phosphate (e.g., 25 mM sodium phosphate). Other physiologically acceptable carriers and their formulations are known to those skilled in the art and described, e.g., in Remington's Pharmaceutical Sciences (20th edition), A. Gennaro, Ed., 2000, Lippincott, Williams & Wilkins, Philadelphia, Pa.

By "pharmaceutical composition" is meant a composition containing a polypeptide or nucleic acid molecule as described herein formulated with at least one pharmaceutically acceptable excipient, diluent, or carrier. The pharmaceutical composition may be manufactured or sold with the approval of a governmental regulatory agency as part of a therapeutic regimen for the treatment or prevention of a disease or event in a patient. Pharmaceutical compositions can be formulated, for example, for subcutaneous administration, intravenous administration (e.g., as a sterile solution free of particulate emboli and in a solvent system suitable for intravenous use), for oral administration (e.g., a tablet, capsule, caplet, gelcap, or syrup), or any other formulation described herein, e.g., in unit dosage form. In one embodiment, the pharmaceutical composition of the present disclosure is subcutaneously administered or is formulated for subcutaneous administration.

The term "physical impairments," as used herein, refers to a physiological condition, such as bone weakness and muscle weakness diseases described herein that can restrict or eliminate, e.g., ambulation, functional endurance, and ability to perform activities of daily living (ADL) of a patient. In particular, physical impairments may restrict or eliminate a patient's ability to perform ADL, which are routine activities that healthy patients perform on a daily basis without requiring assistance, such as functional mobility or transferring (e.g., walking), bathing and showering, dressing, self-feeding, and personal hygiene and grooming. As described herein, therapeutic compositions (e.g., compositions including a sALP, such as asfotase alfa) can be administered to a patient to decrease the severity and/or frequency of physical impairments associated with muscle weakness.

The terms "Pediatric Outcomes Data Collection Instrument" or "PODCI," as used herein, refer to a questionnaire used to assess overall health, incidence of pain, and ability to perform ADLs of patients under 19 years of age, particularly in patients with chronic health disorders, such as patients with HPP. For a description of the PODCI, see Plint et al. (*J. Pediatr. Orthop.* 23(6): 788-790, 2003), hereby incorporated by reference in its entirety. The questionnaire may be completed by the patient or by a parent/guardian of the patient with knowledge of the patient's condition. The eight scales generated from the PODCI include the following: 1) the upper extremity and physical function scale to measure difficulty encountered in performing daily personal care and student activities; 2) the transfer and basic mobility scale to measure difficulty experienced in performing routine motion and motor activities in daily activities; 3) the sports/physical functioning scale to measure difficulty or limitations encountered in participating in more active activities or sports; 4) the pain/comfort scale to measure the level of pain experienced during the past week; 5) the treatment expectations scale to measure the long term expectations of treatment; 6) the happiness scale to measure overall satisfaction with personal looks and sense of similarity to friends and others of own age; 7) the satisfaction with symptoms scale to measure the patient's acceptance of current limitations should this be a life-long state; and 8) the global functioning scale, which is a general combined scale calculated from the first four scales listed above. Standardized scores are generated from a series of questions in the PODCI and converted to a 0 to 100 scale, in which 0 represents significant disability and 100 represents less disability.

The terms "Peabody Developmental Motor Scales, 2nd Edition" or "PDMS-2," as used herein, refer to an early childhood motor development program that provides an assessment of gross and fine motor skills in patients from birth throughout childhood (e.g., infants and children). For a description of the PDMS-2 scales, see van Hartingsveldt et al. (*Occup. Ther. Int.* 12(1): 1-13, 2005), hereby incorporated by reference in its entirety. The PDMS-2 is composed of six subtests that measure interrelated motor abilities of early development. The six subtests include the following: 1) the locomotor subtest to measures a patient's ability to move from one place to another (measurements include crawling, walking, running, hopping, and jumping forward); 2) the reflexes subtest to measure a patient's ability to automatically react to environmental events; 3) the stationary subtest to measure a patient's ability to sustain control of his or her body within the center of gravity and retain equilibrium; 4) the object manipulation subtest to measure a patient's ability to manipulate an object, such as catching, throwing, and kicking a ball; 5) the grasping subtest to measure a patient's ability to use his or her hands, such as the ability to hold an object with one hand and actions involving the controlled use of the fingers of both hands; and 6) the visual-motor integration subtest to measure a patient's ability to use his or her visual perceptual skills to perform complex eye-hand coordination tasks, such as reaching and grasping for an object, building with blocks, and copying designs. The PDMS-2 measurements for each subtest is converted into a PDMS-2 score, such as the PDMS-2 locomotor standard score ranging from 0 to 13, in which the range of health patients is from about 7 to about 13.

The terms "sALP," "soluble alkaline phosphatase," and "extracellular domain of an alkaline phosphatase" are used interchangeably and refer to a soluble, non-membrane-bound alkaline phosphatase or a domain, biologically active fragment, or biologically active variant thereof. sALPs include, for example, an alkaline phosphatase lacking a C-terminal glycolipid anchor (GPI signal sequence, e.g., polypeptides including or consisting of the amino acid residues 18-502 of a human TNALP (SEQ ID NOs: 2, 3, 4, 5, or 6)). In particular, a TNALP may include, e.g., a polypeptide including or consisting of amino acid residues 1-485 of SEQ ID NO: 1, such as asfotase alfa, or a polypeptide variant having at least 95% sequence identity to the amino acid residues 1-485 of SEQ ID NO: 1. sALPs further include, for example, mammalian orthologs of human TNALP, such as a rhesus TNALP (SEQ ID NO: 7), a rat TNALP (SEQ ID NO: 8), a canine TNALP (SEQ ID NO: 9), a porcine TNALP (SEQ ID NO: 10), a murine TNALP (SEQ ID NO: 11), a bovine TNALP (SEQ ID NOs: 12-14), or a feline TNALP (SEQ ID NO: 15). sALPs also include soluble, non-membrane-bound forms of human PALP (e.g., polypeptides including or consisting of amino acid residues 18-502 of SEQ ID NOs: 16 or 17), GCALP (e.g., polypeptides including or consisting of amino acid residues 18-502 of SEQ ID NO: 18), and IALP (e.g., polypeptides including or consisting of amino acid residues 18-502 of SEQ ID NO: 19), and additional variants and analogs thereof that retain alkaline phosphatase activity, e.g., the ability to hydrolyze PPi. A sALP, in particular, lacks the N-terminal signal peptide (e.g., aa 1-17 of SEQ ID NOs: 2-6, 8, 11-13, or 15 or aa 1-25 of SEQ ID NO: 7).

By "sALP polypeptide" is meant a polypeptide having the structure A-sALP-B, wherein sALP is as defined herein and each of A and B is absent or is an amino acid sequence of at least one amino acid. An exemplary sALP polypeptide has an amino acid sequence comprising or consisting of the amino acids 1-485 of SEQ ID NO: 1. Other exemplary sALP polypeptides include any sALP fusion polypeptides described herein (for example the sALP fusion polypeptide of SEQ ID NO: 1 or a polypeptide variant having at least 95% sequence identity to the sequence of SEQ ID NO: 1, e.g., asfotase alfa).

By "signal peptide" is meant a short peptide (5-30 amino acids long) at the N-terminus of a polypeptide that directs a polypeptide towards the secretory pathway (e.g., the extracellular space). The signal peptide is typically cleaved during secretion of the polypeptide. The signal sequence may direct the polypeptide to an intracellular compartment or organelle, e.g., the Golgi apparatus. A signal sequence may be identified by homology, or biological activity, to a peptide with the known function of targeting a polypeptide to a particular region of the cell. One of ordinary skill in the art can identify a signal peptide by using readily available software (e.g., Sequence Analysis Software Package of the Genetics Computer Group, University of Wisconsin Biotechnology Center, 1710 University Avenue, Madison, Wis. 53705, BLAST, or PILEUP/PRETTYBOX programs). A signal peptide can be one that is, for example, substantially identical to amino acid residues 1-17 of SEQ ID NOs: 2-6 or amino acid residues 1-25 of SEQ ID NO: 7.

As used herein, when a polypeptide or nucleic acid sequence is referred to as having "at least X % sequence identity" to a reference sequence, wherein "X" is a real number, it is meant that at least X percent of the amino acid residues or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith et al., *J. Mol. Biol.* 147:195-7, 1981) and BLAST (Basic Local Alignment Search Tool; Altschul et al., *J. Mol. Biol.* 215: 403-10, 1990). These and other alignment algorithms are accessible using publicly available computer software such as "Best Fit" (Smith and Waterman, *Advances in Applied Mathematics,* 482-489, 1981) as incorporated into GeneMatcher Plus (Schwarz and Dayhoff, Atlas of Protein Sequence and Structure, Dayhoff, M. O., Ed pp 353-358, 1979), BLAST, BLAST-2, BLAST-P, BLAST-N, BLAST-X, WU-BLAST-2, ALIGN, ALIGN-2, CLUSTAL, Megalign (DNASTAR), or other software/hardware for alignment. In addition, those skilled in the art can determine appropriate parameters for measuring alignment, including any algorithms needed to achieve optimal alignment over the length of the sequences being compared.

The terms "patient" and "subject" are used interchangeably and refer to a mammal, including, but not limited to, a human or a non-human mammal, such as a bovine, equine, canine, ovine, or feline.

By "therapeutically effective amount" is meant an amount of a polypeptide or nucleic acid molecule described herein that is sufficient to substantially improve, treat, prevent, delay, suppress, or arrest at least one symptom of HPP. A therapeutically effective amount of a composition described herein may depend on the severity of the disorder being treated and the condition, weight, and general state of the patient and can be determined by an ordinarily-skilled artisan with consideration of such factors. A therapeutically effective amount of a composition described herein can be administered to a patient in a single dose or in multiple doses administered over a period of time.

By "treating," "treat," or "treatment" is meant the medical management of a patient with the intent to cure, ameliorate, stabilize, reduce the likelihood of, or prevent a muscle weakness diseases (e.g., in a patient with HPP) and/or management of a patient exhibiting or likely to have a muscle weakness diseases (e.g., in a patient with HPP), e.g., by administering a pharmaceutical composition.

This term includes active treatment, that is, treatment directed specifically toward the improvement or associated with the cure of a disease, pathological condition, disorder, or event, and also includes causal treatment, that is, treatment directed toward removal of the cause of the associated disease, pathological condition, disorder, or event. In addition, this term includes palliative treatment, that is, treatment designed for the relief or improvement of at least one symptom rather than the curing of the disease, pathological condition, disorder, or event; symptomatic treatment, that is, treatment directed toward constitutional symptoms of the associated disease, pathological condition, disorder, or event; preventative treatment, that is, treatment directed to minimizing or partially or completely inhibiting the development of the associated disease, pathological condition, disorder, or event, e.g., in a patient who is not yet ill, but who is susceptible to, or otherwise at risk of, a particular disease, pathological condition, disorder, or event; and supportive treatment, that is, treatment employed to supplement another specific therapy directed toward the improvement of the associated disease, pathological condition, disorder, or event.

As used herein, "walking ability" refers to the ability of a patient (e.g., a patient having a muscle weakness disease described herein) to lift and set down each foot in turn. Walking ability may be assessed by tests, in particular, the Six-Minute Walk Test (6 MWT). See the American Thoracic Society statement: guidelines for the six-minute walk test (*American Journal of Respiratory and Critical Care Medicine,* 166(1):111-7, 2002), hereby incorporated by reference in its entirety.

Other features and advantages of the present disclosure will be apparent from the following Detailed Description, the drawings, and the claims.

BRIEF DESCRIPTION OF THE DRAWINGS

FIGS. 2A-2D are graphs of fiber size distribution in the soleus muscles dissected from wild type (WT) mice or Akp2$^{-/-}$ mice. The percentages of fibers of different minimum sizes (μm$^2$) are shown for all fibers (FIG. 2A), type I fibers (FIG. 2B), type IIa fibers (FIG. 2C), or type IIb fibers (FIG. 2D).

FIGS. 3A-3D are graphs of contractile properties of the soleus muscles from wild type (WT) mice or Akp2$^{-/-}$ mice. Muscle mass (FIG. 3A), strength (FIG. 3B), force frequency (FIG. 3C), and fatigue characteristics (FIG. 3D) were compared in both male and female mice.

FIGS. 4A-4D are graphs of contractile properties of the extensor digitorum longus (EDL) muscles from wild type (WT) mice or Akp2$^{-/-}$ mice. Muscle mass (FIG. 4A), strength (FIG. 4B), force frequency (FIG. 4C), and fatigue characteristics (FIG. 4D) were compared in both male and female mice.

DETAILED DESCRIPTION

Figure 1:
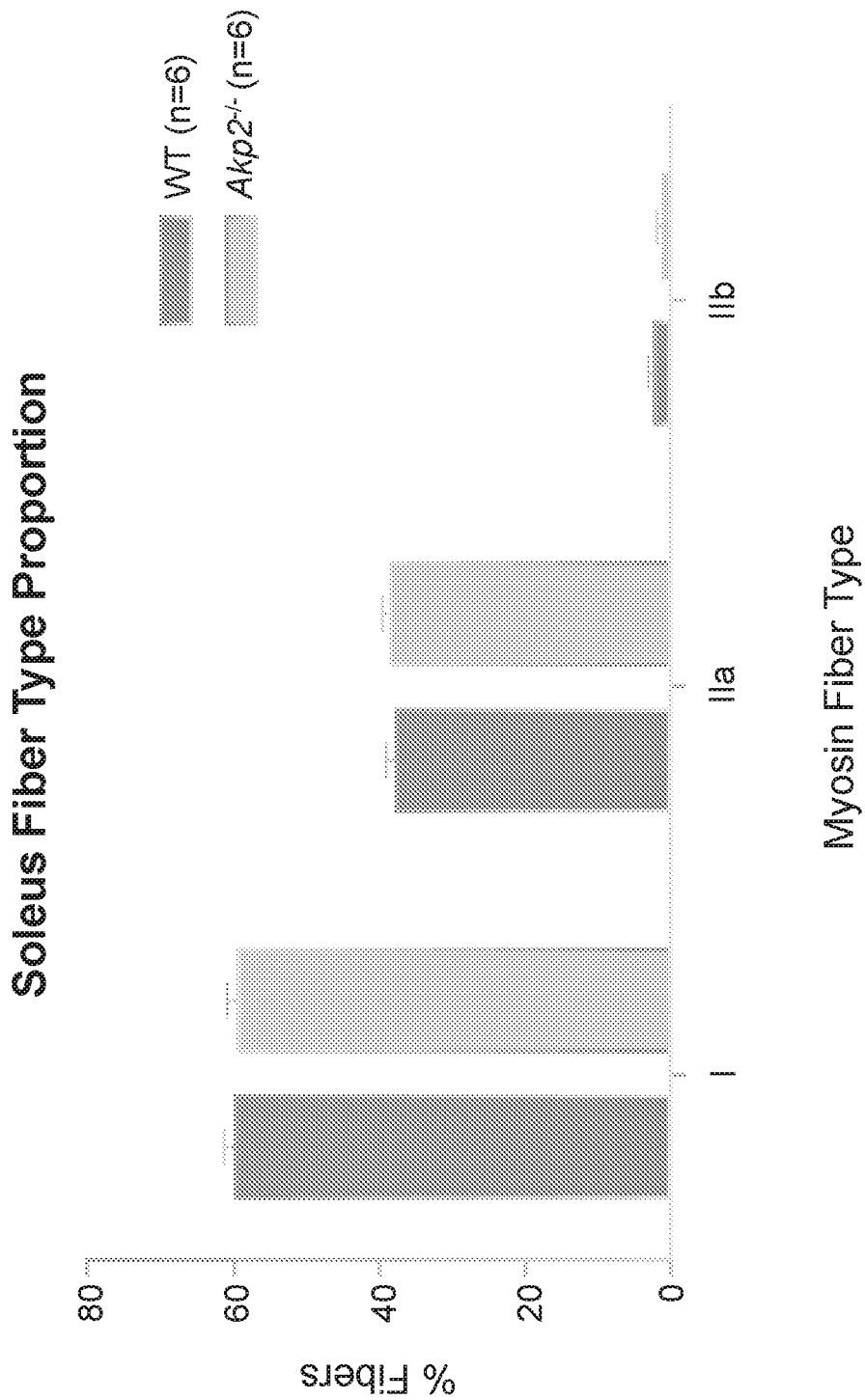
FIG. 1 is a graph showing the percentage of myosin fiber type in all soleus muscle fibers from wild type (WT) mice or Akp2$^{-/-}$ mice.

Muscle weakness has been reported as one of the several symptoms of HPP (Seshia et al. 1990 *Archives of Disease in Childhood* 65:130-131). In addition to HPP, other diseases or disorders may also lead to muscle weakness. For example, magnesium shortage results in muscle weakness in calcium pyrophosphate deposition disease (CPPD, or CPDD) patients (Hahn et al. 2012 *BMC Gastroenterology* 12-19). Some muscle weakness diseases or disorders, such as HPP, CPPD, familial hypophosphatemia (such as autosomal dominant hypophosphatemic rickets (ADHR), autosomal recessive hypophosphatemic rickets, X-linked hypophosphatemic rickets, X-linked hypophosphatemia (XLH), etc.), share a characteristic feature of elevated pyrophosphate (PPi) concentration in the subject suffering the diseases or disorders. In HPP, the elevated PPi concentration is due to the loss of function mutation(s) in the gene ALPL that encodes the tissue nonspecific isozyme of alkaline phosphatase (TNALP; a.k.a. liver/bone/kidney type ALP), which is an enzyme for substrates such as PPi, phosphoethanolamine (PEA) and pyridoxal 5'-phosphate (PLP). In CPPD, a deficiency of Mg, which acts as a cofactor for various phosphatases, leads to higher amounts of PPi, which is a necessary precursor for the formation of CPPD crystals. The deposition of calcium pyrophosphate may further lead to chronic inflammatory arthritis, hypophosphatasia, hypomagnesemia, and hyperparathyroidism with chondrocalcinosis and acute attacks of "pseudogout."

The instant disclosure teaches methods of treating a muscle weakness disease in a subject characterized as having one or more of the following: an elevated PPi concentration, decreased alkaline phosphatase concentration, an average BOT-2 strength score of, e.g., less than 10, an average BOT-2 running speed and agility score of, e.g., less than 5, an average CHAQ index score of, e.g., greater than about 0.8, or an average PODCI score of, e.g., less than about 40, an average 6 MWT of, e.g., less than about 80% of the predicted 6 MWT value (e.g., in which the predicted 6 MWT value is the 6 MWT value of an age-matched and/or gender-matched normal subject), a Muscle Strength Grade of, e.g., less than 5, and/or an average HHD value (e.g., an average HHD muscle or grip strength value) of, e.g., less than about 50% of the predicted HHD value (e.g., in which the predicted HHD value is the HHD value of an age-matched and/or gender-matched normal subject). In particular, the subject has been identified as having or being prone to a muscle weakness.

For example, disclosed are methods of identifying subjects (e.g., humans) having or being prone to a muscle weakness disease for treatment with a recombinant polypeptide having alkaline phosphatase activity (such as TNALP, for example the sALP polypeptide of SEQ ID NO: 1 or a polypeptide variant having at least 95% sequence identity to the sequence of SEQ ID NO: 1, e.g., asfotase alfa) characterized as having an elevated PPi concentration, decreased ALP concentration, an average BOT-2 strength score of, e.g., less than 10, an average BOT-2 running speed and agility score of, e.g., less than 5, an average CHAQ index score of, e.g., greater than about 0.8, an average PODCI score of, e.g., less than about 40, an average 6 MWT of, e.g., less than about 80% of the predicted 6 MWT value, a Muscle Strength Grade of, e.g., less than 5, and/or an average HHD value (e.g., an average HHD muscle or grip strength value) of, e.g., less than about 80% of the predicted HHD value. For example, an elevated concentration of PPi in a sample (e.g., a plasma sample) from an infant or child (e.g., a subject less than about 12 years of age) may be about 5.71 μM or greater, an elevated concentration of PPi in a sample (e.g., a plasma sample) from an adolescent (e.g., a subject of about 13 to about 18 years of age) may be about 4.78 μM or greater; and an elevated concentration of PPi in a sample (e.g., a plasma sample) from an adult (e.g., a subject of greater than about 18 years of age) may be about 5.82 μM or greater. In particular, a decreased ALP concentration in a sample (e.g., a plasma sample) from the subject may be, e.g., about 90 U/L or less for a subject of 0 to 14 days of age; about 134 U/L or less for a subject of 15 days of age to less than 1 year of age; about 156 U/L or less for a subject of about 1 year of age to less than 10 years of age; about 141 U/L or less for a subject of about 10 years of age to less than about 13 years of age; about 62 U/L or less for a female subject of about 13 years of age to less than about 15 years of age; about 127 U/L or less for a male subject of about 13 years of age to less than about 15 years of age; about 54 U/L or less for a female subject of about 15 years of age to less than about 17 years of age; about 89 U/L or less for a male subject of about 15 years of age to less than about 17 years of age; about 48 U/L or less for a female subject of about 17 years of age or older; or about 59 U/L or less for a male subject of about 17 years of age or older.

The instant disclosure provides a method of treating or ameliorating a muscle weakness in a subject having or being prone to a muscle weakness disease, comprising administering to said subject a therapeutically effective amount of at least one recombinant polypeptide having alkaline phosphatase activity. In particular, the subject has been identified as having or being prone to a muscle weakness.

The instant disclosure also provides a method of identifying a subpopulation of subjects having or being prone to a muscle weakness disease, wherein the subjects in said subpopulation have elevated PPi concentrations, decreased alkaline phosphatase concentrations, and/or decreased grip or muscle strength (e.g., as assessed using the BOT-2, 6 MWT, CHAQ, PODCI, Muscle Strength Grade, and/or HHD).

Methods for: 1) identifying a subpopulation of subjects having or being prone to a muscle weakness disease, wherein the subjects in said subpopulation have elevated PPi concentrations, decreased ALP concentrations, and/or decreased grip or muscle strength; and 2) then treating or ameliorating at least one symptom of the muscle weakness disease in a subject in said subpopulation are also described.

Methods of identifying a subpopulation of subjects having or being prone to a muscle weakness disease characterized with elevated PPi concentrations, decreased ALP concentrations, and/or decreased grip or muscle strength are also described.

The subpopulation of subjects can be identified irrespective of whether they have previously been diagnosed with hypophosphatasia (HPP), calcium pyrophosphate deposition disease (CPPD), or familial hypophosphatemia (such as autosomal dominant hypophosphatemic rickets (ADHR), autosomal recessive hypophosphatemic rickets, X-linked hypophosphatemic rickets, X-linked hypophosphatemia (XLH), etc.). The subpopulation is identified, for example, based on an elevated PPi concentration in such subjects. Causes of elevated PPi concentration include, for example, defects in signaling molecules, or mutations in genes that encode such signaling molecules, which regulate the production, degradation, or other ways influencing the stability of PPi. For example, the defects or mutations to signaling molecules may result in overexpression of PPi or decreased degradation or hydrolysis of PPi. HPP patients have defective or missing tissue nonspecific alkaline phosphatase, which can hydrolyze PPi. Thus, similar to HPP, in other diseases due to defects in alkaline phosphatases, PPi concentration may be elevated. The defects in signaling molecules also include defects in the co-factors or other molecules facilitating the function of the signaling molecules. For example, in CPPD, a deficiency of Mg, which acts as a cofactor for various phosphatases, leads to elevated levels of PPi.

Described herein are methods for identifying a subpopulation of subjects who either exhibit a muscle weakness disease-related symptom, or who are at risk for developing such muscle weakness disease-related symptoms. The identified population can include subjects who have previously been identified as having such muscle weakness disease or who are asymptomatic without a previous diagnosis. The muscle weakness diseases in the present disclosure include, for example, HPP or HPP-related diseases, CPPD or CPPD-related diseases, familial hypophosphatemia (such as autosomal dominant hypophosphatemic rickets (ADHR), autosomal recessive hypophosphatemic rickets, X-linked hypophosphatemic rickets, X-linked hypophosphatemia (XLH), etc.), or any other muscle weakness diseases with elevated PPi. Methods for identifying the subject subpopulation include, for example, the detection of elevated inorganic pyrophosphate (PPi) concentration in such subject.

Targeted Muscle Weakness Diseases

Provided herein are methods for treating or ameliorating at least one symptom of a subject having or being prone to a muscle weakness disease. The muscle weakness disease, myopathy, or myasthenia, described herein may include any disease or disorder which causes, is due to, or is related to at least one symptom of muscle weakness. The term "muscle weakness, "myopathy," "myasthenia" or other similar expressions in this disclosure refers to a condition related to impaired status of muscle function, such as a lack or defect of muscle strength, compared to other subjects having not such condition or to the same subject at the time point prior to having such condition. Muscle weakness can be divided into conditions that have either true or perceived muscle weakness. True muscle weakness may include a condition where the force exerted by the muscles is less than would be expected. For example, true muscle weakness includes a variety of skeletal muscle diseases, including muscular dystrophy and inflammatory myopathy. Exemplary disease or disorder includes neuromuscular junction disorders, such as myasthenia gravis. Muscle weakness can also be caused by low levels of potassium and other electrolytes within muscle cells, where the force exerted by the muscles is less than would be expected. Perceived muscle weakness (or non-neuromuscular weakness) describes a condition where a subject feels more effort than normal (i.e., compared to other subjects having not such condition or to the same subject at the time point prior to having such condition) is required to exert a certain amount of force but actual muscle strength is normal, for example chronic fatigue syndrome.

In some conditions, such as myasthenia gravis, muscle strength is normal when resting, but true weakness occurs after the muscle has been subjected to exercise. This is also true for some cases of chronic fatigue syndrome, where objective post-exertion muscle weakness with delayed recovery time has been measured and is a feature of some of the published definitions. These diseases or disorders are also included in the "muscle weakness disease" of this disclosure.

Muscle weakness can also be classified as either "proximal" or "distal" based on the location of the muscles that it affects. Proximal muscle weakness affects muscles closest to the body's midline, while distal muscle weakness affects muscles further out on the limbs. Proximal muscle weakness can be seen in Cushing's Syndrome and Hyperthyroidism.

Other categories of muscle weakness exist in practice. For example, neuromuscular fatigue can be classified as either "central" or "peripheral" depending on its cause. Central muscle fatigue manifests as an overall sense of energy deprivation, while peripheral muscle fatigue manifests as a local, muscle-specific inability to do work The severity of muscle weakness can be classified into different "grades" based on the following exemplary criteria:
Grade 0: No contraction or muscle movement.
Grade 1: Trace of contraction, but no movement at the joint.
Grade 2: Movement at the joint with gravity eliminated.
Grade 3: Movement against gravity, but not against added resistance.
Grade 4: Movement against external resistance with less strength than usual.
Grade 5: Normal strength.

Hypophosphatasia (HPP) and Muscle Weakness

Hypophosphatasia (HPP) is the rare inherited metabolic disorder resulting from loss-of-function mutation(s) in the tissue-nonspecific alkaline phosphatase (TNSALP) gene. The biochemical hallmark is subnormal ALP activity in serum (hypophosphatasemia), which leads to elevated blood and/or urine levels of three phosphocompound substrates: inorganic pyrophosphate (PPi), phosphoethanolamine (PEA) and pyridoxal 5'-phosphate (PLP). TNSALP deficiency can cause a spectrum of sequelae including premature loss of primary teeth, rickets, poor growth, muscle weakness, compromised physical function, and pain. Muscle weakness, or myopathy, has been found in association with HPP decades ago. For example, Seshia et al. (1990) reported that three children with HPP also had muscle pains, stiffness, and symptoms of proximal lower limb muscle weakness that occurred early in the disorder (remaining presenting in two of them). Interestingly, Seshia et al. (1990) found that those symptoms "could not be explained by skeletal impairment," but rather "resembled those in osteomalacia myopathy." Other signs and symptoms with HPP may include: long-term pain in the muscles or joints, arthritis (in adults and children), pseudogout caused by deposits of calcium in the joints, inability to walk without an assistive device such as crutches, a walker, or a wheelchair, etc. Recently, asfotase alfa, a recombinant bone-targeted human TNASLP (i.e., sALP-Fc-$D_{10}$), has been reported to decrease the elevated inorganic pyrophosphate (PPi) concentration and improved skeletal mineralization, growth, and physical function of HPP patients. Children of 5-12-year old with HPP being treated with asfotase alfa for more than three years showed improvements in muscle strength, measured by Hand Held Dynamometry (HHD) and individual subtests of the Bruininks-Oseretsky Test of Motor Proficiency, $2^{nd}$ Edition (BOT-2) including Strength and Running Speed/Agility scaled scores. As a result, they had significant gains in physical function of their muscles which impact ability to perform activities of daily living.

Asfotase alfa can be administered to treat, e.g., perinatal HPP, infantile HPP, childhood HPP, and odonto-HPP. For example, patients having childhood HPP (e.g., children of about 5 to about 12 years of age having HPP) or infantile HPP (e.g., infants of about 3 years of age or less than 3 years of age) can be treated with a sALP (such as TNALP, for example the sALP polypeptide of SEQ ID NO: 1 or a polypeptide variant having at least 95% sequence identity to the sequence of SEQ ID NO: 1, e.g., asfotase alfa) for a period of at least one year (e.g., at least five years, at least six years, at least seven years, at least eight years, at least nine years, at least ten years, or more than ten years (e.g., the lifetime of the patient)).

Since the asfotase alfa treatment dramatically improves bone mineralization in patients, it was uncertain whether its effects on patients' muscle strength were merely a result of the restored bone formation and the following restoration of skeletal muscle attachment/growth or a therapeutic effect directly to patients' muscles. As described herein, we have discovered that asfotase alfa has a therapeutic effect on the muscles of a patient (e.g., a patient having a muscle weakness disease, such as muscle weakness in a patient having HPP).

Calcium Pyrophosphate Deposition Disease (CPPD, or CPDD) and Muscle Weakness

Calcium pyrophosphate deposition disease (CPPD, or CPDD), or calcium pyrophosphate dihydrate crystal deposition disease, is a metabolic arthropathy caused by the deposition of calcium pyrophosphate dihydrate crystals in and around joints, especially in articular cartilage and fibrocartilage. Although CPPD is often asymptomatic, with only radiographic changes seen (i.e., chondrocalcinosis), various clinical manifestations may occur, including acute (pseudogout) and chronic arthritis. The crystal deposits provoke inflammation in the joint, which can cause the joint cartilage to break down. The disease may take a few different arthritis-related forms: osteoarthritis, a chronic rheumatoid arthritis (RA)-like inflammatory arthritis, or an acutely painful inflammatory condition called pseudogout. The name pseudogout comes from the fact that it resembles another acutely painful condition called gout. The main difference is the type of crystals involved in the inflammation and damage. Almost any joint may be involved by CPPD, although the knees, wrists, and hips are most often affected. This condition is the most common cause of secondary metabolic osteoarthritis. Patients with CPPD can experience significant morbidity due to the pain of an acute attack of pseudogout or to symptoms of chronic arthropathy. Treatment of symptomatic CPPD is important to prevent further end-organ damage, but it cannot reverse the joint disease.

The exact mechanism for the development of CPPD remains unclear. From aging, genetic factors, or both, patients have increased adenosine triphosphate breakdown resulting in increased inorganic pyrophosphate concentration in the joints. Changes in the cartilage matrix may play an important role in promoting calcium pyrophosphate dihydrate crystal deposition. Over activity of enzymes that break down triphosphates, such as nucleoside triphosphate pyrophosphohydrolase, has been observed in the cartilage of patients with CPPD. Therefore, inorganic pyrophosphate can bind calcium, leading to deposition in the cartilage and synovium. (see Beutler et al., 1993 *Arthritis Rheum.* 36(5): 704-715). Hyaline cartilage is affected most commonly, but fibrocartilage, such as the meniscal cartilage of the knee, can also be involved. (Pritzker et al., 1988 *J Rheumatol.* 15(5): 828-835).

Other Diseases and Muscle Weakness

Similarly to HPP and CPPD (or CPDD), other diseases or disorders may include at least one symptom of muscle weakness. Among them, some types of muscle weakness diseases have characteristic elevated inorganic pyrophosphate (PPi) concentration. These muscle weakness diseases with elevated PPi concentration are also targets for treatment with asfotase alfa in the instant disclosure.

For example, familial hypophosphatemia (such as autosomal dominant hypophosphatemic rickets (ADHR), autosomal recessive hypophosphatemic rickets, X-linked hypophosphatemic rickets, X-linked hypophosphatemia (XLH), etc.) typically has a muscle weakness phenotype. Hypophosphatemia, or hypophosphatemic rickets, is a form of rickets that is characterized by low serum phosphate levels and resistance to treatment with ultraviolet radiation or vitamin D ingestion. X-linked hypophosphatemia (XLH) is a dominant disorder and accounts for more than 80% of all familial hypophosphatemia. XLH is considered to be a systemic disorder, from mutation of the phosphate-regulating gene homologous to endopeptidases on the X chromosome (PHEX). XLH patients demonstrate a normal or low serum concentration of 1,25-dihydroxyvitamin D3, suggestive of inadequate formation of this vitamin D metabolite. The remaining 20% of familial hypophosphatemia patients have autosomal dominant hypophosphatemic rickets from gain-of-function autosomal recessive hypophosphatemic rickets and hereditary hypophosphatemic rickets with hypercalciuria.

Methods of Treatment

Provided herein are methods for treating or ameliorating at least one symptom of a subject, child, adolescent, or adult, who has or is prone to a muscle weakness disease. Such treatment may include administering an alkaline phosphatase, or a polypeptide having alkaline phosphatase activity, to decrease the elevated PPi concentration in such subject. For example, a soluble alkaline phosphatase (sALP, such as TNALP, for example the sALP polypeptide of SEQ ID NO: 1 or a polypeptide variant having at least 95% sequence identity to the sequence of SEQ ID NO: 1, e.g., asfotase alfa) may be administered across a range of ages for children, adolescent, or adult subjects.

Subjects can be diagnosed with a muscle weakness disease (such as HPP, CPPD, familial hypophosphatemia described herein, etc.) prior to administration of an alkaline phosphatase, or a polypeptide having alkaline phosphatase activity, (e.g., a sALP, such as TNALP, for example the sALP polypeptide of SEQ ID NO: 1 or a polypeptide variant having at least 95% sequence identity to the sequence of SEQ ID NO: 1, e.g., asfotase alfa). Additionally, a subject having or being prone to a muscle weakness disease can be a naïve subject that has not have previously received treatment with a sALP (such as TNALP, for example the sALP polypeptide of SEQ ID NO: 1 or a polypeptide variant having at least 95% sequence identity to the sequence of SEQ ID NO: 1, e.g., asfotase alfa).

The method involves administering an alkaline phosphatase, or a polypeptide having alkaline phosphatase activity, (e.g., a sALP, such as TNALP, for example the sALP polypeptide of SEQ ID NO: 1 or a polypeptide variant having at least 95% sequence identity to the sequence of SEQ ID NO: 1, e.g., asfotase alfa) to a subject having or being prone to a muscle weakness disease in a single or multiple dosages over a period of time. In particular, a sALP, such as asfotase alfa, can be administered to a subject previously determined to have elevated inorganic pyrophosphate (PPi) concentration or have at least one predetermined biomarker/score for muscle weakness, such as an average BOT-2 strength score of less than 10, an average BOT-2 running speed and agility score of less than 5, an average CHAQ index score greater than about 0.8, and/or an average PODCI score of less than about 40, an average 6 MWT of less than about 80% of the predicted 6 MWT value, a Muscle Strength Grade of less than 5, and/or an average HHD value (e.g., an average HHD muscle or grip strength value) of, e.g., less than about 80% of the predicted HHD value. For example, a sALP can be administered to a subject previously determined to have a concentration of PPi in a sample (e.g., a plasma sample) of greater than about 5.71 μM for an infant or child (e.g., a subject less than about 12 years of age); greater than about 4.78 μM for an adolescent (e.g., a subject of about 13 to about 18 years of age); or greater than about 5.82 μM for an adult (e.g., a subject of greater than about 18 years of age). In other embodiments, the muscle weakness disease described herein is caused by an elevated concentration of at least one alkaline phosphatase substrate (e.g., PPi, PLP, PEA, etc.). Alternatively, an alkaline phosphatase, or a polypeptide having alkaline phosphatase activity, (e.g. a sALP, such as TNALP, for example the sALP polypeptide of SEQ ID NO: 1 or a polypeptide variant having at least 95% sequence identity to the sequence of SEQ ID NO: 1, e.g., asfotase alfa) can be administered to a subject having or being prone to a muscle weakness disease prior to determination of such scores (e.g., the BOT-2 strength score, BOT-2 running speed and agility score, the CHAQ index score, the BSID-III scaled score, the PDMS-2 standard score, a Muscle Strength score, a 6 MWT value, and/or a HHD value) to allow for, e.g., an increase in activities of ADL, a decrease in pain, and/or improved motor development.

Additionally, each of the described scores (e.g., the BOT-2 strength score, BOT-2 running speed and agility score, the CHAQ index score, the BSID-III scaled score, the PDMS-2 standard score, 6 MWT, the 12-POMA-G, a modified performance-oriented mobility assessment (mPOMA-G, such as the one illustrated in Phillips et al. 2015 Bone Abstracts 4:P136), or the HHD value) of a subject having or being prone to a muscle weakness disease described herein can be used singly or in any combination to assess treatment efficacy using a sALP (such as TNALP, for example the sALP polypeptide of SEQ ID NO: 1 or a polypeptide variant having at least 95% sequence identity to the sequence of SEQ ID NO: 1, e.g., asfotase alfa), in which improvements relative to a certain test score demonstrate that the sALP is effective for treating such muscle weakness disease.

For example, when administration of an alkaline phosphatase or a polypeptide having alkaline phosphatase activity (e.g., a sALP, such as TNALP, for example the sALP polypeptide of SEQ ID NO: 1 or a polypeptide variant having at least 95% sequence identity to the sequence of SEQ ID NO: 1, e.g., asfotase alfa) to a subject having or being prone to a muscle weakness disease results in an average increase in the BOT-2 strength score to about 10 or greater than about 10, in which the subject previously had an average BOT-2 strength score of less than about 10, then the alkaline phosphatase or a polypeptide having alkaline phosphatase activity treatment is effective at treating, e.g., physical impairments associated with a muscle weakness disease. Alternatively, when administration of a sALP does not result in an average increase in the BOT-2 strength score to about 10 or greater than about 10, the dosage and/or frequency of alkaline phosphatase or a polypeptide having alkaline phosphatase activity administration can be changed in order to determine the effective amount of the alkaline phosphatase or a polypeptide having alkaline phosphatase activity for the subject. For instance, the dosage of the sALP (such as TNALP, for example the sALP polypeptide of SEQ ID NO: 1 or a polypeptide variant having at least 95% sequence identity to the sequence of SEQ ID NO: 1, e.g., asfotase alfa) can be increased from, e.g., about 3 mg/kg/week to about 6 mg/kg/week or about 6 mg/kg/week to about 9 mg/kg/wk.

Additionally, when administration of an alkaline phosphatase or a polypeptide having alkaline phosphatase activity (e.g., a sALP, such as TNALP, for example the sALP polypeptide of SEQ ID NO: 1 or a polypeptide variant having at least 95% sequence identity to the sequence of SEQ ID NO: 1, e.g., asfotase alfa) to a subject having or being prone to a muscle weakness disease results in an improvement in the Muscle Strength Grade categorization of the subject of one or more (e.g., an improvement to a Muscle Strength Grade of 1, 2, 3, 4, or 5 from a prior, lower Muscle Strength Grade), in which the subject previously had an average Muscle Strength Grade of less than about 5, then the alkaline phosphatase or a polypeptide having alkaline phosphatase activity treatment is effective at treating, e.g., physical impairments associated with a muscle weakness disease. Alternatively, when administration of a sALP does not result in an improvement in the Muscle Strength Grade categorization of the subject of one or more from a prior, lower Muscle Strength Grade, the dosage and/or frequency of alkaline phosphatase or a polypeptide having alkaline phosphatase activity administration can be changed (e.g., increased) in order to determine the effective amount of the alkaline phosphatase or a polypeptide having alkaline phosphatase activity for the subject. For instance, the dosage of the sALP (such as TNALP, for example the sALP polypeptide of SEQ ID NO: 1 or a polypeptide variant having at least 95% sequence identity to the sequence of SEQ ID NO: 1, e.g., asfotase alfa) can be increased from, e.g., about 3 mg/kg/week to about 6 mg/kg/week or about 6 mg/kg/week to about 9 mg/kg/wk.

Biomarkers/Endpoints for Diagnosis and/or Treatment of Muscle Weakness Diseases

In preferred embodiments, a muscle weakness disease (such as HPP including, e.g., perinatal HPP, infantile HPP, childhood HPP, and odontohypophosphatasia, CPPD, and familial hypophosphatemia as described herein) is treated with an alkaline phosphatase, or a polypeptide having alkaline phosphatase activity, (e.g. a sALP, such as TNALP, for example the sALP polypeptide of SEQ ID NO: 1 or a polypeptide variant having at least 95% sequence identity to the sequence of SEQ ID NO: 1, e.g., asfotase alfa). The methods described herein are also useful for diagnosing a subject having or being prone to a muscle weakness disease, identifying a subject as a member in a specific subpopulation of subjects having or being prone to a muscle weakness disease, or testing the efficacy of treatment of a muscle weakness disease. For example, a subject may be diagnosed as having or being prone to a muscle weakness disease if such subject shows certain characteristic biomarkers. A subject may be treated with an alkaline phosphatase, or a polypeptide having alkaline phosphatase activity, (e.g. a sALP, such as TNALP, for example the sALP polypeptide of SEQ ID NO: 1 or a polypeptide variant having at least 95% sequence identity to the sequence of SEQ ID NO: 1, e.g., asfotase alfa), while the treatment efficacy or effects may be analyzed using certain characteristic biomarkers or endpoints. Such biomarkers may include, e.g., the elevated inorganic pyrophosphate (PPi) concentration and/or the decreased alkaline phosphatase (ALP) in the serum, the bone or muscle tissues, or the urine of the subject. Exemplary endpoints useful in the methods described herein for muscle weakness treatment may include: (1) the Bruininks-Oseretsky Test of Motor Proficiency $2^{nd}$ Edition (BOT-2), (2) the Childhood Health Assessment Questionnaire (CHAQ), (3) the Pediatric Outcomes Data Collection Instrument (PODCI), (4) Bayley Scales of Infant and Toddler Development, $3^{rd}$ Edition (BSID-III), (5) the Peabody Developmental Motor Scales, 2nd Edition (PDMS-2), (6) the Six Minute Walk Test (6 MWT), (7) the Muscle Strength Grade, and (8) Handheld Dynamometry (HHD), which are described in further detail below.

Plasma Inorganic Pyrophosphate (PPi) and Alkaline Phosphatase (ALP) Concentrations Subjects having or being prone to a muscle weakness disease can be identified for treatment with an alkaline phosphatase or a polypeptide having alkaline phosphatase activity, (e.g. a sALP, such as TNALP, for example the sALP polypeptide of SEQ ID NO: 1 or a polypeptide variant having at least 95% sequence identity to the sequence of SEQ ID NO: 1, e.g., asfotase alfa) by determining the inorganic pyrophosphate (PPi) and/or alkaline phosphatase (ALP) concentrations in a sample, such as a plasma or urine sample, from the patient. Any method known to those of skill in the art can be used to quantify the PPi and/or ALP concentrations in a plasma sample or alternatively in a urine sample, as described in detail in Whyte et al., 1995 (J. Clin. Invest. 95(4): 1440-1445), hereby incorporated by reference in its entirety. Methods to quantify PPi concentrations in a plasma or urine sample are also described in Cheung et al., 1977 (Anal. Biochem. 83: 61-63), Cook et al., 1978 (Anal. Biochem. 91: 557-565), and Johnson et al, 1968 (Anal. Biochem. 26: 137-145), which are each hereby incorporated by reference in their entirety.

In particular, an alkaline phosphatase or a polypeptide having alkaline phosphatase activity (e.g. a sALP, such as TNALP, for example the sALP polypeptide of SEQ ID NO: 1 or a polypeptide variant having at least 95% sequence identity to the sequence of SEQ ID NO: 1, e.g., asfotase alfa) can be administered to a subject (e.g., a human) having or being prone to a muscle weakness disease previously determined to have a plasma PPi concentration of up to about 6 µM (e.g., about 4.5 µM, about 5 µM, or about 5.5 µM or a plasma PPi concentration within the range of about 4.5 µM to about 6 µM). For example, the alkaline phosphatase or the polypeptide having alkaline phosphatase activity is administered to, e.g., an infant or child (e.g., a subject less than about 12 years of age) having a plasma PPi concentration of about 5.71 µM or greater; an adolescent (e.g., a subject of about 13 to about 18 years of age) having a plasma PPi concentration of about 4.78 µM or greater; or an adult (e.g., a subject of greater than about 18 years of age) having a plasma PPi concentration of about 5.82 µM or greater. Additionally, an alkaline phosphatase or a polypeptide having alkaline phosphatase activity can be administered to a subject (e.g., a human) having or being prone to a muscle weakness disease previously determined to have a plasma ALP concentration of, e.g., about 90 U/L or less for a subject of 0 to 14 days of age; about 134 U/L or less for a subject of 15 days of age to less than 1 year of age; about 156 U/L or less for a subject of about 1 year of age to less than 10 years of age; about 141 U/L or less for a subject of about 10 years of age to less than about 13 years of age; about 62 U/L or less for a female subject of about 13 years of age to less than about 15 years of age; about 127 U/L or less for a male subject of about 13 years of age to less than about 15 years of age; about 54 U/L or less for a female subject of about 15 years of age to less than about 17 years of age; about 89 U/L or less for a male subject of about 15 years of age to less than about 17 years of age: about 48 U/L or less for a female subject of about 17 years of age or older; or about 59 U/L or less for a male subject of about 17 years of age or older.

The plasma PPi concentration and/or plasma ALP concentration of a subject (e.g., a human) having or being prone to a muscle weakness disease can be compared to the plasma PPi concentration and/or plasma ALP of a normal subject to determine a treatment effect in the subject administered an alkaline phosphatase or a polypeptide having alkaline phosphatase activity (e.g. a sALP, such as TNALP, for example the sALP polypeptide of SEQ ID NO: 1 or a polypeptide variant having at least 95% sequence identity to the sequence of SEQ ID NO: 1, e.g., asfotase alfa). In particular, the alkaline phosphatase or the polypeptide having alkaline phosphatase activity can be administered for a treatment period of least one year (e.g., at least two years, at least three years, at least four years, at least five years, at least six years, at least seven years, at least eight years, at least nine years, at least ten years, or longer than ten years, such as for the lifetime of the patient). Alternatively, the methods can include determining the plasma PPi concentration and/or plasma ALP concentration prior to administering the alkaline phosphatase or the polypeptide having alkaline phosphatase activity to assess an effect in the subject of treatment with the alkaline phosphatase or the polypeptide having alkaline phosphatase activity.

The methods result in a decrease in PPi and/or an increase in ALP concentration in a sample (e.g., a plasma sample) from a subject (e.g., a human) having or being prone to a muscle weakness disease. For example, treatment with an alkaline phosphatase or a polypeptide having alkaline phosphatase activity (e.g. a sALP, such as TNALP, for example the sALP polypeptide of SEQ ID NO: 1 or a polypeptide variant having at least 95% sequence identity to the sequence of SEQ ID NO: 1, e.g., asfotase alfa) results in a decrease in PPi concentration in a sample (e.g., a plasma sample) from the patient of about 1 μM, about 1.5 μM, about 2 μM, about 2.5 μM, or about 3 μM or 25% or greater (e.g., 30%, 35%, 40%, 45%, 50%, 55%, 60%, or more than 60%). Thus, the subject exhibits a plasma PPi concentration of, e.g., about 2 μM to about 5 μM, about 3 μM to about 5 μM, about 2 μM to about 4 μM, or about 2 μM to about 3 μM after administration of the alkaline phosphatase or the polypeptide having alkaline phosphatase activity.

Likewise, treatment with alkaline phosphatase or a polypeptide having alkaline phosphatase activity results in an increase in ALP concentration in a sample (e.g., a plasma sample) from a subject (e.g., a human) having or being prone to a muscle weakness disease of 30%, 35%, 40%, 45%, 50%, 55%, 60%, or more than 60%, relative to the subject prior to administration of the alkaline phosphatase or a polypeptide having alkaline phosphatase activity. For example, administration of the alkaline phosphatase or the polypeptide having alkaline phosphatase activity increases the ALP concentration in a sample (e.g., a plasma sample) from the subject to, e.g., about 273 U/L or greater for a subject of 0 to 14 days of age; about 518 U/L or greater for a subject of 15 days of age to less than 1 year of age; about 369 U/L or greater for a of about 1 year of age to less than 10 years of age; about 460 U/L or greater for a subject of about 10 years of age to less than about 13 years of age; about 280 U/L or greater for a female subject of about 13 years of age to less than about 15 years of age; about 517 U/L or greater for a male subject of about 13 years of age to less than about 15 years of age; about 128 U/L or greater for a female subject of about 15 years of age to less than about 17 years of age; about 365 U/L or greater for a male subject of about 15 years of age to less than about 17 years of age; about 95 U/L or greater for a female subject of about 17 years of age or older; or about 164 U/L or greater for a male subject of about 17 years of age or older.

The decrease in the plasma PPi and/or increase in the ALP concentrations of the subject (e.g., a human) having or being prone to a muscle weakness disease can be sustained throughout administration of the alkaline phosphatase or the polypeptide having alkaline phosphatase activity (e.g. a sALP, such as TNALP, for example the sALP polypeptide of SEQ ID NO: 1 or a polypeptide variant having at least 95% sequence identity to the sequence of SEQ ID NO: 1, e.g., asfotase alfa). For instance, the plasma PPi concentration decreases by about 25% and remains at ±10% of the decreased plasma PPi concentration during treatment with the sALP and/or the plasma ALP concentration increases by about 50% and remains at ±10% of the increased plasma ALP concentration during treatment with the alkaline phosphatase or the polypeptide having alkaline phosphatase activity.

Alternatively, when administration of an alkaline phosphatase or a polypeptide having alkaline phosphatase activity (e.g. a sALP, such as TNALP, for example the sALP polypeptide of SEQ ID NO: 1 or a polypeptide variant having at least 95% sequence identity to the sequence of SEQ ID NO: 1, e.g., asfotase alfa) does not result in an average decrease in PPi concentrations in a plasma sample from the subject (e.g., a human) having or being prone to a muscle weakness disease by about 25% or greater, the dosage and/or frequency of sALP administration can be changed in order to determine the effective amount of the sALP for the subject. Likewise, when administration of an alkaline phosphatase or a polypeptide having alkaline phosphatase activity does not result in an average increase in ALP concentrations in a plasma sample from the subject by about 50% or greater, the dosage and/or frequency of alkaline phosphatase or a polypeptide having alkaline phosphatase activity administration can be changed in order to determine the effective amount of the an alkaline phosphatase or a polypeptide having alkaline phosphatase activity for the subject. For instance, the dosage of the an alkaline phosphatase or a polypeptide having alkaline phosphatase activity can be increased from, e.g., about 2.1 mg/kg/week or about 3.5 mg/kg/week to about 6 mg/kg/week or about 9 mg/kg/week.

Bruininks-Oseretsky Test of Motor Proficiency $2^{nd}$ Edition (BOT-2)

An exemplary Bruininks-Oseretsky Test of Motor Proficiency $2^{nd}$ Edition (BOT-2) is described in Bruininks, R. H. (2005). *Bruininks-Oseretsky Test of Motor Proficiency*, (BOT-2), Minneapolis, Minn.: Pearson Assessment, hereby incorporated by reference in its entirety. In particular, the BOT-2 can be used to evaluate physical impairments and mobility restrictions in a subject having or being prone to a muscle weakness disease (e.g., HPP) to generate a BOT-2 score for the subject.

The BOT-2 includes a range of tests to evaluate physical impairments of a subject, which can be performed with, e.g., a kit including the tests. The BOT-2 provides composite BOT-2 scores in the following areas: strength, running speed and agility, fine motor precision, fine motor integration, manual dexterity, bilateral coordination, balance, and upper-limb coordination. For example, a subject having or being prone to a muscle weakness disease can perform sit-ups, v-ups, standing long jump, wall sit, and/or push-ups to determine the BOT-2 strength score; a subject having or being prone to a muscle weakness disease can step over a balance beam and/or perform a shuttle run, two-legged side hop, and/or one-legged side hop to determine the BOT-2 running speed and agility score; a subject having or being prone to a muscle weakness disease can cut out a circle and/or connect dots to determine the BOT-2 fine motor precision score; a subject having or being prone to a muscle weakness disease can copy a star and/or copy a square to determine the BOT-2 fine motor integration score; a subject having or being prone to a muscle weakness disease can transfer pennies, sort cards, and/or string blocks to determine the manual dexterity score; a subject having or being prone to a muscle weakness disease can tap his or her foot and finger and/or perform jumping jacks to determine the BOT-2 bilateral coordination score; a subject having or being prone to a muscle weakness disease can walk forward on a line and/or stand on one leg on a balance beam to determine the BOT-2 balance score; and a subject having or being prone to a muscle weakness disease can throw a ball at a target and/or catch a tossed ball to determine the BOT-2 upper-limb coordination score.

A subject having or being prone to a muscle weakness disease (e.g., HPP) could perform tests in one or more of described areas (strength, running speed and agility, fine motor precision, fine motor integration, manual dexterity, bilateral coordination, balance, and upper-limb coordination) to generate a BOT-2 score indicative of physical impairments in the subject. Within each BOT-2 area (strength, running speed and agility, fine motor precision, fine motor integration, manual dexterity, bilateral coordination, balance, and upper-limb coordination), such subject could perform one or more tests to determine the BOT-2 score of the subject, e.g., the subject could perform one or more of sit-ups, v-ups, standing long jump, wall sit, and push-ups to determine the BOT-2 strength score. Thus, only one test (e.g., one test selected from the group of sit-ups, v-ups, standing long jump, wall sit, and push-ups) can be performed to determine the BOT-2 score (e.g., a BOT-2 strength score) of a subject having or being prone to a muscle weakness disease (e.g., HPP).

Each of the BOT-2 scores (strength, running speed and agility, fine motor precision, fine motor integration, manual dexterity, bilateral coordination, balance, and upper-limb coordination) of the subject having or being prone to a muscle weakness disease (e.g., HPP) can be compared to the BOT-2 score of a subject without the muscle weakness disease (e.g., HPP) to, e.g., determine the standard deviation of the BOT-2 score. Each of the BOT-2 scores (e.g., strength, running speed and agility, fine motor precision, fine motor integration, manual dexterity, bilateral coordination, balance, and upper-limb coordination) of the subject having or being prone to a muscle weakness disease (e.g., HPP) can be compared to the BOT-2 score of other subjects having or being prone to the muscle weakness disease (e.g., HPP) to, e.g., determine the average BOT-2 score for the subject.

BOT-2 scores (e.g., strength, running speed and agility, fine motor precision, fine motor integration, manual dexterity, bilateral coordination, balance, and upper-limb coordination scores) range from about 0 to equal to or less than about 25, in which a score of about 10 to about 20 is considered representative of healthy subject (e.g., subject without the muscle weakness disease (e.g., HPP)). Subjects with an average BOT-2 score (e.g., strength, running speed and agility, fine motor precision, fine motor integration, manual dexterity, bilateral coordination, balance, and upper-limb coordination scores) of less than about 10 can be treated with an alkaline phosphatase, or a polypeptide having alkaline phosphatase activity, e.g., sALP, such as TNALP, for example the sALP polypeptide of SEQ ID NO: 1 or a polypeptide variant having at least 95% sequence identity to the sequence of SEQ ID NO: 1, e.g., asfotase alfa.

For example, subjects having or being prone to a muscle weakness disease with a BOT-2 strength score of less than 10 (e.g., about 0, about 1, about 2, about 3, about 4, about 5, about 6, about 7, about 8, about 9, or about 10) can be treated with a sALP (such as TNALP, for example the sALP polypeptide of SEQ ID NO: 1 or a polypeptide variant having at least 95% sequence identity to the sequence of SEQ ID NO: 1, e.g., asfotase alfa) for a period of time, up to the lifetime of the patient. Likewise, subjects having or being prone to a muscle weakness disease with a BOT-2 running speed and agility score of less than 10 (e.g., about 0, about 1, about 2, about 3, about 4, about 5, about 6, about 7, about 8, about 9, or about 10) can then be treated with a sALP (such as TNALP, for example the sALP polypeptide of SEQ ID NO: 1 or a polypeptide variant having at least 95% sequence identity to the sequence of SEQ ID NO: 1, e.g., asfotase alfa) for a period of time, up to the lifetime of the subject.

The methods can result in an improvement in the BOT-2 score (e.g., strength, running speed and agility, fine motor precision, fine motor integration, manual dexterity, bilateral coordination, balance, and/or upper-limb coordination score) of a subject having or being prone to a muscle weakness disease (e.g., HPP). For example, treatment with an alkaline phosphatase, or a polypeptide having alkaline phosphatase activity, such as a sALP (e.g., TNALP, for example the sALP polypeptide of SEQ ID NO: 1 or a polypeptide variant having at least 95% sequence identity to the sequence of SEQ ID NO: 1, e.g., asfotase alfa), such as treatment with a sALP for a period of time, can result in an average increase in the BOT-2 strength score to about 10 to about 20 (e.g. about 10, about 11, about 12, about 13, about 14, about 15, about 16, about 17, about 18, about 19, or about 20). Additionally, treatment with a sALP (such as TNALP, for example the sALP polypeptide of SEQ ID NO: 1 or a polypeptide variant having at least 95% sequence identity to the sequence of SEQ ID NO: 1, e.g., asfotase alfa) can result in an average increase in the BOT-2 running speed and agility score to about 5 to about 20 (e.g. about 5, about 6, about 7, about 8, about 9, about 10, about 11, about 12, about 13, about 14, about 15, about 16, about 17, about 18, about 19, or about 20).

The increase in the BOT-2 score (e.g., strength, running speed and agility, fine motor precision, fine motor integration, manual dexterity, bilateral coordination, balance, and/or upper-limb coordination score) can be sustained throughout administration of the alkaline phosphatase, or the polypeptide having alkaline phosphatase activity, such as sALP (e.g., TNALP, for example the sALP polypeptide of SEQ ID NO: 1 or a polypeptide variant having at least 95% sequence identity to the sequence of SEQ ID NO: 1, e.g., asfotase alfa), e.g., for a period of time. Likewise, the decrease in physical impairments of muscles after administration of the alkaline phosphatase, or the polypeptide having alkaline phosphatase activity, can be sustained throughout administration of the alkaline phosphatase, or the polypeptide having alkaline phosphatase activity.

The BOT-2 scores (strength, running speed and agility, fine motor precision, fine motor integration, manual dexterity, bilateral coordination, balance, and upper-limb coordination scores) of a subject having or being prone to a muscle weakness disease (such as, HPP) can be used singly or in combination to other endpoints for assessing treatment efficacy using an alkaline phosphatase, or a polypeptide having alkaline phosphatase activity, such as sALP (e.g., TNALP, for example the sALP polypeptide of SEQ ID NO: 1 or a polypeptide variant having at least 95% sequence identity to the sequence of SEQ ID NO: 1, e.g., asfotase alfa), in which improvements relative to a certain test score demonstrate that the alkaline phosphatase, or the polypeptide having alkaline phosphatase activity, is effective for treating muscle impairments associated with the muscle weakness disease. For example, when administration of a sALP to a subject having or being prone to a muscle weakness disease results in an average increase in the BOT-2 running speed and agility score to about 5 or greater than about 5, in which the subject previously had an average BOT-2 running speed and agility score of less than about 5, then the sALP is considered to be effective at, e.g., treating physical impairments associated with a muscle weakness disease.

Additionally, within each BOT-2 area (strength, running speed and agility, fine motor precision, fine motor integration, manual dexterity, bilateral coordination, balance, and upper-limb coordination), a subject having or being prone to a muscle weakness disease (e.g., HPP, CPPD, familial hypophosphatemia described herein, etc.) could perform one or more tests to determine the BOT-2 score of the subject. For instance, a subject having or being prone to a muscle weakness disease could perform one or more of sit-ups, v-ups, standing long jump, wall sit, and push-ups to determine the BOT-2 strength score, to determine the BOT-2 strength score and assess the treatment efficacy of sALP administration. The subject having or being prone to a muscle weakness disease can perform one or more of balance beam, a shuttle run, two-legged side hop, and/or one-legged side hop to determine the BOT-2 running speed and agility score and assess the treatment efficacy of sALP administration. The subject having or being prone to a muscle weakness disease can cut out a circle and/or connect dots to determine the BOT-2 fine motor precision score and assess the treatment efficacy of sALP administration. The subject having or being prone to a muscle weakness disease can copy a star and/or copy a square to determine the BOT-2 fine motor integration score and assess the treatment efficacy of sALP administration. The subject having or being prone to a muscle weakness disease could perform one or more of transferring pennies, sorting cards, and stringing blocks to determine the BOT-2 manual dexterity score and assess the treatment efficacy of sALP administration. The subject having or being prone to a muscle weakness disease can tap his or her foot and finger and/or perform jumping jacks to determine the BOT-2 bilateral coordination score and assess the treatment efficacy of sALP administration. The subject having or being prone to a muscle weakness disease can walk forward on a line and/or stand on one leg on a balance beam to determine the BOT-2 balance score and assess the treatment efficacy of sALP administration. The subject having or being prone to a muscle weakness disease can throw a ball at a target and/or catch a tossed ball to determine the BOT-2 upper-limb coordination score and assess the treatment efficacy of sALP administration.

Alternatively, when administration of an alkaline phosphatase, or a polypeptide having alkaline phosphatase activity, such as a sALP, does not result in an average increase in the BOT-2 running speed and agility score to greater than about 5, the dosage and/or frequency of administration can be changed in order to determine the effective amount of the alkaline phosphatase, or the polypeptide having alkaline phosphatase activity, for the subject having or being prone to the muscle weakness disease (e.g., HPP). For instance, the dosage of the sALP (such as TNALP, for example the sALP polypeptide of SEQ ID NO: 1 or a polypeptide variant having at least 95% sequence identity to the sequence of SEQ ID NO: 1, e.g., asfotase alfa) can be increased from, e.g., about 3 mg/kg/week to about 6 mg/kg/week or about 6 mg/kg/week to about 9 mg/kg/wk.

Childhood Health Assessment Questionnaire (CHAQ)

The Childhood Health Assessment Questionnaire (CHAQ) can be administered to evaluate the health status of children having a muscle weakness disease (e.g., HPP) to generate a CHAQ index score for the child, as is described in Bruce & Fries (*J. Rheumatol.* 30(1): 167-178, 2003) and Klepper (*Arthritis & Rheumatism,* 49: S5-S14, 2003), hereby incorporated by reference in their entirety. The CHAQ includes eight categories of questions for dressing/grooming, arising, eating, walking, hygiene, reach, grip, and activities, in which a parent or guardian records the amount of difficulty the child with the muscle weakness disease (e.g., HPP) has in performing the respective activities. The range of scores within each category is from 0 to 3, in which a score of 0 indicates without any difficulty; a score of 1 indicates with some difficulty; a score of 2 indicates with much difficulty; and a score of 3 indicates that the child is unable to perform the activity.

Children having or being prone to a muscle weakness disease with an average CHAQ index score (e.g., indicative of disability in activities of daily living (ADL) and/or pain) greater than about 0.8 (e.g., about 0.8, about 1, about 1.2, about 1.4, about 1.6, about 1.8, about 2.0, about 2.2, about 2.4, about 2.6, about 2.8, or about 3.0) can be treated by administering an alkaline phosphatase, or a polypeptide having alkaline phosphatase activity, such as sALP (e.g., TNALP, for example the sALP polypeptide of SEQ ID NO: 1 or a polypeptide variant having at least 95% sequence identity to the sequence of SEQ ID NO: 1, e.g., asfotase alfa). For example, children with an average CHAQ index score of greater than about 0.8 can be treated by administering an alkaline phosphatase, or a polypeptide having alkaline phosphatase activity, such as sALP (e.g., TNALP, for example the sALP polypeptide of SEQ ID NO: 1 or a polypeptide variant having at least 95% sequence identity to the sequence of SEQ ID NO: 1, e.g., asfotase alfa) for a period of time, up to the lifetime of the patient. Furthermore, a child having or being prone to a muscle weakness disease disclosed herein could be asked one or more questions in one or more of the eight categories (dressing/grooming, arising, eating, walking, hygiene, reach, grip, and activities) to arrive at an average CHAQ index score, and if the average CHAQ index score is greater than about 0.8, the child can be treated by administering an alkaline phosphatase, or a polypeptide having alkaline phosphatase activity, such as a sALP.

The CHAQ index score of a child having or being prone to a muscle weakness disease disclosed herein can be compared to the CHAQ index score of children without such muscle weakness disease to, e.g., determine the standard deviation of the CHAQ index score. Additionally, the CHAQ index score of a child having or being prone to a muscle weakness disease disclosed herein can be compared to the CHAQ index score of other children having or being prone to the muscle weakness disease disclosed herein to, e.g., determine the standard deviation of the CHAQ index score.

The methods can result in an improvement in the CHAQ index score (e.g., indicative of disability in ADL and/or pain) of the child having or being prone to a muscle weakness disease disclosed herein. For example, treatment with a sALP (such as TNALP, for example the sALP polypeptide of SEQ ID NO: 1 or a polypeptide variant having at least 95% sequence identity to the sequence of SEQ ID NO: 1, e.g., asfotase alfa), such as treatment with a sALP for a period of time, up to the lifetime of the child, can result in an average decrease in the CHAQ index score to about 0 to equal to or less than about 0.5 (e.g. about 0, about 0.1, about 0.2, about 0.4, or about 0.5) in children with HPP.

The decrease in the CHAQ index score of the child having or being prone to a muscle weakness disease (e.g., HPP) can be sustained throughout administration of the alkaline phosphatase, or the polypeptide having alkaline phosphatase activity, such as sALP (e.g., TNALP, for example the sALP polypeptide of SEQ ID NO: 1 or a polypeptide variant having at least 95% sequence identity to the sequence of SEQ ID NO: 1, e.g., asfotase alfa), e.g., for a period of time, up to the lifetime of the child. Likewise, the increase in ADL and/or decrease in pain of the child can be sustained throughout administration of the sALP (such as TNALP, for example the sALP polypeptide of SEQ ID NO: 1 or a polypeptide variant having at least 95% sequence identity to the sequence of SEQ ID NO: 1, e.g., asfotase alfa), for a period of time, up to the lifetime of the child.

The CHAQ index score of a child having or being prone to a muscle weakness disease (e.g., HPP) can be used to assess treatment efficacy using an alkaline phosphatase, or a polypeptide having alkaline phosphatase activity, such as sALP (e.g., TNALP, for example the sALP polypeptide of SEQ ID NO: 1 or a polypeptide variant having at least 95% sequence identity to the sequence of SEQ ID NO: 1, e.g., asfotase alfa), in which improvements relative to a certain test score demonstrate that the alkaline phosphatase, or the polypeptide having alkaline phosphatase activity, is effective for treating, e.g., disability in activities of daily living (ADL) and pain associated with the muscle weakness disease. In particular, a child having or being prone to a muscle weakness disease could be asked one or more questions in one or more of the eight categories (dressing/grooming, arising, eating, walking, hygiene, reach, grip, and activities) to arrive at an average CHAQ index score and to assess treatment efficacy of sALP administration. For example, when administration of a sALP to a child having or being prone to a muscle weakness disease results in an average decrease in the CHAQ index score to equal to or less than about 0.5, in which the child previously had an average CHAQ index score of greater than about 0.8, then the sALP is effective at treating, e.g., disability in activities of daily living (ADL) and pain associated with a muscle weakness disease. Alternatively, when administration of a sALP does not result in an average decrease in the CHAQ index score to equal to or less than about 0.5, the dosage and/or frequency of sALP administration can be changed in order to determine the effective amount of the sALP for the child having or being prone to a muscle weakness disease. For instance, the dosage of the sALP (such as TNALP, for example the sALP polypeptide of SEQ ID NO: 1 or a polypeptide variant having at least 95% sequence identity to the sequence of SEQ ID NO: 1, e.g., asfotase alfa) can be increased from, e.g., about 3 mg/kg/week to about 6 mg/kg/week or about 6 mg/kg/week to about 9 mg/kg/wk.

Pediatric Outcomes Data Collection Instrument (PODCI)

Certain subjects having or being prone to a muscle weakness disease (e.g., HPP) can be identified for treatment with an alkaline phosphatase, or a polypeptide having alkaline phosphatase activity, such as sALP (e.g., TNALP, for example the sALP polypeptide of SEQ ID NO: 1 or a polypeptide variant having at least 95% sequence identity to the sequence of SEQ ID NO: 1, e.g., asfotase alfa) using the Pediatric Outcomes Data Collection Instrument (PODCI). The PODCI can be administered to evaluate the health status of children to generate a PODCI score for the patient, as is described in Plint et al. (*J. Pediatr. Orthop.* 23(6): 788-790, 2003). The PODCI includes eight categories of questions that can be completed by a subject having or being prone to a muscle weakness disease (e.g., HPP) or by a parent/guardian of the subject. Categories that can be used to determine the PODCI of a subject having or being prone to a muscle weakness disease include the following: 1) the upper extremity and physical function scale to measure difficulty encountered in performing daily personal care and student activities; 2) the transfer and basic mobility scale to measure difficulty experienced in performing routine motion and motor activities in daily activities; 3) the sports/physical functioning scale to measure difficulty or limitations encountered in participating in more active activities or sports; 4) the pain/comfort scale to measure the level of pain experienced during the past week; 5) the treatment expectations scale to measure the long term expectations of treatment; 6) the happiness scale to measure overall satisfaction with personal looks and sense of similarity to friends and others of own age; 7) the satisfaction with symptoms scale to measure the patient's acceptance of current limitations should this be a life-long state; and 8) the global functioning scale, which is a general combined scale calculated from the first four scales listed above. In each of the categories, a standardized score is determined for the subject having or being prone to a muscle weakness disease and then converted to a 0 to 100 scale, in which 0 represents significant disability and 100 represents less disability.

Subjects having or being prone to a muscle weakness disease (e.g., HPP) with an average PODCI score (e.g., indicative of disability in ADL and/or pain) less than about 40 (e.g., about 5, about 10, about 15, about 20, about 25, about 30, about 35, or about 39) can be treated by administering an alkaline phosphatase, or a polypeptide having alkaline phosphatase activity, such as a sALP (e.g., TNALP, for example the sALP polypeptide of SEQ ID NO: 1 or a polypeptide variant having at least 95% sequence identity to the sequence of SEQ ID NO: 1, e.g., asfotase alfa). For example, subjects with an average PODCI score of less than 40 can be treated by administering a sALP for a period of time, up to the lifetime of the patient. Furthermore, a subject having or being prone to a muscle weakness disease could be asked one or more questions in one or more of the eight scales described above (e.g., transfer and basic mobility, sports/physical functioning, and the pain/comfort scale) to arrive at an average PODCI score, and if the average PODCI score is greater than less than 40, the patient can be treated by administering a sALP.

The methods described herein can result in an increase in the PODCI score (e.g., indicative of disability in ADL and/or pain) of the subject having or being prone to a muscle weakness disease. For example, treatment with an alkaline phosphatase, or a polypeptide having alkaline phosphatase activity, such as a sALP (e.g., TNALP, for example the sALP polypeptide of SEQ ID NO: 1 or a polypeptide variant having at least 95% sequence identity to the sequence of SEQ ID NO: 1, e.g., asfotase alfa), such as treatment with a sALP for a period of time, up to the lifetime of the subject, can result in an average increase in the PODCI score to about 40 to about 50 (e.g. about 40, about 41, about 42, about 43, about 44, about 45, about 46, about 47, about 48, about 49, or about 50).

The increase in the PODCI score can be sustained throughout administration of the alkaline phosphatase, or the polypeptide having alkaline phosphatase activity, such as the sALP (e.g., TNALP, for example the sALP polypeptide of SEQ ID NO: 1 or a polypeptide variant having at least 95% sequence identity to the sequence of SEQ ID NO: 1, e.g., asfotase alfa), e.g., for a period of time, up to the lifetime of the subject having or being prone to a muscle weakness disease. Likewise, the increase in ADL and/or decrease in pain can be sustained throughout administration of the sALP (such as TNALP, for example the sALP polypeptide of SEQ ID NO: 1 or a polypeptide variant having at least 95% sequence identity to the sequence of SEQ ID NO: 1, e.g., asfotase alfa), for a period of time, up to the lifetime of the subject.

The PODCI score of a subject having or being prone to a muscle weakness disease (e.g., HPP) can be used to assess treatment efficacy using an alkaline phosphatase, or a polypeptide having alkaline phosphatase activity, such as a sALP (e.g., TNALP, for example the sALP polypeptide of SEQ ID NO: 1 or a polypeptide variant having at least 95% sequence identity to the sequence of SEQ ID NO: 1, e.g., asfotase alfa), in which improvements relative to a certain test score demonstrate that the alkaline phosphatase, or the polypeptide having alkaline phosphatase activity, is effective for treating, e.g., disability in activities of daily living (ADL) and pain associated with the muscle weakness disease. In particular, a subject having or being prone to a muscle weakness disease could be asked one or more questions in one or more of the eight scales (the upper extremity and physical function scale, the transfer and basic mobility scale, the sports/physical functioning scale, the pain/comfort scale, the treatment expectations scale, the happiness scale, the satisfaction with symptoms scale, and the global functioning scale) to arrive at an average PODCI score and to assess treatment efficacy of sALP administration.

For example, when administration of a sALP to a subject having or being prone to a muscle weakness disease results in an average increase in the PODCI score to about 40 or greater than about 40, in which the subject previously had an average PODCI score of less than about 40, then the sALP is effective at treating, e.g., disability in activities of daily living (ADL) and pain associated with a muscle weakness disease. Alternatively, when administration of a sALP does not result in an average increase in the PODCI score to about 40 or greater than about 40, the dosage and frequency of sALP administration can be changed in order to determine the effective amount of the sALP for the subject having or being prone to a muscle weakness disease. For instance, the dosage of the sALP (such as TNALP, for example the sALP polypeptide of SEQ ID NO: 1 or a polypeptide variant having at least 95% sequence identity to the sequence of SEQ ID NO: 1, e.g., asfotase alfa) can be increased from, e.g., about 3 mg/kg/week to about 6 mg/kg/week or about 6 mg/kg/week to about 9 mg/kg/wk.

Bayley Scales of Infant and Toddler Development, $3^{rd}$ Edition (BSID-III)

Another endpoint, the Bayley Scales of Infant and Toddler Development, $3^{rd}$ Edition (BSID-III) can be administered to evaluate the health status of a subject having or being prone to a muscle weakness disease (e.g., HPP) from birth to generate a BSID-III score for the subject, as is described in Bayley. (2006). *Bayley scales of infant and toddler development: administration manual.* San Antonio, Tex.: Harcourt Assessment. The BSID-III includes a series of developmental play tasks that can be administered to the subject to determine the raw BSID-III score. For example, categories for determining the BSID-III score of a subject having or being prone to a muscle weakness disease (e.g., infants of about three years of age or less having HPP) can include prehension, perceptual-motor integration, motor planning and speed, visual tracking, reaching, object grasping, object manipulation, functional hand skills, responses to tactile information, movement of the limbs and torso, static positioning, dynamic movement, balance, and motor planning. The BSID-III measurements are then converted to scaled BSID-III scores, which can be used to determine the subject's performance compared to healthy, age-adjusted subjects. The BSID-III scaled score of a subject having or being prone to a muscle weakness disease (e.g., a patient with HPP) can range from 0 to 14, in which scores of about 7 to about 13 are considered the normal range of healthy subjects.

A subject having or being prone to a muscle weakness disease could perform tests in one or more of described categories (prehension, perceptual-motor integration, motor planning and speed, visual tracking, reaching, object grasping, object manipulation, functional hand skills, responses to tactile information, movement of the limbs and torso, static positioning, dynamic movement, balance, and motor planning) as an infant (e.g., at about 3 years of age or less than 3 years of age) to generate a BSID-III score indicative of delayed motor development. Subjects having or being prone to a muscle weakness disease with an average BSID-III score in one or more of the described categories (prehension, perceptual-motor integration, motor planning and speed, visual tracking, reaching, object grasping, object manipulation, functional hand skills, responses to tactile information, movement of the limbs and torso, static positioning, dynamic movement, balance, and motor planning) less than about 2 as an infant can be treated by administering a sALP (such as TNALP, for example the sALP polypeptide of SEQ ID NO: 1 or a polypeptide variant having at least 95% sequence identity to the sequence of SEQ ID NO: 1, e.g., asfotase alfa). In particular, subjects having or being prone to a muscle weakness disease with an average BSID-III score of less than about 2 as an infant can be treated by administering a sALP for a period of time, up to the lifetime of the subject.

The methods can result in an improvement in the average BSID-III score (e.g., indicative of delayed motor development) of the subject having or being prone to a muscle weakness disease. For example, treatment with a sALP (such as TNALP, for example the sALP polypeptide of SEQ ID NO: 1 or a polypeptide variant having at least 95% sequence identity to the sequence of SEQ ID NO: 1, e.g., asfotase alfa), such as treatment with a sALP for a period of time, up to the lifetime of the subject, can result in an average increase in the BSID-III score to greater than about 5 (e.g., about 5, about 6, about 7, about 8, about 9, about 10, about 11, about 12, or about 13).

The increase in the BSID-III score can be sustained throughout administration of the alkaline phosphatase, or the polypeptide having alkaline phosphatase activity, such as a sALP (e.g., TNALP, for example the sALP polypeptide of SEQ ID NO: 1 or a polypeptide variant having at least 95% sequence identity to the sequence of SEQ ID NO: 1, e.g., asfotase alfa), for a period of time, up to the lifetime of the subject having or being prone to a muscle weakness disease. Likewise, the increase in motor development can be sustained throughout administration of the alkaline phosphatase, or the polypeptide having alkaline phosphatase activity, such as a sALP (e.g., TNALP, for example the sALP polypeptide of SEQ ID NO: 1 or a polypeptide variant having at least 95% sequence identity to the sequence of SEQ ID NO: 1, e.g., asfotase alfa), e.g., for a period of time, up to the lifetime of the subject.

The BSID-III score of a subject having or being prone to a muscle weakness disease (e.g., HPP) can be used to assess treatment efficacy using an alkaline phosphatase, or a polypeptide having alkaline phosphatase activity, such as a sALP (e.g., TNALP, for example the sALP polypeptide of SEQ ID NO: 1 or a polypeptide variant having at least 95% sequence identity to the sequence of SEQ ID NO: 1, e.g., asfotase alfa), in which improvements relative to a certain test score demonstrate that the alkaline phosphatase, or the polypeptide having alkaline phosphatase activity, is effective for treating, e.g., delayed motor development associated with the muscle weakness disease. In particular, a subject having or being prone to a muscle weakness disease could perform tests in one or more of described categories (prehension, perceptual-motor integration, motor planning and speed, visual tracking, reaching, object grasping, object manipulation, functional hand skills, responses to tactile information, movement of the limbs and torso, static positioning, dynamic movement, balance, and motor planning) as an infant (e.g., at about three years of age or less having HPP) to arrive at an average BSID-III score and to assess treatment efficacy of sALP administration.

For example, when administration of a sALP to a child having or being prone to a muscle weakness disease results in an average increase in the BSID-III scaled score to greater than about 5, in which the child previously had an average BSID-III scaled score of less than about 2 as an infant (e.g., at about 3 years of age or less than 3 years of age), then the sALP is effective at treating, e.g., delayed motor development associated with HPP. Alternatively, when administration of a sALP does not result in an average increase in the BSID-III scaled score to greater than about 5, the dosage and/or frequency of sALP administration can be changed in order to determine the effective amount of the sALP for the child having or being prone to a muscle weakness disease. For instance, the dosage of the sALP (such as TNALP, for example the sALP polypeptide of SEQ ID NO: 1 or a polypeptide variant having at least 95% sequence identity to the sequence of SEQ ID NO: 1, e.g., asfotase alfa) can be increased from, e.g., about 3 mg/kg/week to about 6 mg/kg/week or about 6 mg/kg/week to about 9 mg/kg/wk.

Peabody Developmental Motor Scales, 2nd Edition (PDMS-2)

Another endpoints, the Peabody Developmental Motor Scales, 2nd Edition (PDMS-2), can be administered to evaluate the health status of a subject having or being prone to a muscle weakness disease (e.g., HPP) from birth to generate a PDMS-2 score for the subject, as is described in van Hartingsveldt et al. (*Occup. Ther. Int.* 12(1): 1-13, 2005). The PDMS-2 includes six categories of subtests to measure motor skills of the subject, such as a patient having HPP.

In particular, PDMS-2 measurements can be determined from the following subtests: 1) the locomotor subtest to measure a subject's ability to move from one place to another (measurements include crawling, walking, running, hopping, and jumping forward); 2) the reflexes subtest to measure a subject's ability to automatically react to environmental events; 3) the stationary subtest to measure a subject's ability to sustain body control within the center of gravity and retain equilibrium; 4) the object manipulation subtest to measure a subject's ability to manipulate an object, such as catching, throwing, and kicking a ball; 5) the grasping subtest to measure a subject's ability to use his or her hands, such as the ability to hold an object with one hand and actions involving the controlled use of the fingers of both hands; and 6) the visual-motor integration subtest to measure a subject's ability to use his or her visual perceptual skills to perform complex eye-hand coordination tasks, such as reaching and grasping for an object, building with blocks, and copying designs. The PDMS-2 measurement can be determined for one or more of these categories for a subject having or being prone to a muscle weakness disease (e.g., HPP) and then converted into a PDMS-2 score, such as the PDMS-2 locomotor standard score ranging from 0 to 13, in which the range of healthy subjects (e.g., subjects without the muscle weakness disease) is from about 7 to about 13.

Subjects having or being prone to a muscle weakness disease with an average PDMS-score (e.g., indicative of delayed motor development) can be treated by administering a sALP (such as TNALP, for example the sALP polypeptide of SEQ ID NO: 1 or a polypeptide variant having at least 95% sequence identity to the sequence of SEQ ID NO: 1, e.g., asfotase alfa).

The methods described herein can result in an improvement in the PDMS-2 score (e.g., indicative of delayed motor development) of the subject having or being prone to a muscle weakness disease. For example, treatment with an alkaline phosphatase, or a polypeptide having alkaline phosphatase activity, such as a sALP (e.g., TNALP, for example the sALP polypeptide of SEQ ID NO: 1 or a polypeptide variant having at least 95% sequence identity to the sequence of SEQ ID NO: 1, e.g., asfotase alfa), can result in an average increase in the PDMS-2 score to about 7 to about 13 (e.g., about 7, about 8, about 9, about 10, about 11, about 12, or about 13).

The increase in the PDMS-2 score can be sustained throughout administration of the alkaline phosphatase, or the polypeptide having alkaline phosphatase activity, such as sALP (e.g., TNALP, for example the sALP polypeptide of SEQ ID NO: 1 or a polypeptide variant having at least 95% sequence identity to the sequence of SEQ ID NO: 1, e.g., asfotase alfa), for an elongated time, e.g., for a period of time, up to the lifetime of the subject having or being prone to a muscle weakness disease. Likewise, the increase in motor development can be sustained throughout administration of the sALP (such as TNALP, for example the sALP polypeptide of SEQ ID NO: 1 or a polypeptide variant having at least 95% sequence identity to the sequence of SEQ ID NO: 1, e.g., asfotase alfa) for a period of time, up to the lifetime of the subject having or being prone to a muscle weakness disease.

The PDMS-2 score of a subject having or being prone to a muscle weakness disease (e.g., HPP) can be used to assess treatment efficacy using an alkaline phosphatase, or a polypeptide having alkaline phosphatase activity, such as a sALP (e.g., TNALP, for example the sALP polypeptide of SEQ ID NO: 1 or a polypeptide variant having at least 95% sequence identity to the sequence of SEQ ID NO: 1, e.g., asfotase alfa), in which improvements relative to a certain test score demonstrate that the alkaline phosphatase, or the polypeptide having alkaline phosphatase activity, is effective for treating, e.g., delayed motor development associated with the muscle weakness disease. For example, a child having or being prone to a muscle weakness disease could perform tests in one or more of described categories (locomotor, reflexes, stationary, object manipulation, grasping, and visual-motor) at about 5 years of age or less than 5 years of age to arrive at an average PDMS-2 score and to assess treatment efficacy of sALP administration.

For example, when administration of a sALP to a child having or being prone to a muscle weakness disease results in an average increase in the PDMS-2 standard score to about 7, in which the child previously had an average PDMS-2 standard score of about 5, then the sALP is effective at treating, e.g., delayed motor development associated with HPP. Alternatively, when administration of a sALP does not result in an average increase in the PDMS-2 standard score to about 7, the dosage and/or frequency of sALP administration can be changed in order to determine the effective amount of the sALP for the child. For instance, the dosage of the sALP (such as TNALP, for example the sALP polypeptide of SEQ ID NO: 1 or a polypeptide variant having at least 95% sequence identity to the sequence of SEQ ID NO: 1, e.g., asfotase alfa) can be increased from, e.g., about 3 mg/kg/week to about 6 mg/kg/week or about 6 mg/kg/week to about 9 mg/kg/wk.

Six Minute Walk Test (6 MWT)

A subject having a muscle weakness disease can be identified for treatment with an alkaline phosphatase or a polypeptide having alkaline phosphatase activity (e.g. a sALP, such as TNALP, for example the sALP polypeptide of SEQ ID NO: 1 or a polypeptide variant having at least 95% sequence identity to the sequence of SEQ ID NO: 1, e.g., asfotase alfa) using the 6 MWT. In particular, the 6 MWT can be used to evaluate walking ability in an adult having a muscle weakness disease to generate a 6 MWT value for the adult. The 6 MWT can be performed indoors or outdoors using a flat, straight, enclosed corridor (e.g., of about 30 meters in length) with a hard surface. A stopwatch or other timer can be used to track the time and a mechanical counter or other device can be used to determine the distance (e.g., in meters) that the subject having a muscle weakness disease walks. For instance, the length of the corridor can be marked every three meters to determine the number of meters walked by the subject having a muscle weakness disease, with the turnaround point at 30 meters and the starting line also marked. The distance walked by the subject having a muscle weakness disease in six minutes can then be compared to the predicted number of meters walked, e.g., by a normal subject of about the same age, the same gender, and/or the same height, and expressed as a percentage value to generate the 6 MWT value of the subject. The 6 MWT value of the subject having a muscle weakness disease can be compared to the 6 MWT value at baseline of the subject. Additionally, the 6 MWT value of the subject having a muscle weakness disease can be compared to the 6 MWT value of a normal subject.

Subjects having a muscle weakness disease with an average 6 MWT of less than about 80% of the predicted 6 MWT value (e.g., relative to a normal subject of about the same age, the same gender, and/or the same height) can be treated with an alkaline phosphatase or a polypeptide having alkaline phosphatase activity (e.g. a sALP, such as TNALP, for example the sALP polypeptide of SEQ ID NO: 1 or a polypeptide variant having at least 95% sequence identity to the sequence of SEQ ID NO: 1, e.g., asfotase alfa), such as by administering an alkaline phosphatase or a polypeptide having alkaline phosphatase activity for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks). For example, a subject having a muscle weakness disease with an average 6 MWT of less than about 80% of the predicted 6 MWT value (e.g., about 50%, about 55%, about 60%, about 65%, about 70%, or about 75% of the predicted 6 MWT value) can be treated with an alkaline phosphatase or a polypeptide having alkaline phosphatase activity for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks).

The methods can result in an improvement in the 6 MWT value of a subject having a muscle weakness disease. For example, treatment with an alkaline phosphatase or a polypeptide having alkaline phosphatase activity (e.g. a sALP, such as TNALP, for example the sALP polypeptide of SEQ ID NO: 1 or a polypeptide variant having at least 95% sequence identity to the sequence of SEQ ID NO: 1, e.g., asfotase alfa), such as treatment with an alkaline phosphatase or a polypeptide having alkaline phosphatase activity for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks), can result in an average increase in the 6 MWT value to about 80% or greater of the predicted 6 MWT value of the patient (e.g. about 82%, about 84%, about 86%, about 88%, about 90%, about 92%, about 94%, about 96%, about 98%, or more of the predictive 6 MWT value).

The increase in the 6 MWT value of the subject having a muscle weakness disease can be sustained throughout administration of the alkaline phosphatase or a polypeptide having alkaline phosphatase activity (e.g. a sALP, such as TNALP, for example the sALP polypeptide of SEQ ID NO: 1 or a polypeptide variant having at least 95% sequence identity to the sequence of SEQ ID NO: 1, e.g., asfotase alfa), e.g., for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the subject; particularly at least six weeks). For instance, the 6 MWT value increases to greater than about 80% of the predicted 6 MWT value of the subject having a muscle weakness disease and remains at ±10% of the increased 6 MWT value during treatment with the alkaline phosphatase or a polypeptide having alkaline phosphatase activity.

Likewise, the improvement in walking ability of the subject having a muscle weakness disease can be sustained throughout administration of the alkaline phosphatase or a polypeptide having alkaline phosphatase activity, e.g., for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks). For instance, the subject having a muscle weakness disease exhibits decreased reliance on an assistive mobility device, such as a walker, a wheelchair, braces, crutches, or orthotics, during treatment with the sALP.

Alternatively, when administration of an alkaline phosphatase or a polypeptide having alkaline phosphatase activity (e.g. a sALP, such as TNALP, for example the sALP polypeptide of SEQ ID NO: 1 or a polypeptide variant having at least 95% sequence identity to the sequence of SEQ ID NO: 1, e.g., asfotase alfa) does not result in an average increase in the 6 MWT value to greater than 80% of the predicted 6 MWT value (e.g., of a normal subject of about the same age, same gender, and/or height), the dosage and/or frequency of alkaline phosphatase or a polypeptide having alkaline phosphatase activity administration can be changed in order to determine the effective amount of the alkaline phosphatase or a polypeptide having alkaline phosphatase activity for the subject having a muscle weakness disease. For instance, the dosage of the alkaline phosphatase or a polypeptide having alkaline phosphatase activity can be increased from, e.g., about 2.1 mg/kg/week or about 3.5 mg/kg/week to about 6 mg/kg/week or about 9 mg/kg/week.

Handheld Dynamometry (HHD)

The grip and muscle strength of subjects having or being prone to a muscle weakness disease can be assessed using Hand Held Dynamometry (HHD). For example, knee flexion and extension and also hip flexion, extension, and abduction of a subject having or being prone to a muscle weakness disease can be measured using, e.g., a MICRO-FET2™ Dynamometer, while grip strength of the subject can be measured using, e.g., a Jamar Grip Dynamometer. In particular, the administrator holds the dynamometer stationary, and the subject exerts a maximal force against the dynamometer. Peak force data is collected in pounds, then converted to Newtons (N). Torque values are then calculated using limb length in N-meters. The torque value can then be compared to the torque value of, e.g., a normal subject of about the same age, the same gender, and/or the same height, and expressed as a percentage value to generate the HHD value of the subject.

Subjects having a muscle weakness disease with an average HHD value of less than about 80% of the predicted HHD value (e.g., relative to a normal subject of about the same age, the same gender, and/or the same height) can be treated with an alkaline phosphatase or a polypeptide having alkaline phosphatase activity (e.g. a sALP, such as TNALP, for example the sALP polypeptide of SEQ ID NO: 1 or a polypeptide variant having at least 95% sequence identity to the sequence of SEQ ID NO: 1, e.g., asfotase alfa), such as by administering an alkaline phosphatase or a polypeptide having alkaline phosphatase activity for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks). For example, a subject having a muscle weakness disease with an average HHD of less than about 80% of the predicted HHD value (e.g., about 30%, about 35%, about 40%, about 45%, about 50%, about 55%, about 60%, about 65%, about 70%, or about 75% of the predicted HHD value) can be treated with an alkaline phosphatase or a polypeptide having alkaline phosphatase activity for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks).

The methods can result in an improvement in the HHD value of a subject having a muscle weakness disease. For example, treatment with an alkaline phosphatase or a polypeptide having alkaline phosphatase activity (e.g. a sALP, such as TNALP, for example the sALP polypeptide of SEQ ID NO: 1 or a polypeptide variant having at least 95% sequence identity to the sequence of SEQ ID NO: 1, e.g., asfotase alfa), such as treatment with an alkaline phosphatase or a polypeptide having alkaline phosphatase activity for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks), can result in an average increase in the HHD value to about 80% or greater of the predicted HHD value of the patient (e.g., about 83%, about 85%, about 87%, about 90%, about 93%, about 95%, about 97%, or about 100%, or about 100% of the predictive HHD value).

The increase in the HHD value of the subject having a muscle weakness disease can be sustained throughout administration of the alkaline phosphatase or a polypeptide having alkaline phosphatase activity (e.g. a sALP, such as TNALP, for example the sALP polypeptide of SEQ ID NO: 1 or a polypeptide variant having at least 95% sequence identity to the sequence of SEQ ID NO: 1, e.g., asfotase alfa), e.g., for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the subject; particularly at least six weeks). For instance, the HHD value increases to greater than about 80% of the predicted HHD value of the subject having a muscle weakness disease and remains at ±10% of the increased HHD value during treatment with the alkaline phosphatase or a polypeptide having alkaline phosphatase activity.

Alternatively, when administration of an alkaline phosphatase or a polypeptide having alkaline phosphatase activity (e.g. a sALP, such as TNALP, for example the sALP polypeptide of SEQ ID NO: 1 or a polypeptide variant having at least 95% sequence identity to the sequence of SEQ ID NO: 1, e.g., asfotase alfa) does not result in an average increase in the HHD value to greater than 80% of the predicted HHD value (e.g., of a subject having a muscle weakness disease of about the same age, same gender, and/or height), the dosage and/or frequency of alkaline phosphatase or a polypeptide having alkaline phosphatase activity administration can be changed in order to determine the effective amount of the alkaline phosphatase or a polypeptide having alkaline phosphatase activity for the subject having a muscle weakness disease. For instance, the dosage of the alkaline phosphatase or a polypeptide having alkaline phosphatase activity can be increased from, e.g., about 2.1 mg/kg/week or about 3.5 mg/kg/week to about 6 mg/kg/week or about 9 mg/kg/week.

Alkaline Phosphatase

Asfotase alfa is a human TNALP (hTNALP; SEQ ID NO: 1) fusion protein formulated for the treatment of HPP. In particular, asfotase alfa (SEQ ID NO: 1) can be used effectively to treat hypophosphatasia (HPP), its symptoms, and physical impairments associated therewith in a subject having or being prone to a muscle weakness disease for an extended period of time (e.g., at least one day, at least one week, at least two weeks, at least three weeks, at least one month, at least three months, at least six months, at least one year, at least two years, at least three years, at least four years, at least five years, at least six years, at least seven years, at least eight years, at least nine years, at least ten years, or more than ten years (e.g., for the lifetime of the subject)).

Given the results described herein, the present disclosure is not limited to a particular alkaline phosphatase (ALP) or nucleic acid sequence encoding an ALP. Alkaline phosphatases encompass a group of enzymes that catalyze the cleavage of a phosphate moiety (e.g., hydrolysis of pyrophosphate, PPi). There are four known mammalian alkaline phosphatase (ALP) isozymes: tissue nonspecific alkaline phosphatase (TNALP; described further below), placental alkaline phosphatase (PLALP) (e.g., Accession Nos. P05187, NP_112603, and NP_001623), germ cell alkaline phosphatase (GALP) (e.g., Accession No. P10696), and intestinal alkaline phosphatase (IALP) (e.g., Accession Nos. P09923 and NP_001622). In addition to the exemplary ALPs discussed above, this disclosure also provides any polypeptide having the identical or similar catalytic site structure and/or enzymatic activity of ALP for treating subjects having or being prone to a muscle weakness disease. Bone delivery conjugates including sALP are further described in PCT publication Nos: WO 2005/103263 and WO 2008/138131.

TNALPs that can be used according to the methods described herein include, e.g., human TNALP (Accession Nos. NP_000469, AA110910, AAH90861, AAH66116, AAH21289, and AA126166); rhesus TNALP (Accession No. XP_01109717); rat TNALP (Accession No. NP_037191); dog TNALP (Accession No. AAF64516); pig TNALP (Accession No. AAN64273), mouse (Accession No. NP_031457), cow TNALP (Accession Nos. NP_789828, NP_776412, AAM 8209, and AAC33858), and cat TNALP (Accession No. NP_001036028). In particular, TNALP can be a recombinant human TNALP (e.g., SEQ ID NO: 1, asfotase alfa; see U.S. Pat. Nos. 7,763,712 and 7,960,529, incorporated herein by reference in their entirety) used for the treatment of subjects having or being prone to a muscle weakness disease. The TNALP can also be one that exhibits at least about 95% sequence identity to the polypeptide or nucleic acid sequence of the above-noted TNALPs.

Soluble Alkaline Phosphatase

The ALPs of the present invention include soluble (e.g., extracellular or non-membrane-bound) forms of any of the alkaline phosphatases described herein. The sALP of the invention can be, for example, a soluble form of human tissue non-specific alkaline phosphatase (human TNALP (hTNALP)). The present disclosure is not limited to a particular sALP and can include any sALP polypeptide that is physiologically active toward, e.g., phosphoethanolamine (PEA), inorganic pyrophosphate (PPi), and pyridoxal 5'-phosphate (PLP). In particular, a sALP of the present invention is catalytically competent to improve skeletal mineralization in bone. The present disclosure further includes nucleic acids encoding the sALPs described herein that can be used to treat muscle weakness conditions described herein, including e.g., HPP, CPPD, familial hypophosphatemia (such as autosomal dominant hypophosphatemic rickets (ADHR), autosomal recessive hypophosphatemic rickets, X-linked hypophosphatemic rickets, X-linked hypophosphatemia (XLH), etc.), etc.

TNALP is a membrane-bound protein anchored by a glycolipid moiety at the C-terminal (Swiss-Prot, P05186). This glycolipid anchor (GPI) is added post-translationally after the removal of a hydrophobic C-terminal end, which serves both as a temporary membrane anchor and as a signal for the addition of the GPI. While the GPI anchor is located in the cell membrane, the remaining portions of TNALP are extracellular. In particular, TNALP (e.g., human TNALP (hTNALP)) can be engineered to replace the first amino acid of the hydrophobic C-terminal sequence (an alanine) with a stop codon, thereby producing an engineered hTNALP that contains all amino acid residues of the native anchored form of TNALP and lacks the GPI membrane anchor. One skilled in the art will appreciate that the position of the GPI membrane anchor will vary in different ALPs and can include, e.g., the last 10, 12, 14, 16, 18, 20, 21, 22, 23, 24, 25, 26, 27, 28, 29, 30, 32, 34, 36, 38, 40, 45, 50, or more amino acid residues on the C-terminus of the polypeptide. Recombinant sTNALP can include, e.g., amino acids 1 to 502 (18 to 502 when secreted), amino acids 1 to 501 (18 to 501 when secreted), amino acids 1 to 504 (18 to 504 when secreted), amino acids 1 to 505 (18-505 when secreted), or amino acids 1 to 502. Thus, the C-terminal end of the native ALP can be truncated by certain amino acids without affecting ALP activity.

In addition to the C-terminal GPI anchor, TNALP also has an N-terminal signal peptide sequence. The N-terminal signal peptide is present on the synthesized protein when it is synthesized, but cleaved from TNALP after translocation into the ER. The sALPs of the invention include both secreted (i.e., lacking the N-terminal signal) and non-secreted (i.e., having the N-terminal signal) forms thereof. One skilled in the art will appreciate that the position of the N-terminal signal peptide will vary in different alkaline phosphatases and can include, for example, the first 5, 8, 10, 11, 12, 13, 14, 15, 16, 17, 18, 19, 20, 21, 22, 23, 24, 25, 27, 30, or more amino acid residues on the N-terminus of the polypeptide. One of skill in the art can predict the position of a signal sequence cleavage site, e.g., by an appropriate computer algorithm such as that described in Bendtsen et al. (*J. Mol. Biol.* 340(4):783-795, 2004) and available on the Web at www.cbs.dtu.dk/services/SignalP/.

The present invention also includes sALP consensus sequences derived from the extracellular domain of ALP isozymes (e.g., TNALP, PALP, GCALP, IALP, etc.). Thus, similar to sTNALP discussed above, the present disclosure also provides other soluble human ALP isozymes, i.e., without the peptide signal, preferably comprising the extracellular domain of the ALPs. The sALPs of the invention also include polypeptide sequences satisfying a consensus sequence derived from the ALP extracellular domain of human ALP isozymes and of mammalian TNALP orthologs (human, mouse, rat, cow, cat, and dog) or a consensus derived from the ALP extracellular domain of just mammalian TNALP orthologs (human, mouse, rat, cow, cat, and dog). The sALPs of the invention also include those which satisfy similar consensus sequences derived from various combinations of these TNALP orthologs or human ALP isozymes. Such consensus sequences are given, for example, in WO 2008/138131.

sALPs of the present invention can include not only the wild-type sequence of the sALPs described above, but any polypeptide having at least 50% (e.g., 55%, 60%, 65%, 70%, 75%, 80%, 85%, 86%, 87%, 88%, 89%, 90%, 91%, 92%, 93%, 94%, 95%, 96%, 97%, 98%. 99%, or more) sequence identity to these alkaline phosphatases (e.g., SEQ ID NOs: 1-24; for example the sALP polypeptide of SEQ ID NO: 1 or a polypeptide variant having at least 95% sequence identity to the sequence of SEQ ID NO: 1, e.g., asfotase alfa). Examples of mutations that can be introduced into an ALP sequence are described in US Publication No. 2013/0323244, hereby incorporated by reference in its entirety. A sALP can optionally be glycosylated at any appropriate one or more amino acid residues. In addition, an sALP can have at least 50% (e.g., 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more) sequence identity to any of the sALPs described herein (such as TNALP, for example the sALP polypeptide of SEQ ID NO: 1 or a polypeptide variant having at least 95% sequence identity to the sequence of SEQ ID NO: 1, e.g., asfotase alfa). A sALP can have 1, 2, 3, 4, 5, 6, 7, 8, 9, 10, or more additions, deletions, or substitutions relative to any of the sALPs described herein (such as TNALP, for example the sALP polypeptide of SEQ ID NO: 1 or a polypeptide variant having at least 95% sequence identity to the sequence of SEQ ID NO: 1, e.g., asfotase alfa).

sALP Fusion Polypeptides

Any of the sALPs and linkers described herein can be combined in a sALP polypeptide, e.g., a sALP polypeptide of A-sALP-B, wherein each of A and B is absent or is an amino acid sequence of at least one amino acid (such as TNALP, for example the sALP polypeptide of SEQ ID NO: 1 or a polypeptide variant having at least 95% sequence identity to the sequence of SEQ ID NO: 1, e.g., asfotase alfa). When present, A and/or B can be any linker described herein. In some sALP polypeptides, A is absent, B is absent, or A and B are both absent. The sALP polypeptides of the invention can optionally include an Fc region to provide an sALP fusion polypeptide, as described herein. The sALP polypeptide can optionally include a bone-targeting moiety, as described herein. In some sALP polypeptides, a linker, e.g., a flexible linker, can be included between the bone-targeting moiety and the sALP, such as a dipeptide sequence (e.g., leucine-lysine or aspartic acid-isoleucine). Further exemplary Fc regions, linkers, and bone-targeting moieties are described below.

Any of the sALPs, linkers, and Fc regions described herein can be combined in a fusion polypeptide, e.g., a recombinant fusion polypeptide, which includes the structure Z-sALP-Y-spacer-X-$W_n$-V, Z-$W_n$-X-spacer-Y-sALP-V, Z-sALP-Y-$W_n$-X-spacer-V, and Z-$W_n$-X-sALP-Y-spacer-V (such as TNALP, for example the sALP polypeptide of SEQ ID NO: 1 or a polypeptide variant having at least 95% sequence identity to the sequence of SEQ ID NO: 1, e.g., asfotase alfa). In particular, the structure can be Z-sALP-Y-spacer-X-W-V or Z-W-X-spacer-Y-sALP-V. The sALP can be the full-length or functional fragments of ALPs, such as the soluble, extracellular domain of the ALP, as is described herein (e.g., TNALP, PALP, GCALP and IALP). Any one of X, Y, Z, and V and/or the spacer can be absent or an amino acid sequence of at least one amino acid. $W_n$ can be a bone-targeting moiety, e.g., having a series of consecutive Asp or Glu residues, in which n=1 to 50, e.g., n=3-30, e.g., 5-15, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 36, 38, 39, 40, 41, 42, 43, 44, 45, 46, 47, 48, 49, or 50. The bone-targeting moiety, if present, can be positioned anywhere in the fusion polypeptide, e.g., at or near the N-terminal or C-terminal end, and/or in the linker region. For instance, the bone-targeting moiety is at the C-terminal end. sALP polypeptides and fusion polypeptides can also not include a bone-targeting moiety.

sALP fusion polypeptides of the present invention can be of the structure hTNALP-Fc-$D_{10}$. In particular, sALP fusion polypeptides can include an amino acid sequence of SEQ ID NO: 1 or a polypeptide variant having at least 95% sequence identity to the sequence of SEQ ID NO: 1, e.g., asfotase alfa.

Useful spacers include, but are not limited to, polypeptides comprising an Fc, and hydrophilic and flexible polypeptides able to alleviate the repulsive forces caused by the presence of the terminal highly negatively charged peptide (e.g., $W_n$). For example, a sALP can be a fusion polypeptide including an Fc region of an immunoglobulin at the N-terminal or C-terminal domain. An immunoglobulin molecule has a structure that is well known in the art. It includes two light chains (~23 kD each) and two heavy chains (~50-70 kD each) joined by inter-chain disulfide bonds. Immunoglobulins are readily cleaved proteolytically (e.g., by papain cleavage) into Fab (containing the light chain and the VH and CH1 domains of the heavy chain) and Fc (containing the CH2 and CH3 domains of the heavy chain, along with adjoining sequences). Useful Fc fragments as described herein include the Fc fragment of any immunoglobulin molecule, including IgG, IgM, IgA, IgD, or IgE, and their various subclasses (e.g., IgG-1, IgG-2, IgG-3, IgG-4, IgA-1, IgA-2), from any mammal (e.g., human). For instance, the Fc fragment is human IgG-1. The Fc fragments of the invention can include, for example, the CH2 and CH3 domains of the heavy chain and any portion of the hinge region. The Fc region can optionally be glycosylated at any appropriate one or more amino acid residues known to those skilled in the art. In particular, the Fc fragment of the fusion polypeptide has the amino acid sequence of SEQ ID NO: 20, or has at least 50% (e.g., 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more) sequence identity to SEQ ID NO: 20. Engineered, e.g., non-naturally occurring, Fc regions can be utilized in the methods of the invention, e.g., as described in International Application Pub. No. WO2005/007809, which is hereby incorporated by reference. An Fc fragment as described herein can have 1, 2, 3, 4, 5, 6, 7, 8, 9, 10, 11, 12, 13, 14, 15, 16, 17, 18, 19, 20, 25, 30, 35, 40, 50, or more additions, deletions, or substitutions relative to any of the Fc fragments described herein.

The sALP fusion polypeptides described herein (such as TNALP, for example the sALP polypeptide of SEQ ID NO: 1 or a polypeptide variant having at least 95% sequence identity to the sequence of SEQ ID NO: 1, e.g., asfotase alfa) can include a peptide linker region between the Fc fragment. In addition, a peptide linker region can be included between the Fc fragment and the optional bone-targeting moiety. The linker region can be of any sequence and length that allows the sALP to remain biologically active, e.g., not sterically hindered. Exemplary linker lengths are between 1 and 200 amino acid residues, e.g., 1-5, 6-10, 11-15, 16-20, 21-25, 26-30, 31-35, 36-40, 41-45, 46-50, 51-55, 56-60, 61-65, 66-70, 71-75, 76-80, 81-85, 86-90, 91-95, 96-100, 101-110, 111-120, 121-130, 131-140, 141-150, 151-160, 161-170, 171-180, 181-190, or 191-200 amino acid residues. For instance, linkers include or consist of flexible portions, e.g., regions without significant fixed secondary or tertiary structure. Exemplary flexible linkers are glycine-rich linkers, e.g., containing at least 50%, 60%, 65%, 70%, 75%, 80%, 85%, 90%, 95%, or even 100% glycine residues. Linkers can also contain, e.g., serine residues. In some cases, the amino acid sequence of linkers consists only of glycine and serine residues. A linker can optionally be glycosylated at any appropriate one or more amino acid residues. Additionally, a linker as described herein can include any other sequence or moiety, attached covalently or non-covalently. The linker can also be absent, in which the Fc fragment and the sALP are fused together directly, with no intervening residues. Certain Fc-sALP or sALP-Fc fusion polypeptides can be viewed, according to the present disclosure, either as 1) having no linker, or as 2) having a linker which corresponds to a portion of the sALP. For example, Fc fused directly to hsTNALP (1-502) can be viewed, e.g., either as having no linker, in which the hsTNALP is amino acids 1-502, or as having a 17-amino acid linker, in which the hsTNALP (18-502).

Additional amino acid residues can be introduced into the polypeptide according to the cloning strategy used to produce the fusion polypeptides. For instance, the additional amino acid residues do not provide an additional GPI anchoring signal so as to maintain the polypeptide in a soluble form. Furthermore, any such additional amino acid residues, when incorporated into the polypeptide of the invention, do not provide a cleavage site for endoproteases of the host cell. The likelihood that a designed sequence would be cleaved by the endoproteases of the host cell can be predicted as described, e.g., by Ikezawa (*Biol. Pharm. Bull.* 25:409-417, 2002).

The sALPs and sALP fusion polypeptides of the invention (such as TNALP, for example the sALP polypeptide of SEQ ID NO: 1 or a polypeptide variant having at least 95% sequence identity to the sequence of SEQ ID NO: 1, e.g., asfotase alfa) can be associated into dimers or tetramers. For example, two sALP-Fc monomers can covalently be linked through two disulfide bonds located in the hinge regions of the Fc fragments. Additionally, the polypeptide or fusion polypeptide of the invention (e.g., a sALP polypeptide or fusion polypeptide) can be glycosylated or PEGylated.

Production of Nucleic Acids and Polypeptides

The nucleic acids encoding sALPs and sALP fusion polypeptides of the invention (such as TNALP, for example the sALP polypeptide of SEQ ID NO: 1 or a polypeptide variant having at least 95% sequence identity to the sequence of SEQ ID NO: 1, e.g., asfotase alfa) can be produced by any method known in the art. Typically, a nucleic acid encoding the desired fusion polypeptide is generated using molecular cloning methods, and is generally placed within a vector, such as a plasmid or virus. The vector is used to transform the nucleic acid into a host cell appropriate for the expression of the fusion polypeptide. Representative methods are disclosed, for example, in Maniatis et al. (Cold Springs Harbor Laboratory, 1989). Many cell types can be used as appropriate host cells, although mammalian cells are preferable because they are able to confer appropriate post-translational modifications. Host cells of the present invention can include, e.g., Chinese Hamster Ovary (CHO) cell, L cell, C127 cell, 3T3 cell, BHK cell, COS-7 cell or any other suitable host cell known in the art. For example, the host cell is a Chinese Hamster Ovary (CHO) cell (e.g., a CHO-DG44 cell).

The sALPs and sALP fusion polypeptides (such as TNALP, for example the sALP polypeptide of SEQ ID NO: 1 or a polypeptide variant having at least 95% sequence identity to the sequence of SEQ ID NO: 1, e.g., asfotase alfa) can be produced under any conditions suitable to effect expression of the sALP polypeptide in the host cell. Such conditions include appropriate selection of a media prepared with components such as a buffer, bicarbonate and/or HEPES, ions like chloride, phosphate, calcium, sodium, potassium, magnesium, iron, carbon sources like simple sugars, amino acids, potentially lipids, nucleotides, vitamins and growth factors like insulin; regular commercially available media like alpha-MEM, DMEM, Ham's-F12, and IMDM supplemented with 2-4 mM L-glutamine and 5% Fetal bovine serum; regular commercially available animal protein free media like Hyclone™ SFM4CHO, Sigma CHO DHFR-, Cambrex POWER™ CHO CD supplemented with 2-4 mM L-glutamine. These media are desirably prepared without thymidine, hypoxanthine and L-glycine to maintain selective pressure, allowing stable protein-product expression.

Pharmaceutical Compositions and Formulations

A composition of the present invention (e.g., including a sALP or sALP fusion polypeptide, such as TNALP, for example the sALP polypeptide of SEQ ID NO: 1 or a polypeptide variant having at least 95% sequence identity to the sequence of SEQ ID NO: 1, e.g., asfotase alfa) can be administered by a variety of methods known in the art. As will be appreciated by the skilled artisan, the route and/or mode of administration will vary depending upon the desired results. The route of administration can depend on a variety of factors, such as the environment and therapeutic goals. In particular, the polypeptides and fusion polypeptides described herein can be administration by any route known in the art, e.g., subcutaneous (e.g., by subcutaneous injection), intravenously, orally, nasally, intramuscularly, sublingually, intrathecally, or intradermally. By way of example, pharmaceutical compositions of the invention can be in the form of a liquid, solution, suspension, pill, capsule, tablet, gelcap, powder, gel, ointment, cream, nebulae, mist, atomized vapor, aerosol, or phytosome.

Dosage

Any amount of a pharmaceutical composition (e.g., including a sALP or sALP fusion polypeptide, such as TNALP, for example the sALP polypeptide of SEQ ID NO: 1 or a polypeptide variant having at least 95% sequence identity to the sequence of SEQ ID NO: 1, e.g., asfotase alfa) can be administered to a subject having or being prone to a muscle weakness disease. The dosages will depend on many factors including the mode of administration and the age of the patient. Typically, the amount of the composition (e.g., a sALP or sALP fusion polypeptide, such as TNALP, for example the sALP polypeptide of SEQ ID NO: 1 or a polypeptide variant having at least 95% sequence identity to the sequence of SEQ ID NO: 1, e.g., asfotase alfa) contained within a single dose will be an amount that is effective to treat a condition (e.g., HPP) as described herein without inducing significant toxicity.

For example, the sALP polypeptides (such as TNALP, for example the sALP polypeptide of SEQ ID NO: 1 or a polypeptide variant having at least 95% sequence identity to the sequence of SEQ ID NO: 1, e.g., asfotase alfa) described herein can be administered to an subject having or being prone to a muscle weakness disease, in individual doses ranging, e.g., from 0.01 mg/kg to 500 mg/kg (e.g., from 0.05 mg/kg to 500 mg/kg, from 0.1 mg/kg to 20 mg/kg, from 5 mg/kg to 500 mg/kg, from 0.1 mg/kg to 100 mg/kg, from 10 mg/kg to 100 mg/kg, from 0.1 mg/kg to 50 mg/kg, 0.5 mg/kg to 25 mg/kg, 1.0 mg/kg to 10 mg/kg, 1.5 mg/kg to 5 mg/kg, or 2.0 mg/kg to 3.0 mg/kg) or from 1 µg/kg to 1,000 µg/kg (e.g., from 5 µg/kg to 1,000 µg/kg, from 1 µg/kg to 750 µg/kg, from 5 µg/kg to 750 µg/kg, from 10 µg/kg to 750 µg/kg, from 1 µg/kg to 500 µg/kg, from 5 µg/kg to 500 µg/kg, from 10 µg/kg to 500 µg/kg, from 1 µg/kg to 100 µg/kg, from 5 µg/kg to 100 µg/kg, from 10 µg/kg to 100 µg/kg, from 1 µg/kg to 50 µg/kg, from 5 µg/kg to 50 µg/kg, or from 10 µg/kg to 50 µg/kg).

Exemplary doses of a sALP include, e.g., 0.01, 0.05, 0.1, 0.5, 1, 2, 2.5, 5, 10, 20, 25, 50, 100, 125, 150, 200, 250, or 500 mg/kg; or 1, 2, 2.5, 5, 10, 20, 25, 50, 100, 125, 150, 200, 250, 500, 750, 900, or 1,000 µg/kg. For all dosages or ranges recited herein, the term "about" can be used to modify these dosages by ±10% of the recited values or range endpoints. In particular, compositions (e.g., including sALP (such as TNALP, for example the sALP polypeptide of SEQ ID NO: 1 or a polypeptide variant having at least 95% sequence identity to the sequence of SEQ ID NO: 1, e.g., asfotase alfa)) in accordance with the present disclosure can be administered to patients in doses ranging from about 0.001 mg/kg/day to about 500 mg/kg/day, about 0.01 mg/kg/day to about 100 mg/kg/day, or about 0.01 mg/kg/day to about 20 mg/kg/day. For example, the sALP compositions (such as TNALP, for example the sALP polypeptide of SEQ ID NO: 1 or a polypeptide variant having at least 95% sequence identity to the sequence of SEQ ID NO: 1, e.g., asfotase alfa) can be administered to patients in a weekly dosage ranging, e.g., from about 0.5 mg/kg/week to about 140 mg/kg/week, e.g., about 0.8 mg/kg/week to about 50 mg/kg/week, or about 1 mg/kg/week to about 10 mg/kg/week (e.g., about 6 or about 9 mg/kg/week). In particular, the sALP (such as TNALP, for example the sALP polypeptide of SEQ ID NO: 1 or a polypeptide variant having at least 95% sequence identity to the sequence of SEQ ID NO: 1, e.g., asfotase alfa) can be administered at a dosage of 2 mg/kg three times a week (total dose 6 mg/kg/week), 1 mg/kg six times a week (total dose 6 mg/kg/week), 3 mg/kg three times a week (total dose 9 mg/kg/week), 0.5 mg/kg three times a week (total dose of 1.5 mg/kg/week), or 9.3 mg/kg three times a week (total dose 28 mg/kg/week). The dosage will be adapted by the clinician in accordance with conventional factors such as the extent of the disease and different parameters from the subject having or being prone to a muscle weakness disease.

Dosages of compositions including sALPs and sALP fusion polypeptides (such as TNALP, for example the sALP polypeptide of SEQ ID NO: 1 or a polypeptide variant having at least 95% sequence identity to the sequence of SEQ ID NO: 1, e.g., asfotase alfa) can be provided in either a single or multiple dosage regimens. Doses can be administered, e.g., hourly, bi-hourly, daily, bi-daily, twice a week, three times a week, four times a week, five times a week, six times a week, weekly, biweekly, monthly, bimonthly, or yearly. Alternatively, doses can be administered, e.g., twice, three times, four times, five times, six times, seven times, eight times, nine times, 10 times, 11 times, or 12 times per day. In particular, the dosing regimen is once weekly. The duration of the dosing regimen can be, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 day(s), week(s), or month(s), or even for the remaining lifespan of the subject having or being prone to a muscle weakness disease. The amount, frequency, and duration of dosage will be adapted by the clinician in accordance with conventional factors such as the extent of the disease and different parameters from the subject having or being prone to a muscle weakness disease.

For example, a sALP or sALP fusion polypeptide (such as TNALP for example the sALP polypeptide of SEQ ID NO: 1 or a polypeptide variant having at least 95% sequence identity to the sequence of SEQ ID NO: 1, e.g., asfotase alfa) can be formulated as a solution for injection, which is a clear, colorless to slightly yellow, aqueous solution, pH 7.4. The sALP or sALP polypeptide (such as TNALP, for example the sALP polypeptide of SEQ ID NO: 1 or a polypeptide variant having at least 95% sequence identity to the sequence of SEQ ID NO: 1, e.g., asfotase alfa) may be formulated at a concentration of 12 mg/0.3 mL, 18 mg/0.45 mL, 28 mg/0.7 mL, 40 mg/1 ml, or 80 mg/0.8 mL. In particular, the composition can be formulated as a 40 mg/ml solution for injection, in which each ml of solution contains 40 mg of sALP or sALP polypeptide (e.g., each vial contains 0.3 ml solution and 12 mg of sALP (40 mg/ml), each vial contains 0.45 ml solution and 18 mg of sALP (40 mg/ml), each vial contains 0.7 ml solution and 28 mg of sALP (40 mg/ml), or each vial contains 1.0 ml solution and 40 mg of asfotase alfa (40 mg/ml)). A sALP or sALP polypeptide (such as TNALP, for example the sALP polypeptide of SEQ ID NO: 1 or a polypeptide variant having at least 95% sequence identity to the sequence of SEQ ID NO: 1, e.g., asfotase alfa) can be formulated as a solution for injection at a concentration of 100 mg/ml, in which each 1 ml of solution contains 100 mg of sALP or sALP polypeptide (e.g., each vial contains 0.8 ml solution and 80 mg of asfotase alfa (100 mg/ml)).

For example, the recommended dosage of a sALP or sALP fusion polypeptide ((such as TNALP, for example the sALP polypeptide of SEQ ID NO: 1 or a polypeptide variant having at least 95% sequence identity to the sequence of SEQ ID NO: 1, e.g., asfotase alfa) is 2 mg/kg of body weight administered subcutaneously three times per week, or a dosage regimen of 1 mg/kg of body weight administered subcutaneously six times per week. Additional dosage information is provided below (Table 1).

TABLE 1

DOSING OF ASFOTASE ALFA

| | If injecting 3x per week | | | If injecting 6 x per week | | |
|---|---|---|---|---|---|---|
| Body Weight (kg) | Dose to be injected | Volume to be injected | Vial type used for injection | Dose to be injected | Volume to be injected | Vial type used for injection |
| 3 | 6 mg | 0.15 ml | 0.3 ml | | | |
| 4 | 8 mg | 0.20 ml | 0.3 ml | | | |
| 5 | 10 mg | 0.25 ml | 0.3 ml | | | |
| 6 | 12 mg | 0.30 ml | 0.3 ml | 6 mg | 0.15 ml | 0.3 ml |
| 7 | 14 mg | 0.35 ml | 0.45 ml | 7 mg | 0.18 ml | 0.3 ml |
| 8 | 16 mg | 0 40 ml | 0.45 ml | 8 mg | 0.20 ml | 0.3 ml |
| 9 | 18 mg | 0.45 ml | 0.45 ml | 9 mg | 0.23 ml | 0.3 ml |
| 10 | 20 mg | 0.50 ml | 0.7 ml | 10 mg | 0.25 ml | 0.3 ml |
| 11 | 22 mg | 0.55 ml | 0.7 ml | 11 mg | 0.28 ml | 0.3 ml |
| 12 | 24 mg | 0.60 ml | 0.7 ml | 12 mg | 0.30 ml | 0.3 ml |
| 13 | 26 mg | 0.65 ml | 0.7 ml | 13 mg | 0.33 ml | 0.45 ml |
| 14 | 28 mg | 0.70 ml | 0.7 ml | 14 mg | 0.35 ml | 0.45 ml |
| 15 | 30 mg | 0.75 ml | 1 ml | 15 mg | 0.38 ml | 0.45 ml |
| 16 | 32 mg | 0.80 ml | 1 ml | 16 mg | 0.40 ml | 0.45 ml |
| 17 | 34 mg | 0.85 ml | 1 ml | 17 mg | 0.43 ml | 0.45 ml |
| 18 | 36 mg | 0.90 ml | 1 ml | 18 mg | 0.45 ml | 0.45 ml |
| 19 | 38 mg | 0.95 ml | 1 ml | 19 mg | 0.48 ml | 0.7 ml |
| 20 | 40 mg | 1.00 ml | 1 ml | 20 mg | 0.50 ml | 0.7 ml |
| 25 | 50 mg | 0.50 ml | 0.8 ml | 25 mg | 0.63 ml | 0.7 ml |
| 30 | 60 mg | 0.60 ml | 0.8 ml | 30 mg | 0.75 ml | 1 ml |

TABLE 1-continued

DOSING OF ASFOTASE ALFA

| Body Weight (kg) | If injecting 3x per week | | | If injecting 6 x per week | | |
|---|---|---|---|---|---|---|
| | Dose to be injected | Volume to be injected | Vial type used for injection | Dose to be injected | Volume to be injected | Vial type used for injection |
| 35 | 70 mg | 0.70 ml | 0.8 ml | 35 mg | 0.88 ml | 1 ml |
| 40 | 80 mg | 0.80 ml | 0.8 ml | 40 mg | 1.00 ml | 1 ml |
| 50 | | | | 50 mg | 0.50 ml | 0.8 ml |
| 60 | | | | 60 mg | 0.60 ml | 0.8 ml |
| 70 | | | | 70 mg | 0.70 ml | 0.8 ml |
| 80 | | | | 80 mg | 0.80 ml | 0.8 ml |
| 90 | | | | 90 mg | 0.90 ml | 0.8 ml (x2) |
| 100 | | | | 100 mg | 1.00 ml | 0.8 ml (x2) |

Formulations

The compositions including sALPs and sALP fusion polypeptides (such as TNALP, for example the sALP polypeptide of SEQ ID NO: 1 or a polypeptide variant having at least 95% sequence identity to the sequence of SEQ ID NO: 1, e.g., asfotase alfa) can be formulated according to standard methods. Pharmaceutical formulation is a well-established art, and is further described in, e.g., Gennaro (2000) "Remington: The Science and Practice of Pharmacy," 20$^{th}$ Edition, Lippincott, Williams & Wilkins (ISBN: 0683306472); Ansel et al. (1999) "Pharmaceutical Dosage Forms and Drug Delivery Systems," 7$^{th}$ Edition, Lippincott Williams & Wilkins Publishers (ISBN: 0683305727); and Kibbe (2000) "Handbook of Pharmaceutical Excipients American Pharmaceutical Association," 3$^{rd}$ Edition (ISBN: 091733096X). For instance, a sALP composition (such as TNALP, for example the sALP polypeptide of SEQ ID NO: 1 or a polypeptide variant having at least 95% sequence identity to the sequence of SEQ ID NO: 1, e.g., asfotase alfa) can be formulated, for example, as a buffered solution at a suitable concentration and suitable for storage at 2-8° C. (e.g., 4° C.). A composition can also be formulated for storage at a temperature below 0° C. (e.g., −20° C. or −80° C.). A composition can further be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, the compositions described herein can be stable in storage for at least 1 year at 2-8° C. (e.g., 4° C.).

The compositions including sALPs and sALP fusion polypeptides (such as TNALP, for example the sALP polypeptide of SEQ ID NO: 1 or a polypeptide variant having at least 95% sequence identity to the sequence of SEQ ID NO: 1, e.g., asfotase alfa) can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application.

For example, compositions intended for systemic or local delivery can be in the form of injectable or infusible solutions. Accordingly, the compositions (such as TNALP, for example the sALP polypeptide of SEQ ID NO: 1 or a polypeptide variant having at least 95% sequence identity to the sequence of SEQ ID NO: 1, e.g., asfotase alfa) can be formulated for administration by a parenteral mode (e.g., subcutaneous, intravenous, intraperitoneal, or intramuscular injection). "Parenteral administration," "administered parenterally," and other grammatically equivalent phrases, as used herein, refer to modes of administration other than enteral and topical administration, usually by injection, and include, without limitation, subcutaneous, intradermal, intravenous, intranasal, intraocular, pulmonary, intramuscular, intra-arterial, intrathecal, intracapsular, intraorbital, intracardiac, intradermal, intrapulmonary, intraperitoneal, transtracheal, subcuticular, intraarticular, subcapsular, subarachnoid, intraspinal, epidural, intracerebral, intracranial, intracarotid, and intrasternal injection and infusion.

The compositions including sALPs and sALP fusion polypeptides (such as TNALP, for example the sALP polypeptide of SEQ ID NO: 1 or a polypeptide variant having at least 95% sequence identity to the sequence of SEQ ID NO: 1, e.g., asfotase alfa) can be formulated as a solution, microemulsion, dispersion, liposome, or other ordered structure suitable for stable storage at high concentration. Sterile injectable solutions can be prepared by incorporating a composition described herein in the required amount in an appropriate solvent with one or a combination of ingredients enumerated above, as required, followed by filter sterilization. Generally, dispersions are prepared by incorporating a composition described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of a composition described herein plus any additional desired ingredient (see below) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

The compositions described herein can also be formulated in immunoliposome compositions. Such formulations can be prepared by methods known in the art such as, e.g., the methods described in Epstein et al. (1985) *Proc Natl Acad Sci USA* 82:3688; Hwang et al. (1980) *Proc Natl Acad Sci USA* 77:4030; and U.S. Pat. Nos. 4,485,045 and 4,544,545. Liposomes with enhanced circulation time are disclosed in, e.g., U.S. Pat. No. 5,013,556.

Compositions including sALPs and sALP fusion polypeptides (such as TNALP, for example the sALP polypeptide of SEQ ID NO: 1 or a polypeptide variant having at least 95% sequence identity to the sequence of SEQ ID NO: 1, e.g., asfotase alfa) can also be formulated with a carrier that will protect the composition (e.g., a sALP polypeptide or sALP fusion polypeptide) against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) "Sustained and Controlled Release Drug Delivery Systems," Marcel Dekker, Inc., New York.

When compositions are to be used in combination with a second active agent, the compositions can be co-formulated with the second agent, or the compositions can be formulated separately from the second agent formulation. For example, the respective pharmaceutical compositions can be mixed, e.g., just prior to administration, and administered together or can be administered separately, e.g., at the same or different times.

Compositions including sALPs and sALP fusion polypeptides (such as TNALP, for example the sALP polypeptide of SEQ ID NO: 1 or a polypeptide variant having at least 95% sequence identity to the sequence of SEQ ID NO: 1, e.g., asfotase alfa) can be formulated for administration to a patient or, if administered to a fetus, to a female carrying such fetus, along with intravenous gamma globulin therapy (IVIG), plasmapheresis, plasma replacement, or plasma exchange.

Carriers/Vehicles

Preparations containing a sALP or sALP fusion polypeptide (such as TNALP, for example the sALP polypeptide of SEQ ID NO: 1 or a polypeptide variant having at least 95% sequence identity to the sequence of SEQ ID NO: 1, e.g., asfotase alfa) can be provided to subjects having or being prone to a muscle weakness disease, in combination with pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. For example, the pharmaceutically acceptable carrier can include sodium chloride and/or sodium phosphate, in which the composition includes, e.g., about 150 mM sodium chloride and/or about 25 mM sodium phosphate, pH 7.4.

Intravenous vehicles can include fluid and nutrient replenishers, electrolyte replenishers, such as those based upon Ringer's dextrose, and the like. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, can be present in such vehicles. A thorough discussion of pharmaceutically acceptable carriers is available in Remington's Pharmaceutical Sciences (Mack Pub. Co., N.J. 1991).

The following examples are intended to illustrate, rather than limit, the disclosure.

EXAMPLES

Example 1. AKP2$^{-/-}$ Mice Study

AKP2$^{-/-}$ knockout mice are created by inactivating the gene AKP2, which encodes the mouse counterpart of human tissue-non-specific alkaline phosphatase (TNSALP). AKP2$^{-/-}$ knockout mice have been used as a model of human HPP that recapitulates HPP with onset in infancy (Narisawa et al. Dev Dyn. 1997; 208:432-446). This Example summarizes the effects to examine muscle fiber composition and strength in AKP2$^{-/-}$ mice compared with wild type (WT) mice, and to determine the effect of asfotase alfa in correcting the muscle weakness phenotype in the AKP2$^{-/-}$ mice.

Specifically, the soleus and the extensor digitorum longus (EDL) muscles were examined. To determine the muscle fiber composition, the fiber size and type were measured or detected. Muscles were harvested, sectioned and subjected to immunohistochemistry with antibodies recognizing laminin or myosin heavy chain I, IIa, or IIB, as described previously (see Barton et al. 2005 J Orthop Res. 23: 259-265; Barton et al. 2012 Faseb J. 26: 3691-3702; and Evans et al. 2008 Physiol. Genomics 35: 86-95). Image acquisition was performed on a Leica DMR epifluorescence microscope using OpenLab software. Fiber size and type was determined using MatLAB, where the laminin signal defined the boundary of each muscle fiber, and the anti-myosin antibodies detected the fiber type.

To determine the muscle fiber strength, contractile properties of soleus and EDL muscles of mice were monitored about 2 weeks from birth. Properties to be measured include: maximum force generating capacity using 120 and 100 Hz at supramaximal stimulation current; specific force (force per cross-sectional area; force frequency via calcium handling and/or fiber type differences; and fatigue using 330 msec stimulation duration every 1 sec (33% duty ratio). Effect of PPi level on the contractile function of soleus and EDL muscles was measured by exposing the dissected muscles to a range of PPi concentrations (e.g., 2, 4, 8, and 10 µM). In one exemplary experiment, Group 1 muscles were exposed to 1 and 8 µM or 4 and 10 µM and Group 2 muscles were exposed to 4 and 8 µM or 2 and 10 µM.

As the result, no difference on fiber type proportion was observed between the soleus muscles from AKP2$^{-/-}$ mice and the soleus muscles from wild type (WT) mice (FIG. 1). Compared to muscles from wild type (WT) mice, the AKP2$^{-/-}$ muscles had smaller fibers over all (FIG. 2). For example, the AKP2$^{-/-}$ muscle had more percentages of type 1 fibers (FIG. 2B), type IIa fibers (FIG. 2C), and type IIb fibers (FIG. 2D) of short size (e.g., less than 260 µm$^2$). Interestingly, the AKP2$^{-/-}$ muscle had a small population of larger myosin IIb fibers, while the wild type muscles lacked such fibers (FIG. 2D). One factor that may account for this is the small proportion of IIb fibers within the soleus muscle (~2%). Mature soleus muscles rarely have IIb fibers, but immature muscles have a faster muscle phenotype than mature muscles, and so the residual IIb fibers are still evident at this age. Taken together, the Akp2$^{-/-}$ mouse had smaller fibers with no apparent shift in fiber type.

Isolated muscle function testing was performed on the EDL and Soleus muscles from 2 week old AKP2$^{-/-}$ mice and WT controls. Both males and females were tested to distinguish any differences in force generation dependent upon gender.

Maximum force generating capacity was tested using 120 and 100 Hz for EDL and soleus at supramaximal stimulation current. Specific force (Force per cross sectional area) was determined for all muscles. There was no statistical difference in strength between different strains or different genders. Force frequency relationships were also determined as an assessment of calcium handling and/or fiber-type differences. There were no apparent differences between groups.

Fatigue tests were also performed, using a 330 msec stimulation duration every 1 sec (33% duty ratio). There were no apparent differences between groups. As shown in FIG. 3, no difference was observed between the soleus muscles from AKP2$^{-/-}$ mice and the soleus muscles from wild type (WT) mice for the mass (FIG. 3A), strength (FIG. 3B), force frequency (FIG. 3C), or fatigue parameters (FIG. 3D). Similarly, no difference was observed between the EDL muscles from AKP2$^{-/-}$ mice and the EDL muscles from wild type (WT) mice for the mass (FIG. 4A), strength (FIG. 4B), force frequency (FIG. 4C), or fatigue parameters (FIG. 4D). Note that for the figures of frequency and fatigue, error bars were not displayed for clarity. Although the N was low (N=3) for the fatigue and force-frequency results, the lack of any overt differences between groups suggests that there was truly no difference. This result is consistent with the fiber type distributions measured previously (FIG. 2).

HPP patients, CPPD patients, and the Akp2$^{-/-}$ mice all have elevated PPi in their circulation. Thus, it is likely that these elevated levels equilibrate with the muscles. The effects of PPi concentration on muscle contractile functions were then tested. A pilot study was performed using 10 μM PPi, while the wild type (WT) muscles exhibited a reversible loss in force production when exposed to 10 μM PPi. The effect of high PPi on force in muscles from WT and Akp2$^{-/-}$ Future experiments to explore the effects of PPi could be performed. For instance, in elevated PPi, the force-frequency or fatigability could be altered, exacerbating weakness. If this is to be pursued, using a single PPi concentration (e.g., 8 μM) would simplify the study.

Asfotase alfa was then administered to AKP2$^{-/-}$ mice to determine if there is a correlation between the decreased muscle force and the increased PPi circulating levels in AKP2$^{-/-}$ mice and to evaluate the asfotase alfa efficacy in correcting the related phenotype. Since untreated AKP2$^{-/-}$ mice typically die at about 12 days of age (the life span may be extended to 18-20 days, if supplemented with pyridoxine, but it is still not sufficient for muscle measurements) and are too young to measure muscle force in vivo, there was a difficulty to use untreated AKP2$^{-/-}$ mice as a control to analyze the treatment effect of asfotase alfa. Instead, a withdrawal experiment was used. Specifically, AKP2$^{-/-}$ mice were treated with asfotase alfa from birth until 35 days of age. At that time, some mice were withdrawn from treatment, and their PPi concentration and muscle force were measured and compared to those of mice receiving continued treatment. The whole study design is summarized as below:

TABLE 2

Open Label Treatment with Parallel and Randomized Control Study Design.

| Group Number | Group Description | Test Article | Route | Treatment Duration with asfotase alfa (Day) | Treatment duration with vehicle (Day) | Dosing interval | Dose level (mg/kg) | N = Per bleeding and grip force day (i.e., Day 36, 39, 42) |
|---|---|---|---|---|---|---|---|---|
| 1 | Homo_Tx-V | 35 days with asfotase alfa followed by 3 or 6 days with Vehicle | SC injection | 35 (Day 1 to Day 35) | 3 or 6 (Day 36 to Day 38 or 41) | Once a day | 8.2 | 12 Akp2$^{-/-}$ (Total: 24*) *Day 36 will not be performed (equivalent to group 2 at day 36) |
| 2 | Homo_Tx-Tx | asfotase alfa | SC injection | 35, 38, or 41 (Day 1 to Day 35, 38, or 41) | — | Once a day | 8.2 | 12 Akp2$^{-/-}$ (Total: 36) |
| 3 | WT | — | — | — | — | — | — | 12 WT (Total: 36) |
| 4 | WT_Tx-V | 35 days with asfotase alfa followed by 0, 3, or 6 days with Vehicle | SC injection | 35 (Day 1 to Day 35) | 0, 3, or 6 (None or Day 36 to Day 38 or 41) | Once a day | 8.2 | 12 WT (Total: 36) |

Figure 5B:
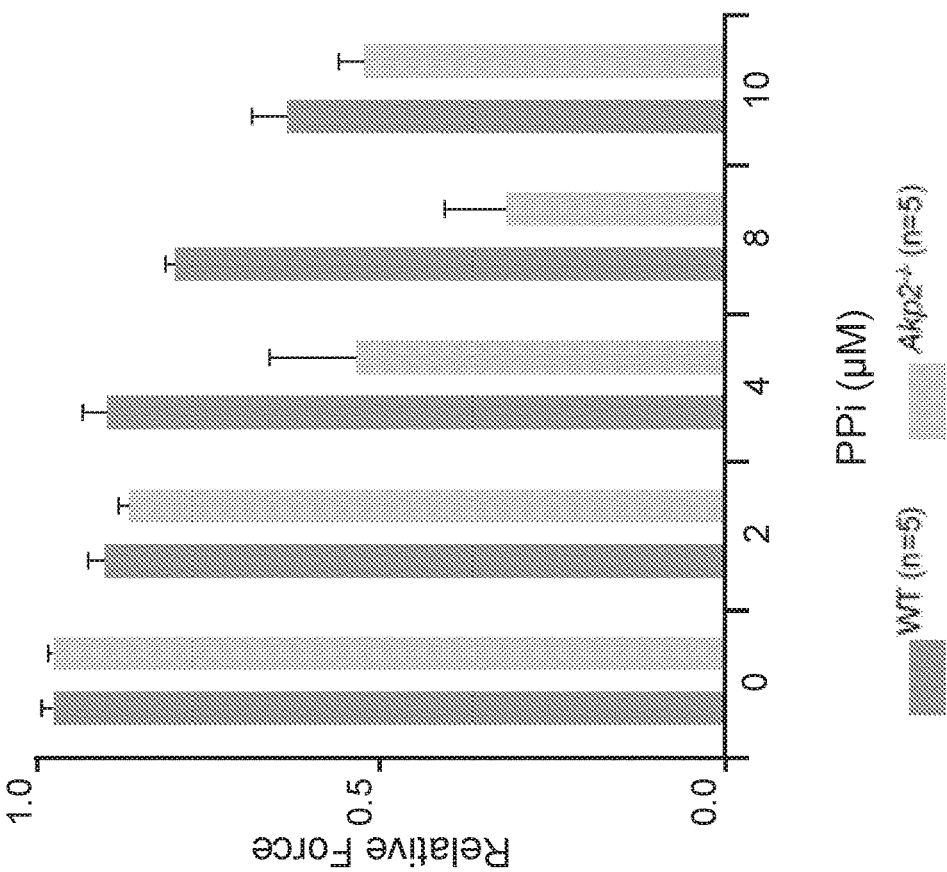
FIGS. 5A-5B are graphs of contractile properties of the dissected soleus (FIG. 5A) and extensor digitorum longus (EDL) (FIG. 5B) muscles from wild type (WT) mice or Akp2$^{-/-}$ mice in related to PPi concentration.
Figure 5A:
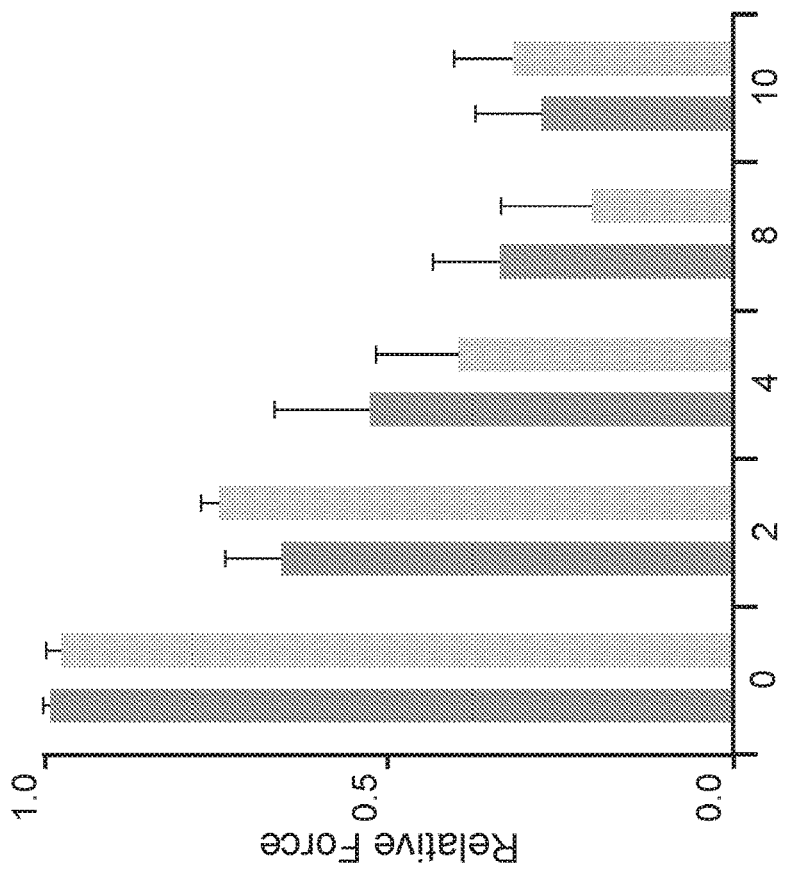

WT: represents wild-type littermate of Akp2$^{-/-}$ mice mice was then tested on a range of concentrations were tested (2, 4, 8, 10 μM) to bracket the physiological level found in the Akp2$^{-/-}$ mice and in HPP patients. An initial cohort of muscles was tested for 2 and 8 μM, or 4 and 10 μM PPi concentration. A second cohort of muscles was tested at 4 and 8 or 2 and 10 μM. Muscles were first tested in normal Ringers solution, followed by the two test conditions for 30 minutes each, and ending with a return to normal Ringers. Data from muscles that did not return to the initial force values in normal Ringers was discarded. As shown in FIG. 5B, EDL muscles from AKP2$^{-1}$ mice were more sensitive to elevated PPi than EDL muscles from wild type (WT) mice. For example, more than 4 μM PPi reduced the relative force of EDL muscles from AKP2$^{-/-}$ mice, while the relative force of EDL muscles from wild type (WT) mice did not change dramatically unless the PPi concentration was at least 10 μM (FIG. 5B). On the contrary, the soleus muscles from AKP2$^{-/-}$ mice and wild type (WT) mice were sensitive to elevated PPi in a similar degree (FIG. 5A).

8.2 mg/kg asfotase alfa was subcutaneously (SC) administered to AKP2$^{-/-}$ mice once daily from the day of birth to Day 35 after birth. Half of knockout mice then continued receiving subcutaneous administration of asfotase alfa in the same dosage regimen, while the other half received subcutaneous administration of the control vehicle in the same dosage regimen. On Day 42 both groups of AKP2' mice, as well as untreated wild type (WT) C57BL/6-129J mice, were tested for their grip force.

Five trials were performed. Scores were averaged among these trials and normalized to body weight. The grip strength of forelimbs and hindlimbs were measured and compared among wild type mice (WT), AKP2$^{-/-}$ mice receiving continuous treatment (Tx-Tx), and AKP2$^{-/-}$ mice with discontinued treatment after Day 35 (Tx-V). AKP2$^{-/-}$ mice receiving continuous treatment (Tx-Tx) showed stronger grip strength, for both fore- and hindlimbs, compared to AKP2$^{-/-}$ mice with discontinued treatment after Day 35

Figure 6:
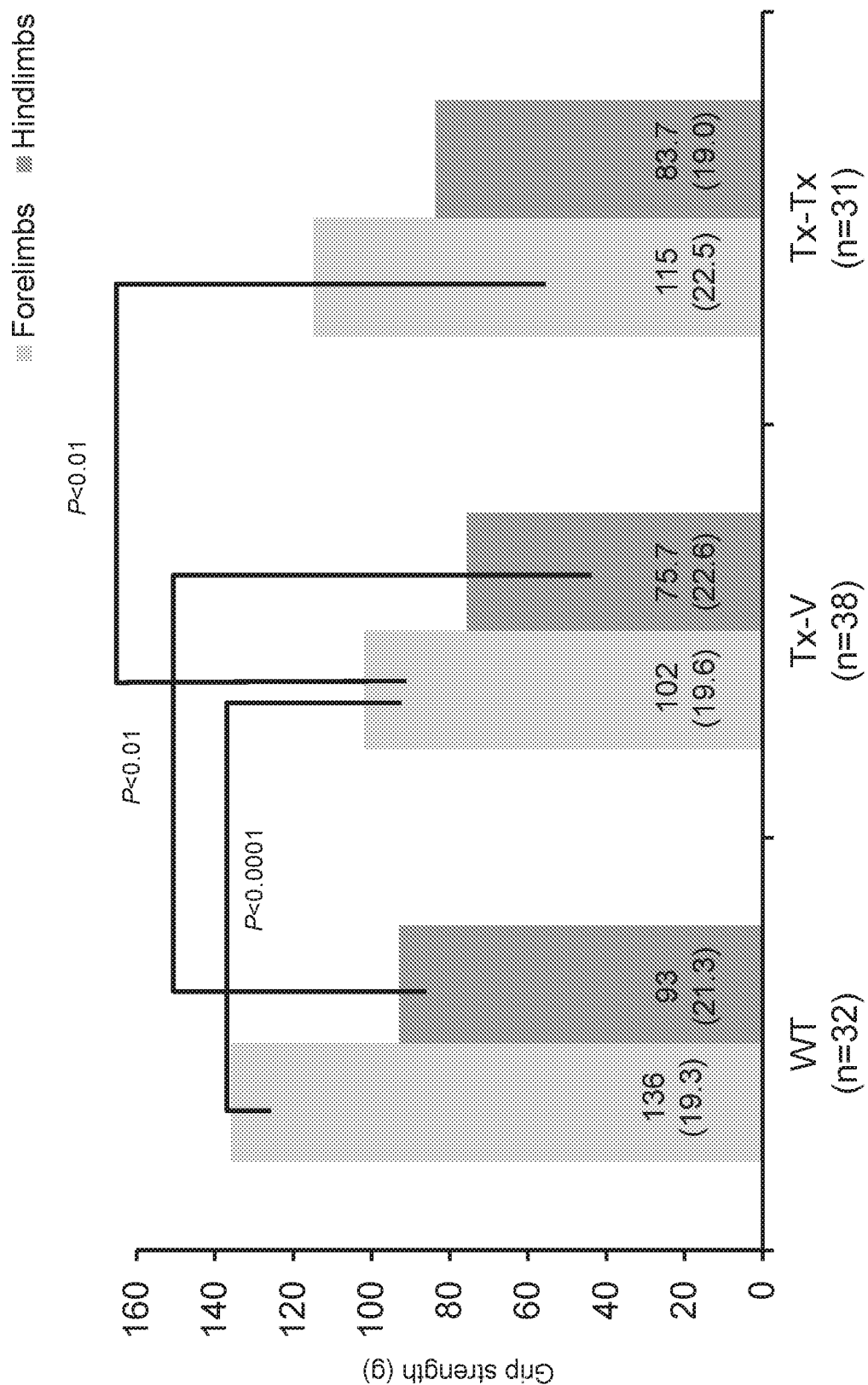
FIG. 6 is a graph of grip strength of forelimbs or hindlimbs of wild type (WT) mice, Akp2$^{-/-}$ mice receiving continuous treatment of asfotase alfa (Tx-Tx) after Day 35, or Akp2$^{-/-}$ mice with discontinued treatment of asfotase alfa (Tx-V) after Day 35.

(Tx-V), demonstrating the beneficial effect of continuous asfotase alfa treatment on a muscle weakness disease (FIG. 6).

These mice studies suggest that muscle weakness (observed in HPP) is present in the mouse model. More surprisingly, they suggest that muscle weakness in HPP is probably not due to the bone defect (which is taken as the characteristic feature of HPP), since no difference among wild type (WT) mice and AKP2$^{-/-}$ mice were observed in their soleus fiber type proportions or soleus or EDL muscle contractile properties ex vivo, even AKP2$^{-/-}$ mice had some degree of smaller muscle fibers. On the contrary, muscle weakness in HPP was more correlated to the elevated PPi concentration, since reducing PPi by administering asfotase alfa improved AKP2$^{-/-}$ mice muscle grip strength. Thus, a human patient having a muscle weakness disease characterized by elevated PPi concentration, even without other HPP symptoms or not being diagnosed with HPP yet, may still be treated by asfotase alfa. Similarly, patients having or being prone to other muscle weakness diseases, such as CPPD patients and familial hypophosphatemia patients, may also be treated by decreasing elevated PPi or other alkaline phosphatase substrates (e.g., PLP, PEA, etc.) by administration of asfotase alfa.

Example 2. Treating Muscle Weakness in Humans

As illustrated in studies in AKP2$^{-/-}$ knockout mice described above, there is a correlation between elevated PPi circulating levels (due to decreased alkaline phosphatase activity) and decreased muscle force. Such correlation may also exist in HPP patients. Asfotase alfa treatment may also be effective to correct the muscle weakness phenotype of HPP patients, or patients with other muscle weakness diseases characterized with low alkaline phosphatase activity and/or elevated PPi concentration (such as in CPPD and/or familial hypophosphatemia). This Example discloses methods of identifying a subpopulation of patients having a muscle weakness disease (e.g., HPP, CPPD, familial hypophosphatemia, etc.) with low alkaline phosphatase activity and/or elevated PPi concentration, and methods of treating, or ameliorating the muscle weakness phenotype of, a patient in such subpopulation with asfotase alfa. A patient may be identified as one of such subpopulation if having an increased PPi concentration (or an increased concentration of at least one alkaline phosphatase substrate, such as PLP and PEA) and a muscle weakness phenotype (e.g., loss of muscle force). Additionally, the patient may be identified as having a low alkaline phosphatase concentration (Table 4).

TABLE 3

Low and normal alkaline phosphatase concentrations in females and males by age group.

| | Female | | Male | |
| --- | --- | --- | --- | --- |
| Age | Low ALP (U/L) | Normal ALP (U/L) | Low ALP (U/L) | Normal ALP (U/L) |
| 0-14 d | 90 | 273 | 90 | 273 |
| 15 d-<1 y | 134 | 518 | 134 | 518 |
| 1-<10 y | 156 | 369 | 156 | 369 |
| 10-<13 y | 141 | 460 | 141 | 460 |
| 13-<15 y | 62 | 280 | 127 | 517 |
| 15-<17 y | 54 | 128 | 89 | 365 |
| 17-<19 y | 48 | 95 | 59 | 164 |

Identification of the muscle weakness disease or phenotype may be done using routine technologies known in the art. Measurement of PPi (or PLP, PEA, or other alkaline phosphatase substrates) concentration in such patient may also be carried out using routine technologies known in the art and be compared to the PPi concentration of normal subjects or subjects without such muscle weakness disease or phenotype (Table 3). Elevated PPi concentration may then be identified through this comparison.

TABLE 4

Normal ranges of pyrophosphate (PPi) levels in infants and children, adolescents, and adults.

| Category | Age | Samples (N) | Range (µM) |
| --- | --- | --- | --- |
| Infants & Children | <12 | 100 | 1.33-5.71 |
| Adolescents | 13-18 | 120 | <0.75-4.78 |
| Adult | >18 | 120 | 1.00-5.82 |

More commonly, the level of alkaline phosphatase activity in serum or plasma is measured and compared to age and sex adjusted normative data. The AKP2$^{-/-}$ knockout mice studies were performed to the murine soleus and the murine EDL muscles in order to understand the underlying etiology for hypotonia, which would be considered to be an excessively invasive test if performed in humans. Additionally, because the murine muscle tissue is physiologically plastic, data from murine muscle would be expected to be less affected than the corresponding human muscle tissue. Therefore, small changes in murine response would correlate to a larger response in human muscle tissue. In addition, because PPi is not a commercially available assay, alkaline phosphatase activity is the accepted surrogate marker for PPi levels (and are inversely correlated).

The same or different muscles may be tested for diagnosing muscle weakness diseases or phenotypes in animals or humans. For example, other skeletal or striated muscles, or cardiac or smooth muscles may be tested for various properties. For example, the passive mechanical properties (e.g., the Calcaneus Segment properties) of muscles (e.g., the gastrocnemius muscle and the Achilles Tendon) may be tested with methods known in the art. The viscoelastic property of muscle stiffness may also be tested.

Asfotase alfa was previously shown effective to treat HPP patients and a dosage of 3, 6, or 9 mg/kg/week was suggested for subcutaneous administration three times per week or once per day. The same dosage regimens, or a different one after similar studies as illustrated in Example 1, may be given to HPP patients, CPPD patients, or hypophosphatemia patients without HPP to treat the muscle weakness phenotype. To test the treatment effect, multiple endpoints may be used. Some such endpoints used in HPP treatment include, for example, the Bruininks-Oseretsky Test of Motor Proficiency 2nd Edition (BOT-2), the Radiographic Global Impression of Change (RGI-C) scale (a 7-point scale in which a rating of −3 represents severe worsening and a rating of +3 indicates near or complete healing), the Bayley Scales of Infant and Toddler Development, 3rd Edition (BSID-III), the Childhood Health Assessment Questionnaire (CHAQ), the Pediatric Outcomes Data Collection Instrument test (PODCI), the Peabody Developmental Motor Scales, 2nd Edition (PDMS-2), six-minute walk test (6 MWT), the 12-point performance-oriented mobility assessment (POMA-G), a modified performance-oriented mobility assessment (mPOMA-G, such as the one illustrated in Phillips et al. 2015 Bone Abstracts 4:P136), and other methods or tests known in the art. Both naïve patients and patients having been administered with other alkaline phosphatase therapy may be treated with asfotase alfa or other related polypeptides having alkaline phosphatase activity.

Example 3. Treating Muscle Weakness in Patient 1

A patient was identified as having hypotonia in conjunction with low ALP (correlated with high PPi), elevated PLP, and elevated urinary PEA. A 6-year-old patient presented with hypotonia of unknown etiology. The patient's additional conditions included cerebellar atrophy, axonal sensory and motor peripheral polyneuropathy, and developmental delay, with clinical and biochemical findings supporting a diagnosis of hypophosphatasia (HPP). The patient had received ongoing physical therapy since birth, and had never been able to walk without support and used a wheelchair full time. The patient was unable to eat on her own, was G-tube dependent and able to self-feed only sips of milk, and showed both receptive and expressive language delay.

The initial endocrine evaluation was part of a multidisciplinary muscular dystrophy clinic, where the patient did not say a single word during the entire visit and only used a computer-based communication device. Multiple doctors confirmed essentially no verbal output with the exception of a few single words that the patient was able to repeat during the neurological evaluation. The patient used a pulmicort nebulizer. The initial laboratory findings were: ALP 149 (normal 150-420 U/L); PLP 172.4 (normal range 20-125 nmol/L); and urinary PEA 180 (normal 0-106 nmol/mgCr).

Subcutaneous asfotase alfa injections at 6 mg/kg/week were begun three months after the patient's initial visit. At the three month follow up appointment, the parents reported that since starting the treatment, the patient appeared to have more strength when standing, and had graduated from a wheelchair by starting to use a walker. The patient showed improvement in the ability to weight bear, although the patient still required significant support. The patient was able to move her legs and showed some use of upper extremities with fairly good strength. Overall, improved postural control of the patient's trunk and neck was noted. These improvements were attributed to the patient's overall improvement in overall muscle tone and in muscle strength, confirming the hypothesis generated by the in vitro murine data.

Multiple medical professionals and the parents noted a marked increase in the patient's speech. Improvement was also noted in the patient's overall language acquisition, including using more words, and putting words together to form simple sentences. The patient's increased speaking ability could also be a result of improved muscle tone and strength in response to treatment.

Specifically, the 3 months follow up appointment noted the following improvements after asfotase alfa treatment: improved rate of growth (5.8 cm/year, compared to 1.3 cm/year prior to treatment); improved strength; improved speech, i.e., saying words spontaneously and even forming simple sentences; and improved bone mineral density by 0.5 SD within the lumbar spine.

The patient had lost two teeth in the month prior to starting asfotase alfa treatment. In radiographic findings, X-rays of the wrists showed decreased bone mineralization, but were otherwise normal, X-rays of the knees showed decreased bone mineral density, gracile bones, and abnormal tibial epiphyses. The patient showed evidence of low bone mineral density. At baseline, DXA scan showed Z-scores of −4.6 and −3.3 for the lumbar spine and the total body less head, respectively. A repeat DXA scan performed 3 months after starting asfotase alfa showed an improved LBD Z-scores by 0.5 SD, although the Z-score was still low. The BMD Z-scores were −4.1 and −3.3 for the lumbar spine and the total body less head, respectively. The patient sustained an idiopathic fracture of a humerus about a month after starting treatment; treatment with asfotase alfa continued, and the fracture healed well. Renal ultrasound and eye exams were normal at baseline.

Example 4. Treating Muscle Weakness in Patient 2

A second patient was identified as having hypotonia in conjunction with low ALP (correlated with high PPi), elevated PLP, and elevated urinary PEA. A 12 year old patient presenting with chromosomal duplication, developmental delay, autism spectrum disorder (Asperger's syndrome), and sensory processing difficulty was also noted to have a low ALP level at 90 U/L (normal range 141-460). A repeated level was again low at 91 (when tested 4 days later). The patient tired very easily, i.e., would have to rest during normal life activities involving minimal walking, and was unable to walk long distances. The patient also complained of vague pain in the shoulders, upper back, and other areas. The patient indicated that they sometimes woke up in pain and with sore shoulders and had constant pain in the legs.

The patient had no history of premature loss of teeth or of fractures. The initial occupational therapy assessment noted a fine motor score of 13 (1st percentile). Age equivalencies for response speed was 6.2 yr. Visual motor control showed a multiple year delay, i.e., at 7.9 yr level. For upper limb speed and dexterity, the patient was at 4.7 yr level. However, for teeth loss, the family history showed that one parent began to wear dentures when at 21 years old, and similarly, the maternal grandparent also had premature loss of permanent teeth and was wearing dentures at a young age. Mother's ALP level was found to be 50 U/L (reference range for the lab 40-150). The patient's initial laboratory findings were: ALP 82 (normal 150-420 U/L); PLP 210 (normal range 20-125 nmol/L); and urinary PEA 46 (normal 0-44 nmol/mgCr).

While the patient had no history of premature tooth loss, several family members did show premature tooth loss. Radiographic analysis showed normal wrist and knee x-rays. Bone mineral density analysis via DXA scan showed normal BMD (L1-L4 Z-score 2.1, TBLH Z-score 2.4). The patient had no fracture history. The patient reported pain present in multiple sites at variable times, including frequent leg pain sufficient to disturb sleep, pain on plantar surface of feet with 5-10 minutes of standing/walking, tightness/pain in quads with fatigue, bilateral knee pain, and vague shoulder/thoracic pain. Renal ultrasound did not reveal nephrocalcinosis. The patient consistently measured at the 90% percentile for height and at the 92% percentile for weight.

The patient had no significant physical activity impairments when fully rested, however, demonstrated quad fatigue with impaired knee control and bilateral foot slap due to dorsiflexion weakness after ambulating more than two minutes. The patient was able to walk on toes, but demonstrated significant compensations when attempting to ambulate on heels. The patient's initial six minute walk test was 320 meters, significantly below the age/gender norm=672+55 meters. Patient required two standing rest breaks leaning on wall secondary to fatigue. Patient demonstrated gradually increased gait impairments, including quad fatigue and foot slap due to dorsiflexion weakness, and required seated rest break following the 6 MWT. The patient had trouble with exercise and became winded easily.

The patient began subcutaneous asfotase alfa injections at 6 mg/kg/week and was re-evaluated after 4 months of treatment. Overall, the patient showed multiple improvements, including in strength, agility, and endurance. The patient's 6 minute walk test improved to 597 meters (from the initial value of 320 meters). Overall, after treatment, the patient had much less pain (score of 2 out of 10, instead of 5 out of 10 reported during the previous visit) and improved mobility. These improvements were attributed to the patient's overall improvement in overall muscle tone and in muscle strength, confirming the hypothesis generated by the in vitro murine data.

OTHER EMBODIMENTS

All publications, patents, and patent applications mentioned in the above specification are hereby incorporated by reference to the same extent as if each individual publication, patent or patent application was specifically and individually indicated to be incorporated by reference in its entirety. Various modifications and variations of the described methods, pharmaceutical compositions, and kits of the invention will be apparent to those skilled in the art without departing from the scope and spirit of the claimed invention. Although the disclosure has been described in connection with specific embodiments, it will be understood that it is capable of further modifications and that the invention as claimed should not be unduly limited to such specific embodiments.

The invention claimed is:

1. A method of treating or ameliorating a muscle weakness disease characterized by a reduction in muscle strength in a human subject having or prone to the muscle weakness disease, comprising administering a therapeutically effective amount of a recombinant alkaline phosphatase polypeptide selected from a tissue nonspecific alkaline phosphatase (TNALP) having at least 95% sequence identity to amino acids 1-485 of SEQ ID NO: 1, a placental alkaline phosphatase (PALP), a germ cell alkaline phosphatase (GCALP), and an intestinal alkaline phosphatase (IALP) to the subject, wherein the subject has an elevated serum concentration of pyrophosphate (PPi), and wherein the subject:
   (a) has not been previously diagnosed with hypophosphatasia (HPP);
   (b) has HPP and does not have any other symptoms associated with HPP; or
   (c) does not have HPP; and
   wherein the treating or ameliorating restores muscle strength reduced by the muscle weakness disease in the subject.

2. The method of claim 1, wherein said subject has low alkaline phosphatase activity.

3. The method of claim 1, wherein a muscle of said subject is not significantly different from a muscle of a normal subject without said muscle weakness disease in at least one property selected from muscle fiber type proportion and fiber contractile properties, and/or wherein the muscle weakness disease is at least one of hypophosphatasia (HPP), calcium pyrophosphate dihydrate crystal deposition (CPPD), and familial hypophosphatemia.

4. The method of claim 3, wherein the muscle is at least one type of leg muscle, and/or wherein the familial hypophosphatemia comprises at least one of autosomal dominant hypophosphatemic rickets (ADHR), autosomal recessive hypophosphatemic rickets, X-linked hypophosphatemic rickets, and X-linked hypophosphatemia (XLH).

5. The method of claim 1, wherein the recombinant alkaline phosphatase polypeptide is administered:
   a) to the subject daily for at least one week, one month, three months, six months, or one year; or
   b) by at least one of subcutaneous, intravenous, intramuscular, sublingual, intrathecal, and intradermal routes.

6. The method of claim 1, wherein the recombinant alkaline phosphatase polypeptide comprises amino acids 1-485 of SEQ ID NO: 1.

7. The method of claim 1, wherein the recombinant alkaline phosphatase polypeptide is:
   a) administered in a dosage from about 0.1 mg/kg/day to about 20 mg/kg/day, or a weekly dosage;
   b) administered in a dosage from about 0.5 mg/kg/day to about 20 mg/kg/day, or a weekly dosage;
   c) administered in a dosage from about 0.5 mg/kg/day to about 10 mg/kg/day, or a weekly dosage; and/or
   d) administered in a dosage from about 1 mg/kg/day to about 10 mg/kg/day, or a weekly dosage.

8. The method of claim 1, wherein the method comprises at least one of:
   a) prior to administration of the recombinant alkaline phosphatase polypeptide the subject is characterized as having an average walking distance in six minutes of about 350 meters or less;
   b) administration of the recombinant alkaline phosphatase polypeptide results in an increase in an average walking distance in six minutes of at least 100 meters or more;
   c) the subject exhibits an average walking distance in six minutes of about 500 meters or more after administration of the recombinant alkaline phosphatase polypeptide;
   d) the subject exhibits decreased reliance on an assistive mobility device after administration of the recombinant alkaline phosphatase polypeptide, wherein, optionally, the assistive mobility device is at least one device selected from the group consisting of a walker, a wheelchair, braces, crutches, and orthotics;
   e) prior to administration of the recombinant alkaline phosphatase polypeptide, the subject is characterized as having a plasma PPi concentration of about 4.5 µM or greater;
   f) administration of the recombinant alkaline phosphatase polypeptide results in a median decrease in PPi concentration in a plasma sample from the subject of at least about 1 µM;
   g) the subject exhibits a plasma PPi concentration of about 2 µM to about 5 µM after administration of the recombinant alkaline phosphatase polypeptide;
   h) prior to administration of the recombinant alkaline phosphatase polypeptide (ALP), the subject is characterized as having a plasma ALP concentration of about 90 U/L or less for a subject of 0 to 14 days of age; about 134 U/L or less for a subject of 15 days of age to less than 1 year of age; about 156 U/L or less for a subject of about 1 year of age to less than 10 years of age; about 141 U/L or less for a subject of about 10 years of age to less than about 13 years of age; about 62 U/L or less for a female subject of about 13 years of age to less than about 15 years of age; about 127 U/L or less for a male subject of about 13 years of age to less than about 15 years of age; about 54 U/L or less for a female subject of about 15 years of age to less than about 17 years of age; about 89 U/L or less for a male subject of about 15 years of age to less than about 17 years of age; about 48 U/L or less for a female subject of about 17 years of age or older; or about 59 U/L or less for a male subject of about 17 years of age or older;
   i) administration of the recombinant alkaline phosphatase polypeptide results in a median increase in ALP concentration in a plasma sample from the subject of at least about 100 U/L or greater;
   j) after administration of the recombinant alkaline phosphatase polypeptide, the subject exhibits a plasma ALP concentration of about 273 U/L or greater for a subject of 0 to 14 days of age; about 518 U/L or greater for a subject of 15 days of age to less than 1 year of age; about 369 U/L or greater for a subject of about 1 year of age to less than 10 years of age; about 460 U/L or greater for a subject of about 10 years of age to less than about 13 years of age; about 280 U/L or greater for a female subject of about 13 years of age to less than about 15 years of age; about 517 U/L or greater for a male subject of about 13 years of age to less than about 15 years of age; about 128 U/L or greater for a female subject of about 15 years of age to less than about 17 years of age; about 365 U/L or greater for a male subject of about 15 years of age to less than about 17 years of age; about 95 U/L or greater for a female subject of about 17 years of age or older; or about 164 U/L or greater for a male subject of about 17 years of age or older;

k) prior to administration of the recombinant alkaline phosphatase polypeptide, the subject is characterized as having an average Bruininks-Oseretsky Test of Motor Proficiency 2nd Edition (BOT-2) strength score of about 10 or less;

l) administration of the recombinant alkaline phosphatase polypeptide results in an average BOT-2 strength score of the subject of about 10 or more;

m) prior to administration of the recombinant alkaline phosphatase polypeptide, the subject is characterized as having an average BOT-2 running speed and agility score of about 5 or less;

n) administration of the recombinant alkaline phosphatase polypeptide results in an average BOT-2 running speed and agility score of the subject of about 5 or more;

o) prior to administration of the recombinant alkaline phosphatase polypeptide, the subject is characterized as having an average Childhood Health Assessment Questionnaire (CHAQ) index score of about 0.8 or more;

p) administration of the recombinant alkaline phosphatase polypeptide results in an average CHAQ index score of the subject of about 0.5 or less;

q) prior to administration of the recombinant alkaline phosphatase polypeptide, the subject is characterized as having an average Pediatric Outcomes Data Collection Instrument (PODCI) score of about 40 or less;

r) administration of the recombinant alkaline phosphatase polypeptide results in an average PODCI score of the subject of about 40 or more;

s) prior to administration of the recombinant alkaline phosphatase polypeptide, the subject is characterized as having an average Muscle Strength Grade of less than about 5;

t) administration of the recombinant alkaline phosphatase polypeptide results in an average increase in a Muscle Strength Grade of the subject of about 1 or more;

u) administration of the recombinant alkaline phosphatase polypeptide results in an average increase in a Muscle Strength Grade of the subject of about 1 or more;

v) prior to administration of the recombinant alkaline phosphatase polypeptide, the subject is characterized as having an average Hand Held Dynamometry (HHD) value of less than about 80% of a predicted HHD value; and w) administration of the recombinant alkaline phosphatase polypeptide results in an average HHD value of the subject of about 80% or more of a predicted HHD value, wherein, optionally, the HHD value represents the grip strength, knee flexion, knee extension, hip flexion, hip extension, or hip abduction of the subject.

9. The method of claim 4, wherein the leg muscle is at least one type selected from soleus and extensor digitorum longus (EDL) muscles.

10. The method of claim 1, wherein the subject has not been previously diagnosed with HPP.

11. The method of claim 1, wherein the subject has HPP and does not have any other symptoms associated with HPP.

12. The method of claim 1, wherein the subject does not have HPP.

13. The method of claim 1, wherein said muscle weakness disease is caused by an elevated concentration of pyrophosphate (PPi) and/or low alkaline phosphatase activity.

14. The method of claim 1, wherein an elevated concentration of pyrophosphate (PPi) enhances muscle weakness in said subject.

15. The method of claim 1, wherein the recombinant alkaline phosphatase polypeptide reduces the concentration of pyrophosphate (PPi) in said subject.

16. The method of claim 6, wherein the recombinant alkaline phosphatase polypeptide is asfotase alfa and is administered subcutaneously at a dosage of 6 mg/kg one time per week, 3 mg/kg two times per week, 2 mg/kg three times per week, or 1 mg/kg six times per week.

17. The method of claim 1, wherein the recombinant alkaline phosphatase polypeptide comprises the amino acid sequence of SEQ ID NO: 1.

18. The method of claim 1, wherein the recombinant alkaline phosphatase polypeptide:
a) is a fusion protein;
b) comprises an immunoglobulin molecule; or
c) comprises the structure:

Z-sALP-Y-spacer-X-$W_n$-V, wherein sALP is the recombinant alkaline phosphatase polypeptide;
V is absent or is at least one amino acid residue;
X is absent or is at least one amino acid residue;
Y is absent or is at least one amino acid residue;
Z is absent or is at least one amino acid residue; and
$W_n$ is a polyaspartate or a polyglutamate wherein n=10 to 16.

19. The method of claim 18, wherein the immunoglobulin molecule comprises a fragment crystallizable region (Fc).

20. The method of claim 19, wherein the Fc comprises an amino acid sequence of SEQ ID NO: 20.

21. The method of claim 18, wherein $W_n$ is selected from the group consisting of $D_{10}$, $D_{16}$, $E_{10}$, and $E_{16}$.

22. The method of claim 18, wherein the spacer comprises a fragment crystallizable region (Fc) and wherein the recombinant alkaline phosphatase polypeptide comprises the structure of sALP-Fc-$D_{10}$.

23. The method of claim 18, wherein the recombinant alkaline phosphatase polypeptide comprises a dimer comprising monomers of the amino acid sequence of SEQ ID NO: 1.

* * * * *

UNITED STATES PATENT AND TRADEMARK OFFICE
CERTIFICATE OF CORRECTION

PATENT NO. : 11,186,832 B2
APPLICATION NO. : 16/089744
DATED : November 30, 2021
INVENTOR(S) : Andre Marozsan It is certified that error appears in the above-identified patent and that said Letters Patent is hereby corrected as shown below:

In the Claims

Column 115, Claim 8, Line 53, through Column 116, Line 6, replace:
"t) administration of the recombinant alkaline phosphatase polypeptide results in an
    average increase in a Muscle Strength Grade of the subject of about 1 or more;
u) administration of the recombinant alkaline phosphatase polypeptide results in an
    average increase in a Muscle Strength Grade of the subject of about 1 or more;
v) prior to administration of the recombinant alkaline phosphatase polypeptide, the
    subject is characterized as having an average Hand Held Dynamometry (HHD)
    value of less than about 80% of a predicted HHD value; and
w) administration of the recombinant alkaline phosphatase polypeptide results in an
    average HHD value of the subject of about 80% or more of a predicted HHD value,
    wherein, optionally, the HHD value represents the grip strength, knee flexion, knee
    extension, hip flexion, hip extension, or hip abduction of the subject."

With:
--t) administration of the recombinant alkaline phosphatase polypeptide results in
    an average increase in a Muscle Strength Grade of the subject of about 1 or
    more;
u) prior to administration of the recombinant alkaline phosphatase polypeptide, the
    subject is characterized as having an average Hand Held Dynamometry (HHD)
    value of less than about 80% of a predicted HHD value; and
v) administration of the recombinant alkaline phosphatase polypeptide results in
    an average HHD value of the subject of about 80% or more of a predicted HHD
    value, wherein, optionally, the HHD value represents the grip strength, knee flexion
    knee extension, hip flexion, hip extension, or hip abduction of the subject.--

Signed and Sealed this
Seventeenth Day of May, 2022

Katherine Kelly Vidal
*Director of the United States Patent and Trademark Office*